US010875904B2

(12) United States Patent
Schmitt et al.

(10) Patent No.: US 10,875,904 B2
(45) Date of Patent: Dec. 29, 2020

(54) ENHANCED AFFINITY T CELL RECEPTORS AND METHODS FOR MAKING THE SAME

(71) Applicant: FRED HUTCHINSON CANCER RESEARCH CENTER, Seattle, WA (US)

(72) Inventors: Thomas M. Schmitt, Seattle, WA (US); Philip D. Greenberg, Mercer Island, WA (US)

(73) Assignee: FRED HUTCHINSON CANCER RESEARCH CENTER, Seattle, WA (US)

( * ) Notice: Subject to any disclaimer, the term of this patent is extended or adjusted under 35 U.S.C. 154(b) by 11 days.

(21) Appl. No.: 15/692,846

(22) Filed: Aug. 31, 2017

(65) Prior Publication Data

US 2017/0362298 A1 Dec. 21, 2017

Related U.S. Application Data

(62) Division of application No. 14/398,206, filed as application No. PCT/US2013/039316 on May 2, 2013, now Pat. No. 9,751,928.

(60) Provisional application No. 61/642,358, filed on May 3, 2012.

(51) Int. Cl.

| | |
|---|---|
| ***C12Q 1/68*** | (2018.01) |
| ***A01K 67/027*** | (2006.01) |
| ***C07K 14/725*** | (2006.01) |
| ***A61K 39/00*** | (2006.01) |
| ***C12N 5/0783*** | (2010.01) |
| ***C12N 5/078*** | (2010.01) |
| ***A61K 38/17*** | (2006.01) |
| ***A61K 35/17*** | (2015.01) |
| ***G01N 33/569*** | (2006.01) |

(52) U.S. Cl.

CPC .......... *C07K 14/7051* (2013.01); *A61K 35/17* (2013.01); *A61K 38/1774* (2013.01); *A61K 39/0011* (2013.01); *A61K 39/001153* (2018.08); *A61K 39/001168* (2018.08); *C12N 5/065* (2013.01); *C12N 5/0636* (2013.01); *G01N 33/56966* (2013.01); *A61K 2039/5156* (2013.01); *A61K 2039/5158* (2013.01); *C12N 2501/42* (2013.01); *C12N 2502/1394* (2013.01); *C12N 2502/99* (2013.01); *G01N 2333/7051* (2013.01)

(58) Field of Classification Search

None

See application file for complete search history.

(56) References Cited

U.S. PATENT DOCUMENTS

| | | | |
|---|---|---|---|
| 6,040,177 | A | 3/2000 | Riddell et al. |
| 6,759,243 | B2 | 7/2004 | Kranz et al. |
| 7,575,925 | B2 | 8/2009 | Schmitt et al. |
| 8,119,772 | B2 | 2/2012 | Yang et al. |
| 8,217,144 | B2 | 7/2012 | Jakobsen et al. |
| 2002/0001826 | A1 | 1/2002 | Wager et al. |
| 2004/0171148 | A1 | 9/2004 | Schmitt et al. |
| 2009/0217403 | A1 | 8/2009 | Spits |

FOREIGN PATENT DOCUMENTS

| | | | |
|---|---|---|---|
| EA | 012507 | B1 | 10/2009 |
| WO | 00/26249 | A1 | 5/2000 |
| WO | 01/055366 | A1 | 8/2001 |
| WO | 03/046141 | A2 | 6/2003 |
| WO | 2006/132524 | A1 | 12/2006 |
| WO | 2010/058023 | A1 | 5/2010 |

OTHER PUBLICATIONS

Jonson, et al. (Jul. 16, 2009) "Gene therapy with human and mouse T-cell receptors mediates cancer regression and targets normal tissues expressing cognate antigen", Gene Therapy, 114(3): 535-46.*

Van Loenen, et al. (Nov. 25, 2010) "Optimization of the HA-1-specific T-cell receptor for gene therapy of hematologic malignancies", Haematologica, 96(3): 477-81.*

Thomas, et al. (2007) "Targeting the Wilms Tumor Antigen 1 by TCR gene Transfer: TCR Variants Improve Tetramer Binding but Not the Function of Gene Modified Human T Cells", The Journal of Immunology, 179: 5803-10.*

Nicholson, et al. (2012) "Improving TCR Gene Therapy for Treatment of Haematological Malignancies", Advances in Hematology, Article ID 404081, 11 pages.*

Berry, et al. (2009) "Adoptive immunotherapy for cancer: the next generation of gene-engineered immune cells", Tissue Antigens, 74: 277-89 (Year: 2009).*

Carpenito, et al. (2009) "Control of large, established tumor xenografts with genetically retargeted human T cells containing CD28 and CD137 domains", Proceedings of the National Academy of Sciences, USA, 106(9): 3360-65 (Year: 2009).*

Stauss, et al. (2008) "WT1-specific T cell receptor gene therapy: Improving TCR function in transduced T cells", Blood Cells, Molecules and Diseases, 40: 113-116 (Year: 2008).*

Rossig, et al. (2004) "Genetic Modification of T Lymphocytes for Adoptive Immunotherapy", Molecular Therapy, 10(1): 5-18 (Year: 2004).*

Panda, et al. (2015) "T-Cell Therapy: Options for Infectious Diseases", Clinical Infectious Diseases, 61(S3): S217-224. (Year: 2015).*

Hung, et al. (2007) "Control of mesothelin-expressing ovarian cancer using adoptive transfer of mesothelin peptide-specific CD8+ T cells", Gene Therapy, 14: 921-29. (Year: 2007).*

Axelsson-Robertson, et al. (2012) "The Immunological Footprint of Mycobacterium tuberculosis T-cell Epitope Recognition", The Journal of Infectious Disease, 205: S301-15. (Year: 2012).*

(Continued)

*Primary Examiner* — Robert M Kelly

(74) *Attorney, Agent, or Firm* — Seed IP Law Group LLP

(57) ABSTRACT

The present disclosure provides methods for generating enhanced affinity T cell receptors by agonist selection of hematopoietic progenitor cells expressing an antigen specific TCRα cultured with stromal cells expressing Delta-like-1 or Delta-like-4, compositions prepared from such methods, and uses of thereof.

33 Claims, 11 Drawing Sheets

Specification includes a Sequence Listing.

(56) References Cited

OTHER PUBLICATIONS

Aggen, "Engineering Human Single-Chain T Cell Receptors," Dissertation, submitted to the University of Illinois at Urbana-Champaign, 2010, 181 pages.
Akatsuka et al., "Efficient cloning and expression of HLA class I cDNA in human B-lymphoblastoid cell lines," *Tissue Antigens* 59:502-511, 2002.
Alli et al., "Rational Design of T Cell Receptors with Enhanced Sensitivity for Antigen," *PLoS One* 6(3):e18027, 2011, 11 pages.
Altman et al., "Phenotypic Analysis of Antigen-Specific T Lymphocytes," *Science* 274(5284):94-96, 1996.
Berger et al., "Adoptive transfer of effector $CD8^+$ T cells derived from central memory cells establishes persistent T cell memory in primates," *The Journal of Clinical Investigation* 118(1):294-305, 2008.
Birkholz et al., "A fast and robust method to clone and functionally validate T-cell receptors," *Journal of Immunological Methods* 346:45-54, 2009.
Borràs et al., "Findings on T cell specificity revealed by synthetic combinatorial libraries," *Journal of Immunological Methods* 267:79-97, 2002.
Brusko et al., "Human regulatory T cells: role in autoimmune disease and therapeutic opportunities," *Immunological Reviews* 223:371-390, 2008.
Chervin et al., "Engineering higher affinity T cell receptors using a T cell display system," *Journal of Immunological Methods* 339:175-184, 2008.
Dossett et al., "Adoptive Immunotherapy of Disseminated Leukemia With TCR-transduced, $CD8^+$ T Cells Expressing a Known Endogenous TCR," *Molecular Therapy* 17(4):742-749, 2009.
Egawa et al., "Lineage Diversion of T Cell Receptor Transgenic Thymocytes Revealed by Lineage Fate Mapping," *PLoS One* 1:e1512, 2008, 7 pages.
Engels et al., "Retroviral Vectors for High-Level Transgene Expression in T Lymphocytes," *Human Gene Therapy* 14:1155-1168, 2003.
Frecha et al., "Advances in the Field of Lentivector-based Transduction of T and B Lymphocytes for Gene Therapy," *Molecular Therapy* 18(10):1748-1757, 2010.
Fujio et al., "Gene Therapy of Arthritis With TCR Isolated from the Inflamed Paw," *The Journal of Immunology* 177(11):8140-8147, 2006.
Gaiger et al., "Immunity to WT1 in the animal model and in patients with acute myeloid leukemia," *Blood* 96(4):1480-1489, 2000.
Garcia et al., "Kinetics and thermodynamics of T cell receptor-autoantigen interactions in murine experimental autoimmune encephalomyelitis," *PNAS* 98(12):6818-6823, 2001.
Ha et al., "Transplantation of mouse HSCs genetically modified to express a CD4-restricted TCR results in long-term immunity that destroys tumors and initiates spontaneous autoimmunity," *Journal of Clinical Investigation* 120(12):4273-4288, 2010.
Hiemstra et al., "Antigen arrays in T cell immunology," *Current Opinion in Immunology* 12(1):80-84, 2000.
Hinrichs et al., "Adoptively transferred effector cells derived from naïve rather than central memory CD8+ T cells mediate superior antitumor immunity," *PNAS* 106(41):17469-17474, 2009.
Hogquist et al., "T Cell Receptor Antagonist Peptides Induce Positive Selection," *Cell* 76:17-27, 1994.
Holmes et al., "The OP9-DL1 System: Generation of T-Lymphocytes from Embryonic or Hematopoietic Stem Cells In Vitro," *Cold Spring Harb. Protoc*. 4(2), 2009, 13 pages.
Hung et al., "Control of mesothelin-expressing ovarian cancer using adoptive transfer of mesothelin peptide-specific $CD8^+$ T cells," *Gene Ther*. 14(12):921-929, 2007. (18 pages).
Itoh et al., "Reproducible Establishment of Hemopoietic Supportive Stromal Cell Lines from Murine Bone Marrow," *Experimental Hematology* 17(2):145-153, 1989.
James et al., "Visualizing Antigen Specific CD4+ T Cells using MHC Class II Tetramers," *Journal of Visualized Experiments* 25: 2009, 5 pages.
June, "Adoptive T cell therapy for cancer in the clinic," *The Journal of Clinical Investigation* 117(6):1466-1476, 2007.
Kalergis et al., "A simplified procedure for the preparation of MHC / peptide tetramers: chemical biotinylation of an unpaired cysteine engineered at the C-terminus of MHC-I," *Journal of Immunological Methods* 234:61-70, 2000.
Kieback et al., "Enhanced T cell receptor gene therapy for cancer," *Expert Opin. Biol. Ther*. 10(5):749-762, 2010.
Kitchen et al., "Engineering Antigen-Specific T Cells from Genetically Modified Human Hematopoietic Stem Cells in Immunodeficient Mice," *PLoS One* 4(12):e8208, 2009, 9 pages.
Kodama et al., "Involvement of the *c-kit* receptor in the adhesion of hematopoietic stem cells to stromal cells," *Experimental Hematology* 22:979-984, 1994.
Kuball et al., "Increasing functional avidity of TCR-redirected T cells by removing defined *N*-glycosylation sites in the TCR constant domain," *J. Exp. Med.* 206(2):463-475, 2009.
Kurokawa et al., "Paired cloning of the T cell receptor $\alpha$ and $\beta$ genes from a single T cell without the establishment of a T cell clone," *Clinical and Experimental Immunology* 123(2):340-345, 2001.
La Motte-Mohs et al., "Induction of T-cell development from human cord blood hematopoietic stem cells by Delta-like 1 in vitro," *Blood* 105(4):1431-1439, 2005.
Laugel et al., "Different T Cell Receptor Affinity Thresholds and CD8 Coreceptor Dependence Govern Cytotoxic T Lymphocyte Activation and Tetramer Binding Properties," *The Journal of Biological Chemistry* 282(33):23799-237810, 2007.
Letourneur et al., "Derivation of a T cell hybridoma variant deprived of functional T cell receptor $\alpha$ and $\beta$ chain transcripts reveals a nonfunctional $\alpha$-mRNA of BW5147 origin," *Eur. J. Immunol.* 19:2269-2274, 1989.
Li et al., "Directed evolution of human T-cell receptors with picomolar affinities by phage display," *Nature Biotechnology* 23(3):349-354, 2005.
Luo et al., "Development of genetically engineered $CD4^+$ and $CD8^+$ T cells expressing TCRs specific for a *M. tuberculosis* 38-kDa antigen," *J Mol Med* 89:903-913, 2011.
Mohtashami et al., "Induction of T-cell development by Delta-like 4-expressing fibroblasts," *International Immunology* 25(10):601-611, 2013.
Molloy et al., "Soluble T cell receptors: novel immunotherapies," *Current Opinion in Pharmacology* 5:438-443, 2005.
Morgan et al., "Cancer Regression in Patients After Transfer of Genetically Engineered Lymphocytes," *Science* 314(5796):126-129, 2006. (10 pages).
Moysey et al., "Directed evolution of human T-cell receptors with picomolar affinities by phage display," *Nature Biotechnology* 23(3):349-354, 2005.
Pennington et al., "$\gamma\delta$ T cell development—having the strength to get there," *Current Opinion in Immunology* 17:108-115, 2005.
Pouw et al., "Gene transfer of human TCR in primary murine T cells is improved by pseudo-typing with amphotropic and ecotropic envelopes," *The Journal of Gene Medicine* 9:561-570, 2007.
Richman et al., "Display, engineering, and applications of antigen-specific T cell receptors," *Biomolecular Engineering* 24:361-373, 2007.
Rossi et al., "Genetic therapies against HIV," *Nature Biotechnology* 25(12):1444-1455, 2007.
Sandberg et al., "Human T-cell lines with well-defined T-cell receptor gene rearrangements as controls for the BIOMED-2 multiplex polymerase chain reaction tubes," *Leukemia* 21(2):230-237, 2007.
Schmid et al., "Evidence for a TCR Affinity Threshold Delimiting Maximal CD8 T Cell Function," *The Journal of Immunology* 184(9):4936-4946, 2010.
Schmitt et al., "Induction of T cell development and establishment of T cell competence from embryonic stem cells differentiated in vitro," *Nature Immunology* 5(4):410-417, 2004.

(56) References Cited

OTHER PUBLICATIONS

Schmitt et al., "Induction of T Cell Development from Hematopoietic Progenitor Cells by Delta-like-1 In Vitro," *Immunity* 17(6):749-756, 2002.
Schmitt et al., "T Cell Receptor Gene Therapy for Cancer," *Human Gene Therapy* 20:1240-1248, 2009.
Scholten et al., "Codon modification of T cell receptors allows enhanced functional expression in transgenic human T cells," *Clinical Immunology* 119:135-145, 2006.
Stromnes et al., "Re-adapting T cells for cancer therapy: from mouse models to clinical trials," *Immunol Rev.* 257(1):145-164, 2014. (34 pages).
Szymczak et al., "Correction of multi-gene deficiency in vivo using a single 'self-cleaving' 2A peptide-based retroviral vector," *Nature Biotechnology* 22(5):589-594, 2004.
Udyavar et al., "Subtle affinity-enhancing mutations in a MOG-specific TCR alter specificity and generate new self-reactivity," *J Immunol.* 182(7):4439-4447, 2009. (19 pages).
Verhoeyen et al., "Lentiviral Vector Gene Transfer into Human T Cells," *Methods in Molecular Biology* 506:97-114, 2009.
Wälchli et al., "A Practical Approach to T-Cell Receptor Cloning and Expression," *PLoS One* 6(11):e27930 2011, 11 pages.
Weber et al., "Class II-restricted T cell receptor engineered in vitro for higher affinity retains peptide specificity and function," *PNAS* 102(52):19033-19038, 2005.
Xu et al., "MHC/peptide tetramer-based studies of T cell function," *Journal of Immunological Methods* 268:21-28, 2002.
Zhang et al., "Transduction of Human T Cells with a Novel T-Cell Receptor Confers Anti-HCV Reactivity," *PLoS Pathogens* 6(7):e1001018, 2010, 13 pages.
Zhao et al., "High-Affinity TCRs Generated by Phage Display Provide $CD4^+$ T Cells with the Ability to Recognize and Kill Tumor Cell Lines," *J Immunol.* 179(9):5845-5854, 2007. (19 pages).
Zhao et al., "Primary Human Lymphocytes Transduced with NY-ESO-1 Antigen-Specific TCR Genes Recognize and Kill Diverse Human Tumor Cell Lines," *J Immunol.* 174(7):4415-4423, 2005. (25 pages).
Dossett, "Generation and Expression of High Affinity, Tumor Antigen-Specific Mouse and Human T Cell Receptors to Genetically Modify CD8+ T Cells for Adoptive Immunotherapy of Cancer," *A dissertation submitted in partial fulfillment of the requirements for the degree of Doctor of Philosophy, University of Washington*, 2006. (151 pages).
Axelsson-Robertson et al., "The immunological footprint of Mycobacterium tuberculosis T-cell epitope recognition," *J Infect Dis* 205(suppl2):S301-15, 2012. (Abstract Only).
Office Action, dated May 6, 2020, for Chinese Application No. 201710783710X, 9 pages. (w/ English Translation).
Office Action, dated May 1, 2020, for Indian Application No. 9787/DELNP/2014, 6 pages. (w/ English Translation).

* cited by examiner

Fig. 3A
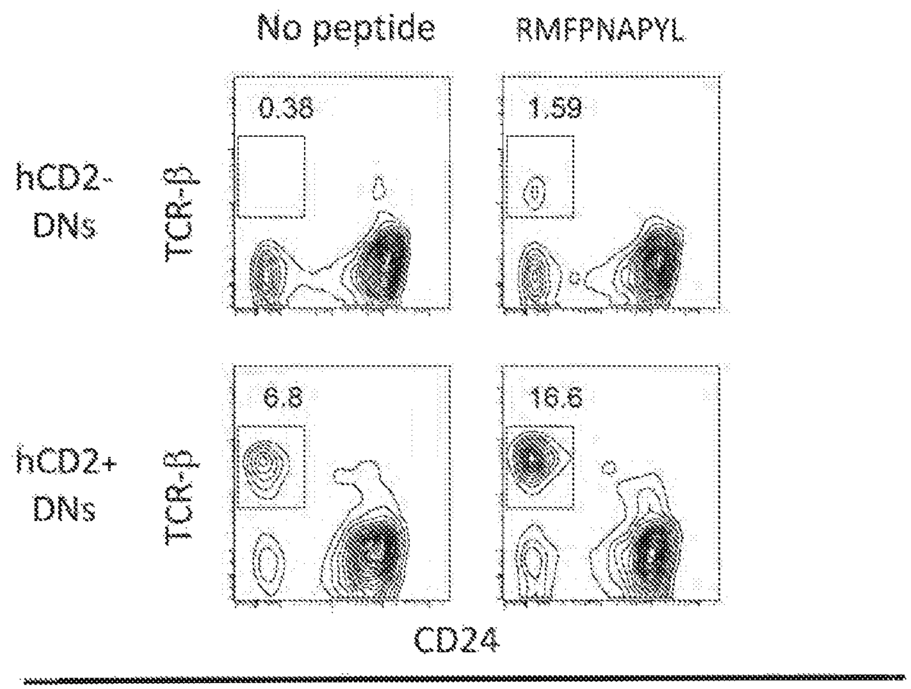
Fig. 3B
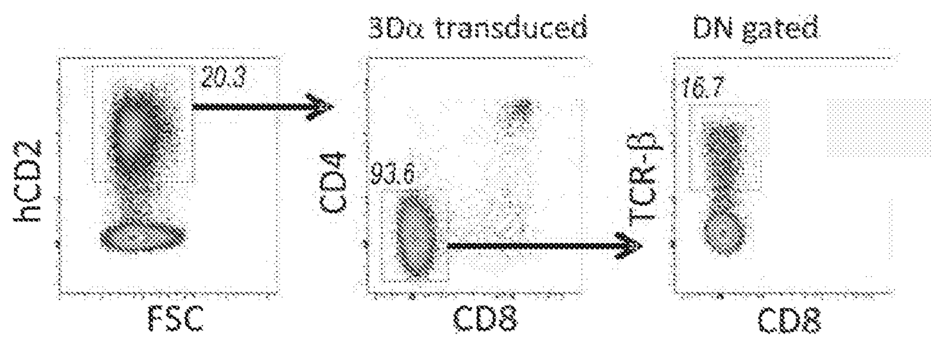
Fig. 3C
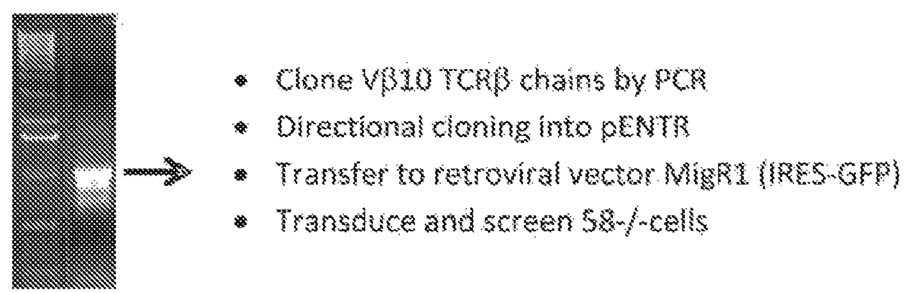
*Fig. 3*

| | 104 | 105 | 106 | 107 | 108 | 109 | 110 | 111 | 112 | 113 | 114 | 115 | 116 | 117 | 118 | |
|---|---|---|---|---|---|---|---|---|---|---|---|---|---|---|---|---|
| 3Dβ | C | A | S | S | P | G | L | G | G | S | Y | E | Q | Y | F | SEQ ID. NO: 32 |
| | tgt | gcc | agc | agc | cct | gga | ctg | ggg | gga | tcc | tat | gaa | cag | tac | ttc | SEQ ID. NO: 33 |
| Vβ10 clone#1 | C | A | S | S | Q | G | L | G | S | S | Y | E | Q | Y | F | SEQ ID. NO: 34 |
| | tgt | gcc | agc | agc | cag | gga | ctg | ggg | agc | tcc | tat | gaa | cag | tac | ttc | SEQ ID. NO: 35 |
| Vβ10 clone#2 | C | A | S | S | Y | I | L | | G | A | Y | E | Q | Y | F | SEQ ID. NO: 36 |
| | tgt | gcc | agc | agc | tat | ata | ctg | ... | ggg | gcc | tat | gaa | cag | tac | ttc | SEQ ID. NO: 37 |
| Vβ10 clone#3 | C | A | S | S | S | W | T | | | V | Y | E | Q | Y | F | SEQ ID. NO: 38 |
| | tgt | gcc | agc | agc | tcc | tgg | aca | ... | ... | gtc | tat | gaa | cag | tac | ttc | SEQ ID. NO: 39 |
| Vβ10 clone#4 | C | A | S | S | W | T | G | A | N | T | G | Q | L | Y | F | SEQ ID. NO: 40 |
| | tgt | gcc | agc | agc | tgg | aca | ggg | gca | aac | acc | ggg | cag | ctc | tac | ttt | SEQ ID. NO: 41 |

*Fig. 4B*

SEQUENCE LISTING

```
<160> NUMBER OF SEQ ID NOS: 53

<210> SEQ ID NO 1
<211> LENGTH: 8
<212> TYPE: PRT
<213> ORGANISM: Artificial Sequence
<220> FEATURE:
<223> OTHER INFORMATION: synthetic ovalbumin peptide

<400> SEQUENCE: 1

Ser Ile Ile Asn Phe Glu Lys Leu
1               5


<210> SEQ ID NO 2
<211> LENGTH: 9
<212> TYPE: PRT
<213> ORGANISM: Artificial Sequence
<220> FEATURE:
<223> OTHER INFORMATION: Synthetic WT1 peptide

<400> SEQUENCE: 2
```

```
Arg Met Phe Pro Asn Ala Pro Tyr Leu
1               5


<210> SEQ ID NO 3
<211> LENGTH: 3366
<212> TYPE: DNA
<213> ORGANISM: Homo sapiens

<400> SEQUENCE: 3

cgtgggattt ccagaccgcg gctttctaat cggctcggga ggaagctctg cagctctctt      60

gggaattaag ctcaatctct ggactctctc tctttctctt tctccccctc cctctcctgc     120

gaagaagctc aagacaaaac caggaagccg gcgaccctca cctcctcggg ggctgggagg     180

aaggaggaaa acgaaagtcg ccgccgccgc gctgtccccc gagagctgcc tttcctcggg     240

catccctggg gctgccgcgg gacctcgcag ggcggatata aagaaccgcg gccttgggaa     300

gaggcggaga ccggctttta aagaaagaag tcctgggtcc tgcggtctgg ggcgaggcaa     360

gggcgctttt ctgcccacgc tccccgtggc ccatcgatcc cccgcgcgtc cgccgctgtt     420

ctaaggagag aagtgggggc cccccaggct cgcgcgtgga gcgaagcagc atgggcagtc     480

ggtgcgcgct ggccctggcg gtgctctcgg ccttgctgtg tcaggtctgg agctctgggg     540

tgttcgaact gaagctgcag gagttcgtca acaagaaggg gctgctgggg aaccgcaact     600

gctgccgcgg gggcgcgggg ccaccgccgt gcgcctgccg gaccttcttc cgcgtgtgcc     660

tcaagcacta ccaggccagc gtgtcccccg agccgccctg cacctacggc agcgccgtca     720

cccccgtgct gggcgtcgac tccttcagtc tgcccgacgg cgggggcgcc gactccgcgt     780

tcagcaaccc catccgcttc cccttcggct tcacctggcc gggcaccttc tctctgatta     840

ttgaagctct ccacacagat tctcctgatg acctcgcaac agaaaaccca gaaagactca     900

tcagccgcct ggccacccag aggcacctga cggtgggcga ggagtggtcc caggacctgc     960

acagcagcgg ccgcacggac ctcaagtact cctaccgctt cgtgtgtgac gaacactact    1020

acggagaggg ctgctccgtt ttctgccgtc cccgggacga tgccttcggc cacttcacct    1080

gtggggagcg tggggagaaa gtgtgcaacc ctggctggaa agggccctac tgcacagagc    1140

cgatctgcct gcctggatgt gatgagcagc atggattttg tgacaaacca ggggaatgca    1200

agtgcagagt gggctggcag ggccggtact gtgacgagtg tatccgctat ccaggctgtc    1260

tccatggcac ctgccagcag ccctggcagt gcaactgcca ggaaggctgg gggggccttt    1320

tctgcaacca ggacctgaac tactgcacac accataagcc ctgcaagaat ggagccacct    1380

gcaccaacac gggccagggg agctacactt gctcttgccg gcctgggtac acaggtgcca    1440

cctgcgagct ggggattgac gagtgtgacc ccagcccttg taagaacgga gggagctgca    1500

cggatctcga gaacagctac tcctgtacct gcccacccgg cttctacggc aaaatctgtg    1560

aattgagtgc catgacctgt gcggacggcc cttgctttaa cgggggtcgg tgctcagaca    1620

gccccgatgg agggtacagc tgccgctgcc ccgtgggcta ctccggcttc aactgtgaga    1680

agaaaattga ctactgcagc tcttcaccct gttctaatgg tgccaagtgt gtggacctcg    1740

gtgatgccta cctgtgccgc tgccaggccg gcttctcggg gaggcactgt gacgacaacg    1800

tggacgactg cgcctcctcc ccgtgcgcca acgggggcac ctgccgggat ggcgtgaacg    1860

acttctcctg cacctgcccg cctggctaca cgggcaggaa ctgcagtgcc cccgtcagca    1920

ggtgcgagca cgcaccctgc cacaatgggg ccacctgcca cgagaggggc caccgctatg    1980

tgtgcgagtg tgcccgaggc tacgggggtc ccaactgcca gttcctgctc cccgagctgc    2040
```

```
ccccgggccc agcggtggtg gacctcactg agaagctaga gggccagggc gggccattcc   2100

cctgggtggc cgtgtgcgcc ggggtcatcc ttgtcctcat gctgctgctg ggctgtgccg   2160

ctgtggtggt ctgcgtccgg ctgaggctgc agaagcaccg gcccccagcc gacccctgcc   2220

ggggggagac ggagaccatg aacaacctgg ccaactgcca gcgtgagaag gacatctcag   2280

tcagcatcat cggggccacg cagatcaaga acaccaacaa gaaggcggac ttccacgggg   2340

accacagcgc cgacaagaat ggcttcaagg cccgctaccc agcggtggac tataacctcg   2400

tgcaggacct caagggtgac gacaccgccg tcagggacgc gcacagcaag cgtgacacca   2460

agtgccagcc ccagggctcc tcaggggagg agaaggggac cccgaccaca ctcaggggtg   2520

gagaagcatc tgaaagaaaa aggccggact cgggctgttc aacttcaaaa gacaccaagt   2580

accagtcggt gtacgtcata tccgaggaga aggatgagtg cgtcatagca actgaggtgt   2640

aaaatggaag tgagatggca agactcccgt ttctcttaaa ataagtaaaa ttccaaggat   2700

atatgcccca acgaatgctg ctgaagagga gggaggcctc gtggactgct gctgagaaac   2760

cgagttcaga ccgagcaggt tctcctcctg aggtcctcga cgcctgccga cagcctgtcg   2820

cggcccggcc gcctgcggca ctgccttccg tgacgtcgcc gttgcactat ggacagttgc   2880

tcttaagaga atatatattt aaatgggtga actgaattac gcataagaag catgcactgc   2940

ctgagtgtat attttggatt cttatgagcc agtcttttct tgaattagaa acacaaacac   3000

tgcctttatt gtccttttg atacgaagat gtgcttttc tagatggaaa agatgtgtgt   3060

tattttttgg atttgtaaaa atatttttca tgatatctgt aaagcttgag tattttgtga   3120

tgttcgtttt ttataattta aattttggta aatatgtaca aaggcacttc gggtctatgt   3180

gactatattt ttttgtatat aaatgtattt atggaatatt gtgcaaatgt tatttgagtt   3240

ttttactgtt ttgttaatga agaaattcct ttttaaaata tttttccaaa ataaatttta   3300

tgaatgacaa aaaaaaaaaa aaaaaaaaaa aaaaaaaaaa aaaaaaaaaa aaaaaaaaaa   3360

aaaaaa                                                              3366
```

<210> SEQ ID NO 4
<211> LENGTH: 723
<212> TYPE: PRT
<213> ORGANISM: Homo sapiens

<400> SEQUENCE: 4

```
Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ala Gly Pro Pro Pro Cys Ala Cys Arg Thr Phe Phe Arg Val Cys Leu
    50                  55                  60

Lys His Tyr Gln Ala Ser Val Ser Pro Glu Pro Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125
```

```
Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
    290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                325                 330                 335

Cys Lys Asn Gly Gly Ser Cys Thr Asp Leu Glu Asn Ser Tyr Ser Cys
            340                 345                 350

Thr Cys Pro Pro Gly Phe Tyr Gly Lys Ile Cys Glu Leu Ser Ala Met
        355                 360                 365

Thr Cys Ala Asp Gly Pro Cys Phe Asn Gly Gly Arg Cys Ser Asp Ser
    370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Ser Pro Cys Ser Asn
                405                 410                 415

Gly Ala Lys Cys Val Asp Leu Gly Asp Ala Tyr Leu Cys Arg Cys Gln
            420                 425                 430

Ala Gly Phe Ser Gly Arg His Cys Asp Asp Asn Val Asp Asp Cys Ala
        435                 440                 445

Ser Ser Pro Cys Ala Asn Gly Gly Thr Cys Arg Asp Gly Val Asn Asp
    450                 455                 460

Phe Ser Cys Thr Cys Pro Pro Gly Tyr Thr Gly Arg Asn Cys Ser Ala
465                 470                 475                 480

Pro Val Ser Arg Cys Glu His Ala Pro Cys His Asn Gly Ala Thr Cys
                485                 490                 495

His Glu Arg Gly His Arg Tyr Val Cys Glu Cys Ala Arg Gly Tyr Gly
            500                 505                 510

Gly Pro Asn Cys Gln Phe Leu Leu Pro Glu Leu Pro Pro Gly Pro Ala
        515                 520                 525

Val Val Asp Leu Thr Glu Lys Leu Glu Gly Gln Gly Gly Pro Phe Pro
    530                 535                 540

Trp Val Ala Val Cys Ala Gly Val Ile Leu Val Leu Met Leu Leu Leu
```

545 550 555 560

Gly Cys Ala Ala Val Val Val Cys Val Arg Leu Arg Leu Gln Lys His
565 570 575

Arg Pro Pro Ala Asp Pro Cys Arg Gly Glu Thr Glu Thr Met Asn Asn
580 585 590

Leu Ala Asn Cys Gln Arg Glu Lys Asp Ile Ser Val Ser Ile Ile Gly
595 600 605

Ala Thr Gln Ile Lys Asn Thr Asn Lys Lys Ala Asp Phe His Gly Asp
610 615 620

His Ser Ala Asp Lys Asn Gly Phe Lys Ala Arg Tyr Pro Ala Val Asp
625 630 635 640

Tyr Asn Leu Val Gln Asp Leu Lys Gly Asp Asp Thr Ala Val Arg Asp
645 650 655

Ala His Ser Lys Arg Asp Thr Lys Cys Gln Pro Gln Gly Ser Ser Gly
660 665 670

Glu Glu Lys Gly Thr Pro Thr Thr Leu Arg Gly Gly Glu Ala Ser Glu
675 680 685

Arg Lys Arg Pro Asp Ser Gly Cys Ser Thr Ser Lys Asp Thr Lys Tyr
690 695 700

Gln Ser Val Tyr Val Ile Ser Glu Glu Lys Asp Glu Cys Val Ile Ala
705 710 715 720

Thr Glu Val

<210> SEQ ID NO 5
<211> LENGTH: 3444
<212> TYPE: DNA
<213> ORGANISM: Mus musculus

<400> SEQUENCE: 5
cttggcgata gtgcaagaga taccggtcta gaacactctg ggagcggcag cggctgccga 60
gtgacgccgg gccgggaaac cagggcgcgc gccgcagtcc ttgccaccac cgttcccacc 120
gcgcccctcg gggccccgga ttatcgcctc accggtggga tttccagacc gccgcttcct 180
aataggcctg cgaaggaagc cactgcaagc tctcttggga attaagctga acatctgggc 240
tctcttccct ctgtgtctta tctcctttct cctctttccc tccgcgaaga agcttaagac 300
aaaaccagaa agcaggagac actcacctct ccgtggactg aaagccagac gaagaggaaa 360
ccgaaagttg tcctttctca gtgcctcgta gagctcttgc cggggaccta gctgaaggca 420
ccgcaccctc ctgaagcgac ctggccctga tagcacacct ggagccgaga gacgcctttc 480
cgccagtact cctcgggtca tatagacttt cctggcatcc ctgggtcttt gaagaagaaa 540
gaaaagagga tactctagga gagcaagggc gtccagcggt accatgggcc gtcggagcgc 600
gctagccctt gccgtggtct ctgccctgct gtgccaggtc tggagctccg gcgtatttga 660
gctgaagctg caggagttcg tcaacaagaa ggggctgctg gggaaccgca actgctgccg 720
cgggggctct ggcccgcctt gcgcctgcag gaccttcttt cgcgtatgcc tcaagcacta 780
ccaggccagc gtgtcaccgg agccaccctg cacctacggc agtgctgtca cgccagtgct 840
gggtgtcgac tccttcagcc tgcctgatgg cgcaggcatc gaccccgcct tcagcaaccc 900
catccgattc cccttcggct tcacctggcc aggtaccttc tctctgatca ttgaagccct 960
ccatacagac tctcccgatg acctcgcaac agaaaaccca gaaagactca tcagccgcct 1020
gaccacacag aggcacctca ctgtgggaga agaatggtct caggaccttc acagtagcgg 1080
ccgcacagac ctccggtact cttaccggtt tgtgtgtgac gagcactact acggagaagg 1140

-continued

```
ttgctctgtg ttctgccgac ctcgggatga cgcctttggc cacttcacct gcggggacag   1200
aggggagaag atgtgcgacc ctggctggaa aggccagtac tgcactgacc caatctgtct   1260
gccagggtgt gatgaccaac atggatactg tgacaaacca ggggagtgca agtgcagagt   1320
tggctggcag ggccgctact gcgatgagtg catccgatac ccaggttgtc tccatggcac   1380
ctgccagcaa ccctggcagt gtaactgcca ggaaggctgg gggggccttt tctgcaacca   1440
agacctgaac tactgtactc accataagcc gtgcaggaat ggagccacct gcaccaacac   1500
gggccagggg agctacacat gttcctgccg acctgggtat acaggtgcca actgtgagct   1560
ggaagtagat gagtgtgctc ctagcccctg caagaacgga gcgagctgca cggaccttga   1620
ggacagcttc tcttgcacct gccctcccgg cttctatggc aaggtctgtg agctgagcgc   1680
catgacctgt gcagatggcc cttgcttcaa tggaggacga tgttcagata accctgacgg   1740
aggctacacc tgccattgcc ccttgggctt ctctggcttc aactgtgaga agaagatgga   1800
tctctgcggc tcttcccctt gttctaacgg tgccaagtgt gtggacctcg gcaactctta   1860
cctgtgccgg tgccaggctg gcttctccgg gaggtactgc gaggacaatg tggatgactg   1920
tgcctcctcc ccgtgtgcaa atgggggcac ctgccgggac agtgtgaacg acttctcctg   1980
tacctgccca cctggctaca cgggcaagaa ctgcagcgcc cctgtcagca ggtgtgagca   2040
tgcaccctgc cataatgggg ccacctgcca ccagaggggc cagcgctaca tgtgtgagtg   2100
cgcccagggc tatggcggcc ccaactgcca gtttctgctc cctgagccac caccagggcc   2160
catggtggtg gacctcagtg agaggcatat ggagagccag ggcgggccct tcccctgggt   2220
ggccgtgtgt gccggggtgg tgcttgtcct cctgctgctg ctgggctgtg ctgctgtggt   2280
ggtctgcgtc cggctgaagc tacagaaaca ccagcctcca cctgaaccct gtgggggaga   2340
gacagaaacc atgaacaacc tagccaattg ccagcgcgag aaggacgttt ctgttagcat   2400
cattggggct acccagatca agaacaccaa caagaaggcg gactttcacg gggaccatgg   2460
agccgagaag agcagcttta aggtccgata ccccactgtg gactataacc tcgttcgaga   2520
cctcaaggga gatgaagcca cggtcaggga tacacacagc aaacgtgaca ccaagtgcca   2580
gtcacagagc tctgcaggag aagagaagat cgccccaaca cttaggggtg gggagattcc   2640
tgacagaaaa aggccagagt ctgtctactc tacttcaaag gacaccaagt accagtcggt   2700
gtatgttctg tctgcagaaa aggatgagtg tgttatagcg actgaggtgt aagatggaag   2760
cgatgtggca aaattcccat ttctcttaaa taaaattcca aggatatagc cccgatgaat   2820
gctgctgaga gaggaaggga gaggaaaccc agggactgct gctgagaacc aggttcaggc   2880
gaagctggtt ctctcagagt tagcagaggc gcccgacact gccagcctag gctttggctg   2940
ccgctggact gcctgctggt tgttcccatt gcactatgga cagttgcttt gaagagtata   3000
tatttaaatg gacgagtgac ttgattcata taggaagcac gcactgccca cacgtctatc   3060
ttggattact atgagccagt ctttccttga actagaaaca caactgcctt tattgtcctt   3120
tttgatactg agatgtgttt tttttttcc tagacgggaa aaagaaaacg tgtgttattt   3180
ttttgggatt tgtaaaaata tttttcatga tatctgtaaa gcttgagtat tttgtgacgt   3240
tcattttttt ataatttaaa ttttggtaaa tatgtacaaa ggcacttcgg gtctatgtga   3300
ctatattttt ttgtatataa atgtatttat ggaatattgt gcaaatgtta tttgagtttt   3360
ttactgtttt gttaatgaag aaattcattt taaaaatatt tttccaaaat aaatataatg   3420
aactacaaaa aaaaaaaaaa aaaa                                          3444
```

<210> SEQ ID NO 6
<211> LENGTH: 722
<212> TYPE: PRT
<213> ORGANISM: Mus musculus

<400> SEQUENCE: 6

```
Met Gly Arg Arg Ser Ala Leu Ala Leu Ala Val Val Ser Ala Leu Leu
1               5                   10                  15

Cys Gln Val Trp Ser Ser Gly Val Phe Glu Leu Lys Leu Gln Glu Phe
            20                  25                  30

Val Asn Lys Lys Gly Leu Leu Gly Asn Arg Asn Cys Cys Arg Gly Gly
        35                  40                  45

Ser Gly Pro Pro Cys Ala Cys Arg Thr Phe Phe Arg Val Cys Leu Lys
    50                  55                  60

His Tyr Gln Ala Ser Val Ser Pro Glu Pro Pro Cys Thr Tyr Gly Ser
65                  70                  75                  80

Ala Val Thr Pro Val Leu Gly Val Asp Ser Phe Ser Leu Pro Asp Gly
                85                  90                  95

Ala Gly Ile Asp Pro Ala Phe Ser Asn Pro Ile Arg Phe Pro Phe Gly
            100                 105                 110

Phe Thr Trp Pro Gly Thr Phe Ser Leu Ile Ile Glu Ala Leu His Thr
        115                 120                 125

Asp Ser Pro Asp Asp Leu Ala Thr Glu Asn Pro Glu Arg Leu Ile Ser
    130                 135                 140

Arg Leu Thr Thr Gln Arg His Leu Thr Val Gly Glu Glu Trp Ser Gln
145                 150                 155                 160

Asp Leu His Ser Ser Gly Arg Thr Asp Leu Arg Tyr Ser Tyr Arg Phe
                165                 170                 175

Val Cys Asp Glu His Tyr Tyr Gly Glu Gly Cys Ser Val Phe Cys Arg
            180                 185                 190

Pro Arg Asp Asp Ala Phe Gly His Phe Thr Cys Gly Asp Arg Gly Glu
        195                 200                 205

Lys Met Cys Asp Pro Gly Trp Lys Gly Gln Tyr Cys Thr Asp Pro Ile
    210                 215                 220

Cys Leu Pro Gly Cys Asp Asp Gln His Gly Tyr Cys Asp Lys Pro Gly
225                 230                 235                 240

Glu Cys Lys Cys Arg Val Gly Trp Gln Gly Arg Tyr Cys Asp Glu Cys
                245                 250                 255

Ile Arg Tyr Pro Gly Cys Leu His Gly Thr Cys Gln Gln Pro Trp Gln
            260                 265                 270

Cys Asn Cys Gln Glu Gly Trp Gly Gly Leu Phe Cys Asn Gln Asp Leu
        275                 280                 285

Asn Tyr Cys Thr His His Lys Pro Cys Arg Asn Gly Ala Thr Cys Thr
    290                 295                 300

Asn Thr Gly Gln Gly Ser Tyr Thr Cys Ser Cys Arg Pro Gly Tyr Thr
305                 310                 315                 320

Gly Ala Asn Cys Glu Leu Glu Val Asp Glu Cys Ala Pro Ser Pro Cys
                325                 330                 335

Lys Asn Gly Ala Ser Cys Thr Asp Leu Glu Asp Ser Phe Ser Cys Thr
            340                 345                 350

Cys Pro Pro Gly Phe Tyr Gly Lys Val Cys Glu Leu Ser Ala Met Thr
        355                 360                 365

Cys Ala Asp Gly Pro Cys Phe Asn Gly Gly Arg Cys Ser Asp Asn Pro
    370                 375                 380
```

```
Asp Gly Gly Tyr Thr Cys His Cys Pro Leu Gly Phe Ser Gly Phe Asn
385                 390                 395                 400

Cys Glu Lys Lys Met Asp Leu Cys Gly Ser Ser Pro Cys Ser Asn Gly
                405                 410                 415

Ala Lys Cys Val Asp Leu Gly Asn Ser Tyr Leu Cys Arg Cys Gln Ala
            420                 425                 430

Gly Phe Ser Gly Arg Tyr Cys Glu Asp Asn Val Asp Asp Cys Ala Ser
        435                 440                 445

Ser Pro Cys Ala Asn Gly Gly Thr Cys Arg Asp Ser Val Asn Asp Phe
    450                 455                 460

Ser Cys Thr Cys Pro Pro Gly Tyr Thr Gly Lys Asn Cys Ser Ala Pro
465                 470                 475                 480

Val Ser Arg Cys Glu His Ala Pro Cys His Asn Gly Ala Thr Cys His
                485                 490                 495

Gln Arg Gly Gln Arg Tyr Met Cys Glu Cys Ala Gln Gly Tyr Gly Gly
            500                 505                 510

Pro Asn Cys Gln Phe Leu Leu Pro Glu Pro Pro Pro Gly Pro Met Val
        515                 520                 525

Val Asp Leu Ser Glu Arg His Met Glu Ser Gln Gly Gly Pro Phe Pro
    530                 535                 540

Trp Val Ala Val Cys Ala Gly Val Val Leu Val Leu Leu Leu Leu Leu
545                 550                 555                 560

Gly Cys Ala Ala Val Val Val Cys Val Arg Leu Lys Leu Gln Lys His
                565                 570                 575

Gln Pro Pro Pro Glu Pro Cys Gly Gly Glu Thr Glu Thr Met Asn Asn
            580                 585                 590

Leu Ala Asn Cys Gln Arg Glu Lys Asp Val Ser Val Ser Ile Ile Gly
        595                 600                 605

Ala Thr Gln Ile Lys Asn Thr Asn Lys Lys Ala Asp Phe His Gly Asp
    610                 615                 620

His Gly Ala Glu Lys Ser Ser Phe Lys Val Arg Tyr Pro Thr Val Asp
625                 630                 635                 640

Tyr Asn Leu Val Arg Asp Leu Lys Gly Asp Glu Ala Thr Val Arg Asp
                645                 650                 655

Thr His Ser Lys Arg Asp Thr Lys Cys Gln Ser Gln Ser Ser Ala Gly
            660                 665                 670

Glu Glu Lys Ile Ala Pro Thr Leu Arg Gly Gly Glu Ile Pro Asp Arg
        675                 680                 685

Lys Arg Pro Glu Ser Val Tyr Ser Thr Ser Lys Asp Thr Lys Tyr Gln
    690                 695                 700

Ser Val Tyr Val Leu Ser Ala Glu Lys Asp Glu Cys Val Ile Ala Thr
705                 710                 715                 720

Glu Val


<210> SEQ ID NO 7
<211> LENGTH: 3420
<212> TYPE: DNA
<213> ORGANISM: Homo sapiens

<400> SEQUENCE: 7

aggtttcagt agcggcgctg cgcgcaggcc gggaacacga ggccaagagc cgcagcccca      60

gccgccttgg tgcagcgtac accggcacta gcccgcttgc agccccagga ttagacagaa     120

gacgcgtcct cggcgcggtc gccgcccagc cgtagtcacc tggattacct acagcggcag     180
```

```
ctgcagcgga gccagcgaga aggccaaagg ggagcagcgt cccgagagga gcgcctcttt    240
tcagggaccc cgccggctgg cggacgcgcg ggaaagcggc gtcgcgaaca gagccagatt    300
gagggcccgc gggtggagag agcgacgccc gaggggatgg cggcagcgtc ccggagcgcc    360
tctggctggg cgctactgct gctggtggca ctttggcagc agcgcgcggc cggctccggc    420
gtcttccagc tgcagctgca ggagttcatc aacgagcgcg gcgtactggc cagtgggcgg    480
ccttgcgagc ccggctgccg gactttcttc cgcgtctgcc ttaagcactt ccaggcggtc    540
gtctcgcccg gaccctgcac cttcgggacc gtctccacgc cggtattggg caccaactcc    600
ttcgctgtcc gggacgacag tagcggcggg gggcgcaacc ctctccaact gcccttcaat    660
ttcacctggc cgggtacctt ctcgctcatc atcgaagctt ggcacgcgcc aggagacgac    720
ctgcggccag aggccttgcc accagatgca ctcatcagca agatcgccat ccagggctcc    780
ctagctgtgg gtcagaactg gttattggat gagcaaacca gcaccctcac aaggctgcgc    840
tactcttacc gggtcatctg cagtgacaac tactatggag acaactgctc ccgcctgtgc    900
aagaagcgca atgaccactt cggccactat gtgtgccagc cagatggcaa cttgtcctgc    960
ctgcccggtt ggactgggga atattgccaa cagcctatct gtctttcggg ctgtcatgaa   1020
cagaatggct actgcagcaa gccagcagag tgcctctgcc gcccaggctg gcagggccgg   1080
ctgtgtaacg aatgcatccc ccacaatggc tgtcgccacg gcacctgcag cactccctgg   1140
caatgtactt gtgatgaggg ctggggaggc ctgttttgtg accaagatct caactactgc   1200
acccaccact ccccatgcaa gaatggggca acgtgctcca acagtgggca gcgaagctac   1260
acctgcacct gtcgcccagg ctacactggt gtggactgtg agctggagct cagcgagtgt   1320
gacagcaacc cctgtcgcaa tggaggcagc tgtaaggacc aggaggatgg ctaccactgc   1380
ctgtgtcctc cgggctacta tggcctgcat tgtgaacaca gcaccttgag ctgcgccgac   1440
tccccctgct tcaatggggg ctcctgccgg gagcgcaacc aggggggccaa ctatgcttgt   1500
gaatgtcccc ccaacttcac cggctccaac tgcgagaaga aagtggacag gtgcaccagc   1560
aacccctgtg ccaacggggg acagtgcctg aaccgaggtc caagccgcat gtgccgctgc   1620
cgtcctggat tcacgggcac ctactgtgaa ctccacgtca gcgactgtgc ccgtaaccct   1680
tgcgcccacg gtggcacttg ccatgacctg gagaatgggc tcatgtgcac ctgccctgcc   1740
ggcttctctg gccgacgctg tgaggtgcgg acatccatcg atgcctgtgc ctcgagtccc   1800
tgcttcaaca gggccacctg ctacaccgac ctctccacag acacctttgt gtgcaactgc   1860
ccttatggct ttgtgggcag ccgctgcgag ttccccgtgg gcttgccgcc cagcttcccc   1920
tgggtggccg tctcgctggg tgtggggctg gcagtgctgc tggtactgct gggcatggtg   1980
gcagtggctg tgcggcagct gcggcttcga cggccggacg acggcagcag ggaagccatg   2040
aacaacttgt cggacttcca gaaggacaac ctgattcctg ccgcccagct taaaaacaca   2100
aaccagaaga aggagctgga agtggactgt ggcctggaca agtccaactg tggcaaacag   2160
caaaaccaca cattggacta taatctggcc ccagggcccc tggggcgggg gaccatgcca   2220
ggaaagtttc cccacagtga caagagctta ggagagaagg cgccactgcg gttacacagt   2280
gaaaagccag agtgtcggat atcagcgata tgctccccca gggactccat gtaccagtct   2340
gtgtgtttga tatcagagga gaggaatgaa tgtgtcattg ccacggaggt ataaggcagg   2400
agcctacctg gacatccctg ctcagccccg cggctggacc ttccttctgc attgtttaca   2460
ttgcatcctg gatgggacgt ttttcatatg caacgtgctg ctctcaggag gaggagggaa   2520
```

```
tggcaggaac cggacagact gtgaacttgc caagagatgc aatacccttc cacacctttg   2580

ggtgtctgtc tggcatcaga ttggcagctg caccaaccag aggaacagaa gagaagagag   2640

atgccactgg gcactgccct gccagtagtg gccttcaggg ggctccttcc ggggctccgg   2700

cctgttttcc agagagagtg gcagtagccc catggggccc ggagctgctg tggcctccac   2760

tggcatccgt gtttccaaaa gtgcctttgg cccaggctcc acggcgacag ttgggcccaa   2820

atcagaaagg agagaggggg ccaatgaggg cagggcctcc tgtgggctgg aaaaccactg   2880

ggtgcgtctc ttgctggggt ttgccctgga ggtgaggtga gtgctcgagg gaggggagtg   2940

ctttctgccc catgcctcca actactgtat gcaggcctgg ctctctggtc taggcccttt   3000

gggcaagaat gtccgtctac ccggcttcca ccaccctctg gccctgggct tctgtaagca   3060

gacaggcaga gggcctgccc ctcccaccag ccaagggtgc caggcctaac tggggcactc   3120

agggcagtgt gttggaaatt ccactgaggg ggaaatcagg tgctgcggcc gcctgggccc   3180

tttcctccct caagcccatc tccacaacct cgagcctggg ctctggtcca ctactgcccc   3240

agaccaccct caaagctggt cttcagaaat caataatatg agtttttatt ttgttttttt   3300

ttttttttt gtagtttatt ttggagtcta gtatttcaat aatttaagaa tcagaagcac   3360

tgacctttct acattttata acattatttt gtatataatg tgtatttata atatgaaaca   3420
```

<210> SEQ ID NO 8
<211> LENGTH: 685
<212> TYPE: PRT
<213> ORGANISM: Homo sapiens

<400> SEQUENCE: 8

```
Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220
```

```
Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
                325                 330                 335

Gly Ser Cys Lys Asp Gln Glu Asp Gly Tyr His Cys Leu Cys Pro Pro
            340                 345                 350

Gly Tyr Tyr Gly Leu His Cys Glu His Ser Thr Leu Ser Cys Ala Asp
        355                 360                 365

Ser Pro Cys Phe Asn Gly Gly Ser Cys Arg Glu Arg Asn Gln Gly Ala
    370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
        435                 440                 445

Cys Ala His Gly Gly Thr Cys His Asp Leu Glu Asn Gly Leu Met Cys
    450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
        515                 520                 525

Trp Val Ala Val Ser Leu Gly Val Gly Leu Ala Val Leu Leu Val Leu
    530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
        595                 600                 605

Gln Asn His Thr Leu Asp Tyr Asn Leu Ala Pro Gly Pro Leu Gly Arg
    610                 615                 620

Gly Thr Met Pro Gly Lys Phe Pro His Ser Asp Lys Ser Leu Gly Glu
625                 630                 635                 640
```

```
Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
        675                 680                 685


<210> SEQ ID NO 9
<211> LENGTH: 3451
<212> TYPE: DNA
<213> ORGANISM: Mus musculus

<400> SEQUENCE: 9

atataagaaa ggctctggag caagcaggtt tcagtagcgg cgctgctcgc aggctaggaa     60

cccgaggcca agagctgcag ccaaagtcac ttgggtgcag tgtactccct cactagcccg    120

ctcgagaccc taggatttgc tccaggacac gtacttagag cagccaccgc ccagtcgccc    180

tcacctggat tacctaccga ggcatcgagc agcggagttt ttgagaaggc gacaagggag    240

cagcgtcccg aggggaatca gcttttcagg aactcggctg gcagacggga cttgcgggag    300

agcgacatcc ctaacaagca gattcggagt cccggagtgg agaggacacc ccaagggatg    360

acgcctgcgt cccggagcgc ctgtcgctgg gcgctactgc tgctggcggt actgtggccg    420

cagcagcgcg ctgcgggctc cggcatcttc cagctgcggc tgcaggagtt cgtcaaccag    480

cgcggtatgc tggccaatgg gcagtcctgc gaaccgggct gccggacttt cttccgcatc    540

tgccttaagc acttccaggc aaccttctcc gagggaccct gcacctttgg caatgtctcc    600

acgccggtat tgggcaccaa ctccttcgtc gtcagggaca agaatagcgg cagtggtcgc    660

aaccctctgc agttgccctt caatttcacc tggccgggaa ccttctcact caacatccaa    720

gcttggcaca caccgggaga cgacctgcgg ccagagactt cgccaggaaa ctctctcatc    780

agccaaatca tcatccaagg ctctcttgct gtgggtaaga tttggcgaac agacgagcaa    840

aatgacaccc tcaccagact gagctactct taccgggtca tctgcagtga caactactat    900

ggagagagct gttctcgcct atgcaagaag cgcgatgacc acttcggaca ttatgagtgc    960

cagccagatg gcagcctgtc ctgcctgccg ggctggactg ggaagtactg tgaccagcct   1020

atatgtcttt ctggctgtca tgagcagaat ggttactgca gcaagccaga tgagtgcatc   1080

tgccgtccag gttggcaggg tcgcctgtgc aatgaatgta tcccccacaa tggctgtcgt   1140

catggcacct gcagcatccc ctggcagtgt gcctgcgatg agggatgggg aggtctgttt   1200

tgtgaccaag atctcaacta ctgtactcac cactctccgt gcaagaatgg atcaacgtgt   1260

tccaacagtg ggccaaaggg ttatacctgc acctgtctcc caggctacac tggtgagcac   1320

tgtgagctgg gactcagcaa gtgtgccagc aacccctgtc gaaatggtgg cagctgtaag   1380

gaccaggaga atagctacca ctgcctgtgt cccccaggct actatggcca gcactgtgag   1440

catagtacct tgacctgcgc ggactcaccc tgcttcaatg gggctcttg ccgggagcgc    1500

aaccaggggt ccagttatgc ctgcgaatgc ccccccaact ttaccggctc taactgtgag   1560

aagaaagtag acaggtgtac cagcaacccg tgtgccaatg gaggccagtg ccagaacaga   1620

ggtccaagcc gaacctgccg ctgccggcct ggattcacag gcacccactg tgaactgcac   1680

atcagcgatt gtgcccgaag tccctgtgcc cacgggggca cttgccacga tctggagaat   1740

gggcctgtgt gcacctgccc cgctggcttc tctggaaggc gctgcgaggt gcggataacc   1800

cacgatgcct gtgcctccgg accctgcttc aatggggcca cctgctacac tggcctctcc   1860
```

```
ccaaacaact tcgtctgcaa ctgtccttat ggctttgtgg gcagccgctg cgagtttccc   1920

gtgggcttgc cacccagctt cccctgggta gctgtctcgc tgggcgtggg gctagtggta   1980

ctgctggtgc tcctggtcat ggtggtagtg gctgtgcggc agctgcggct tcggaggccc   2040

gatgacgaga gcagggaagc catgaacaat ctgtcagact tccagaagga caacctaatc   2100

cctgccgccc agctcaaaaa cacaaaccag aagaaggagc tggaagtgga ctgtggtctg   2160

gacaagtcca attgtggcaa actgcagaac cacacattgg actacaatct agccccggga   2220

ctcctaggac ggggcggcat gcctgggaag tatcctcaca gtgacaagag cttaggagag   2280

aaggtgccac ttcggttaca cagtgagaag ccagagtgtc gaatatcagc catttgctct   2340

cccagggact ctatgtacca atcagtgtgt ttgatatcag aagagaggaa cgagtgtgtg   2400

attgccacag aggtataagg caggagccta ctcagacacc cagctccggc ccagcagctg   2460

ggccttcctt ctgcattgtt tacattgcat cctgtatggg acatctttag tatgcacagt   2520

gctgctctgc ggaggaggag gaaatggcat gaactgaaca gactgtgaac ccgccaagag   2580

tcgcaccggc tctgcacacc tccaggagtc tgcctggctt cagatgggca gccccgccaa   2640

gggaacagag ttgaggagtt agaggagcat cagttgagct gatatctaag gtgcctctcg   2700

aacttggact tgctctgcca acagtggtca tcatggagct cttgactgtt ctccagagag   2760

tggcagtggc cctagtgggt cttggcgctg ctgtagctcc tgtgggcatc tgtatttcca   2820

aagtgccttt gcccagactc catcctcaca gctgggccca aatgagaaag cagagaggag   2880

gcttgcaaag gataggcctc ccgcaggcag aacagccttg gagtttggca ttaagcagga   2940

gctactctgc aggtgaggaa agcccgagga ggggacacgt gtgactcctg cctccaaccc   3000

cagtaggtgg agtgccacct gtagcctcta ggcaagagtt ggtccttccc ctggtcctgg   3060

tgcctctggg ctcatgtgaa cagatgggct tagggcacgc ccctttttgcc agccaggggt  3120

acaggcctca ctggggagct cagggccttc atgctaaact cccaataagg gagatggggg   3180

gaagggggct gtggcctagg cccttccctc cctcacaccc atttctgggc ccttgagcct   3240

gggctccacc agtgcccact gctgccccga gaccaacctt gaagccgatc ttcaaaaatc   3300

aataatatga ggttttgttt tgtagtttat tttggaatct agtattttga taatttaaga   3360

atcagaagca ctggcctttc tacattttat aacattattt tgtatataat gtgtatttat   3420

aatatgaaac agatgtgtac aggaatttat t                                  3451
```

```
<210> SEQ ID NO 10
<211> LENGTH: 686
<212> TYPE: PRT
<213> ORGANISM: Mus musculus

<400> SEQUENCE: 10

Met Thr Pro Ala Ser Arg Ser Ala Cys Arg Trp Ala Leu Leu Leu Leu
1               5                   10                  15

Ala Val Leu Trp Pro Gln Gln Arg Ala Ala Gly Ser Gly Ile Phe Gln
            20                  25                  30

Leu Arg Leu Gln Glu Phe Val Asn Gln Arg Gly Met Leu Ala Asn Gly
        35                  40                  45

Gln Ser Cys Glu Pro Gly Cys Arg Thr Phe Phe Arg Ile Cys Leu Lys
    50                  55                  60

His Phe Gln Ala Thr Phe Ser Glu Gly Pro Cys Thr Phe Gly Asn Val
65                  70                  75                  80

Ser Thr Pro Val Leu Gly Thr Asn Ser Phe Val Val Arg Asp Lys Asn
                85                  90                  95
```

```
Ser Gly Ser Gly Arg Asn Pro Leu Gln Leu Pro Phe Asn Phe Thr Trp
            100                 105                 110

Pro Gly Thr Phe Ser Leu Asn Ile Gln Ala Trp His Thr Pro Gly Asp
        115                 120                 125

Asp Leu Arg Pro Glu Thr Ser Pro Gly Asn Ser Leu Ile Ser Gln Ile
    130                 135                 140

Ile Ile Gln Gly Ser Leu Ala Val Gly Lys Ile Trp Arg Thr Asp Glu
145                 150                 155                 160

Gln Asn Asp Thr Leu Thr Arg Leu Ser Tyr Ser Tyr Arg Val Ile Cys
                165                 170                 175

Ser Asp Asn Tyr Tyr Gly Glu Ser Cys Ser Arg Leu Cys Lys Lys Arg
            180                 185                 190

Asp Asp His Phe Gly His Tyr Glu Cys Gln Pro Asp Gly Ser Leu Ser
        195                 200                 205

Cys Leu Pro Gly Trp Thr Gly Lys Tyr Cys Asp Gln Pro Ile Cys Leu
    210                 215                 220

Ser Gly Cys His Glu Gln Asn Gly Tyr Cys Ser Lys Pro Asp Glu Cys
225                 230                 235                 240

Ile Cys Arg Pro Gly Trp Gln Gly Arg Leu Cys Asn Glu Cys Ile Pro
                245                 250                 255

His Asn Gly Cys Arg His Gly Thr Cys Ser Ile Pro Trp Gln Cys Ala
            260                 265                 270

Cys Asp Glu Gly Trp Gly Gly Leu Phe Cys Asp Gln Asp Leu Asn Tyr
        275                 280                 285

Cys Thr His His Ser Pro Cys Lys Asn Gly Ser Thr Cys Ser Asn Ser
    290                 295                 300

Gly Pro Lys Gly Tyr Thr Cys Thr Cys Leu Pro Gly Tyr Thr Gly Glu
305                 310                 315                 320

His Cys Glu Leu Gly Leu Ser Lys Cys Ala Ser Asn Pro Cys Arg Asn
                325                 330                 335

Gly Gly Ser Cys Lys Asp Gln Glu Asn Ser Tyr His Cys Leu Cys Pro
            340                 345                 350

Pro Gly Tyr Tyr Gly Gln His Cys Glu His Ser Thr Leu Thr Cys Ala
        355                 360                 365

Asp Ser Pro Cys Phe Asn Gly Gly Ser Cys Arg Glu Arg Asn Gln Gly
    370                 375                 380

Ser Ser Tyr Ala Cys Glu Cys Pro Pro Asn Phe Thr Gly Ser Asn Cys
385                 390                 395                 400

Glu Lys Lys Val Asp Arg Cys Thr Ser Asn Pro Cys Ala Asn Gly Gly
                405                 410                 415

Gln Cys Gln Asn Arg Gly Pro Ser Arg Thr Cys Arg Cys Arg Pro Gly
            420                 425                 430

Phe Thr Gly Thr His Cys Glu Leu His Ile Ser Asp Cys Ala Arg Ser
        435                 440                 445

Pro Cys Ala His Gly Gly Thr Cys His Asp Leu Glu Asn Gly Pro Val
    450                 455                 460

Cys Thr Cys Pro Ala Gly Phe Ser Gly Arg Arg Cys Glu Val Arg Ile
465                 470                 475                 480

Thr His Asp Ala Cys Ala Ser Gly Pro Cys Phe Asn Gly Ala Thr Cys
                485                 490                 495

Tyr Thr Gly Leu Ser Pro Asn Asn Phe Val Cys Asn Cys Pro Tyr Gly
            500                 505                 510
```

```
Phe Val Gly Ser Arg Cys Glu Phe Pro Val Gly Leu Pro Pro Ser Phe
        515                 520                 525

Pro Trp Val Ala Val Ser Leu Gly Val Gly Leu Val Val Leu Leu Val
    530                 535                 540

Leu Leu Val Met Val Val Val Ala Val Arg Gln Leu Arg Leu Arg Arg
545                 550                 555                 560

Pro Asp Asp Glu Ser Arg Glu Ala Met Asn Asn Leu Ser Asp Phe Gln
                565                 570                 575

Lys Asp Asn Leu Ile Pro Ala Ala Gln Leu Lys Asn Thr Asn Gln Lys
            580                 585                 590

Lys Glu Leu Glu Val Asp Cys Gly Leu Asp Lys Ser Asn Cys Gly Lys
        595                 600                 605

Leu Gln Asn His Thr Leu Asp Tyr Asn Leu Ala Pro Gly Leu Leu Gly
    610                 615                 620

Arg Gly Gly Met Pro Gly Lys Tyr Pro His Ser Asp Lys Ser Leu Gly
625                 630                 635                 640

Glu Lys Val Pro Leu Arg Leu His Ser Glu Lys Pro Glu Cys Arg Ile
                645                 650                 655

Ser Ala Ile Cys Ser Pro Arg Asp Ser Met Tyr Gln Ser Val Cys Leu
            660                 665                 670

Ile Ser Glu Glu Arg Asn Glu Cys Val Ile Ala Thr Glu Val
        675                 680                 685


<210> SEQ ID NO 11
<211> LENGTH: 2977
<212> TYPE: DNA
<213> ORGANISM: Homo sapiens

<400> SEQUENCE: 11

agctggggta aggagttcaa ggcagcgccc acacccgggg gctctccgca acccgaccgc      60

ctgtccgctc ccccacttcc cgccctccct cccacctact cattcaccca cccacccacc     120

cagagccggg acggcagccc aggcgcccgg gccccgccgt ctcctcgccg cgatcctgga     180

cttcctcttg ctgcaggacc cggcttccac gtgtgtcccg gagccggcgt ctcagcacac     240

gctccgctcc gggcctgggt gcctacagca gccagagcag cagggagtcc gggacccggg     300

cggcatctgg gccaagttag gcgccgccga ggccagcgct gaacgtctcc agggccggag     360

gagccgcggg gcgtccgggt ctgagccgca gcaaatgggc tccgacgtgc gggacctgaa     420

cgcgctgctg cccgccgtcc cctccctggg tggcggcggc ggctgtgccc tgcctgtgag     480

cggcgcggcg cagtgggcgc cggtgctgga ctttgcgccc ccgggcgctt cggcttacgg     540

gtcgttgggc ggccccgcgc cgccaccggc tccgccgcca cccccgccgc cgccgcctca     600

ctccttcatc aaacaggagc cgagctgggg cggcgcggag ccgcacgagg agcagtgcct     660

gagcgccttc actgtccact ttcccggcca gttcactggc acagccggag cctgtcgcta     720

cgggcccttc ggtcctcctc cgcccagcca ggcgtcatcc ggccaggcca ggatgtttcc     780

taacgcgccc tacctgccca gctgcctcga gagccagccc gctattcgca atcagggtta     840

cagcacggtc accttcgacg ggacgcccag ctacggtcac acgccctcgc accatgcggc     900

gcagttcccc aaccactcat tcaagcatga ggatcccatg ggccagcagg gctcgctggg     960

tgagcagcag tactcggtgc cgcccccggt ctatggctgc cacaccccca ccgacagctg    1020

caccggcagc caggctttgc tgctgaggac gccctacagc agtgacaatt tataccaaat    1080

gacatcccag cttgaatgca tgacctggaa tcagatgaac ttaggagcca ccttaaaggg    1140
```

```
ccacagcaca gggtacgaga gcgataacca cacaacgccc atcctctgcg gagcccaata   1200
cagaatacac acgcacggtg tcttcagagg cattcaggat gtgcgacgtg tgcctggagt   1260
agccccgact cttgtacggt cggcatctga gaccagtgag aaacgcccct tcatgtgtgc   1320
ttacccaggc tgcaataaga gatattttaa gctgtcccac ttacagatgc acagcaggaa   1380
gcacactggt gagaaaccat accagtgtga cttcaaggac tgtgaacgaa ggttttctcg   1440
ttcagaccag ctcaaaagac accaaaggag acatacaggt gtgaaaccat tccagtgtaa   1500
aacttgtcag cgaaagttct cccggtccga ccacctgaag acccacacca ggactcatac   1560
aggtgaaaag cccttcagct gtcggtggcc aagttgtcag aaaaagtttg cccggtcaga   1620
tgaattagtc cgccatcaca acatgcatca gagaaacatg accaaactcc agctggcgct   1680
ttgaggggtc tccctcgggg accgttcagt gtcccaggca gcacagtgtg tgaactgctt   1740
tcaagtctga ctctccactc ctcctcacta aaaaggaaac ttcagttgat cttcttcatc   1800
caacttccaa gacaagatac cggtgcttct ggaaactacc aggtgtgcct ggaagagttg   1860
gtctctgccc tgcctacttt tagttgactc acaggccctg gagaagcagc taacaatgtc   1920
tggttagtta aaagcccatt gccatttggt gtggattttc tactgtaaga agagccatag   1980
ctgatcatgt ccccctgacc cttcccttct ttttttatgc tcgttttcgc tggggatgga   2040
attattgtac cattttctat catggaatat ttataggcca gggcatgtgt atgtgtctgc   2100
taatgtaaac tttgtcatgg tttccattta ctaacagcaa cagcaagaaa taaatcagag   2160
agcaaggcat cgggggtgaa tcttgtctaa cattcccgag gtcagccagg ctgctaacct   2220
ggaaagcagg atgtagttct gccaggcaac ttttaaagct catgcatttc aagcagctga   2280
agaaaaaatc agaactaacc agtacctctg tatagaaatc taaaagaatt ttaccattca   2340
gttaattcaa tgtgaacact ggcacactgc tcttaagaaa ctatgaagat ctgagatttt   2400
tttgtgtatg tttttgactc ttttgagtgg taatcatatg tgtctttata gatgtacata   2460
cctccttgca caaatggagg ggaattcatt ttcatcactg ggagtgtcct tagtgtataa   2520
aaaccatgct ggtatatggc ttcaagttgt aaaaatgaaa gtgactttaa aagaaaatag   2580
gggatggtcc aggatctcca ctgataagac tgtttttaag taacttaagg acctttgggt   2640
ctacaagtat atgtgaaaaa aatgagactt actgggtgag gaaatccatt gtttaaagat   2700
ggtcgtgtgt gtgtgtgtgt gtgtgtgtgt gtgtgtgttg tgttgtgttt tgttttttaa   2760
gggagggaat ttattattta ccgttgcttg aaattactgt gtaaatatat gtctgataat   2820
gatttgctct ttgacaacta aaattaggac tgtataagta ctagatgcat cactgggtgt   2880
tgatcttaca agatattgat gataacactt aaaattgtaa cctgcatttt tcactttgct   2940
ctcaattaaa gtctattcaa aaggaaaaaa aaaaaaa                            2977
```

```
<210> SEQ ID NO 12
<211> LENGTH: 497
<212> TYPE: PRT
<213> ORGANISM: Homo sapiens

<400> SEQUENCE: 12

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45
```

```
Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
        115                 120                 125

Pro Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly His Ser Thr
305                 310                 315                 320

Gly Tyr Glu Ser Asp Asn His Thr Thr Pro Ile Leu Cys Gly Ala Gln
                325                 330                 335

Tyr Arg Ile His Thr His Gly Val Phe Arg Gly Ile Gln Asp Val Arg
            340                 345                 350

Arg Val Pro Gly Val Ala Pro Thr Leu Val Arg Ser Ala Ser Glu Thr
        355                 360                 365

Ser Glu Lys Arg Pro Phe Met Cys Ala Tyr Pro Gly Cys Asn Lys Arg
    370                 375                 380

Tyr Phe Lys Leu Ser His Leu Gln Met His Ser Arg Lys His Thr Gly
385                 390                 395                 400

Glu Lys Pro Tyr Gln Cys Asp Phe Lys Asp Cys Glu Arg Arg Phe Ser
                405                 410                 415

Arg Ser Asp Gln Leu Lys Arg His Gln Arg Arg His Thr Gly Val Lys
            420                 425                 430

Pro Phe Gln Cys Lys Thr Cys Gln Arg Lys Phe Ser Arg Ser Asp His
        435                 440                 445

Leu Lys Thr His Thr Arg Thr His Thr Gly Glu Lys Pro Phe Ser Cys
    450                 455                 460

Arg Trp Pro Ser Cys Gln Lys Lys Phe Ala Arg Ser Asp Glu Leu Val
```

```
465                 470                 475                 480

Arg His His Asn Met His Gln Arg Asn Met Thr Lys Leu Gln Leu Ala
                485                 490                 495

Leu


<210> SEQ ID NO 13
<211> LENGTH: 3028
<212> TYPE: DNA
<213> ORGANISM: Homo sapiens

<400> SEQUENCE: 13

agctggggta aggagttcaa ggcagcgccc acacccgggg gctctccgca acccgaccgc      60

ctgtccgctc ccccacttcc cgccctccct cccacctact cattcaccca cccacccacc     120

cagagccggg acggcagccc aggcgcccgg gccccgccgt ctcctcgccg cgatcctgga     180

cttcctcttg ctgcaggacc cggcttccac gtgtgtcccg gagccggcgt ctcagcacac     240

gctccgctcc gggcctgggt gcctacagca gccagagcag cagggagtcc gggacccggg     300

cggcatctgg gccaagttag gcgccgccga ggccagcgct gaacgtctcc agggccggag     360

gagccgcggg gcgtccgggt ctgagccgca gcaaatgggc tccgacgtgc gggacctgaa     420

cgcgctgctg cccgccgtcc cctccctggg tggcggcggc ggctgtgccc tgcctgtgag     480

cggcgcggcg cagtgggcgc cggtgctgga ctttgcgccc ccgggcgctt cggcttacgg     540

gtcgttgggc ggccccgcgc cgccaccggc tccgccgcca cccccgccgc cgccgcctca     600

ctccttcatc aaacaggagc cgagctgggg cggcgcggag ccgcacgagg agcagtgcct     660

gagcgccttc actgtccact tttccggcca gttcactggc acagccggag cctgtcgcta     720

cgggcccttc ggtcctcctc cgcccagcca ggcgtcatcc ggccaggcca ggatgtttcc     780

taacgcgccc tacctgccca gctgcctcga gagccagccc gctattcgca atcagggtta     840

cagcacggtc accttcgacg ggacgcccag ctacggtcac acgccctcgc accatgcggc     900

gcagttcccc aaccactcat tcaagcatga ggatcccatg ggccagcagg gctcgctggg     960

tgagcagcag tactcggtgc cgcccccggt ctatggctgc cacaccccca ccgacagctg    1020

caccggcagc caggctttgc tgctgaggac gccctacagc agtgacaatt tataccaaat    1080

gacatcccag cttgaatgca tgacctggaa tcagatgaac ttaggagcca ccttaaaggg    1140

agttgctgct gggagctcca gctcagtgaa atggacagaa gggcagagca accacagcac    1200

agggtacgag agcgataacc acacaacgcc catcctctgc ggagcccaat acagaataca    1260

cacgcacggt gtcttcagag gcattcagga tgtgcgacgt gtgcctggag tagccccgac    1320

tcttgtacgg tcggcatctg agaccagtga gaaacgcccc ttcatgtgtg cttacccagg    1380

ctgcaataag agatatttta agctgtccca cttacagatg cacagcagga agcacactgg    1440

tgagaaacca taccagtgtg acttcaagga ctgtgaacga aggttttctc gttcagacca    1500

gctcaaaaga caccaaagga gacatacagg tgtgaaacca ttccagtgta aaacttgtca    1560

gcgaaagttc tcccggtccg accacctgaa gacccacacc aggactcata caggtgaaaa    1620

gcccttcagc tgtcggtggc caagttgtca gaaaaagttt gcccggtcag atgaattagt    1680

ccgccatcac aacatgcatc agagaaacat gaccaaactc cagctggcgc tttgaggggt    1740

ctccctcggg gaccgttcag tgtcccaggc agcacagtgt gtgaactgct ttcaagtctg    1800

actctccact cctcctcact aaaaaggaaa cttcagttga tcttcttcat ccaacttcca    1860

agacaagata ccggtgcttc tggaaactac caggtgtgcc tggaagagtt ggtctctgcc    1920
```

```
ctgcctactt ttagttgact cacaggccct ggagaagcag ctaacaatgt ctggttagtt   1980

aaaagcccat tgccatttgg tgtggatttt ctactgtaag aagagccata gctgatcatg   2040

tccccctgac ccttcccttc ttttttttatg ctcgttttcg ctggggatgg aattattgta   2100

ccattttcta tcatggaata tttataggcc agggcatgtg tatgtgtctg ctaatgtaaa   2160

ctttgtcatg gtttccattt actaacagca acagcaagaa ataaatcaga gagcaaggca   2220

tcgggggtga atcttgtcta acattcccga ggtcagccag gctgctaacc tggaaagcag   2280

gatgtagttc tgccaggcaa cttttaaagc tcatgcattt caagcagctg aagaaaaaat   2340

cagaactaac cagtacctct gtatagaaat ctaaaagaat tttaccattc agttaattca   2400

atgtgaacac tggcacactg ctcttaagaa actatgaaga tctgagattt ttttgtgtat   2460

gtttttgact cttttgagtg gtaatcatat gtgtctttat agatgtacat acctccttgc   2520

acaaatggag gggaattcat tttcatcact gggagtgtcc ttagtgtata aaaaccatgc   2580

tggtatatgg cttcaagttg taaaaatgaa agtgacttta aaagaaaata ggggatggtc   2640

caggatctcc actgataaga ctgtttttaa gtaacttaag gacctttggg tctacaagta   2700

tatgtgaaaa aaatgagact tactgggtga ggaaatccat tgtttaaaga tggtcgtgtg   2760

tgtgtgtgtg tgtgtgtgtg tgtgtgtgtt gtgttgtgtt ttgtttttta agggagggaa   2820

tttattattt accgttgctt gaaattactg tgtaaatata tgtctgataa tgatttgctc   2880

tttgacaact aaaattagga ctgtataagt actagatgca tcactgggtg ttgatcttac   2940

aagatattga tgataacact taaaattgta acctgcattt ttcactttgc tctcaattaa   3000

agtctattca aaaggaaaaa aaaaaaaa                                      3028
```

```
<210> SEQ ID NO 14
<211> LENGTH: 514
<212> TYPE: PRT
<213> ORGANISM: Homo sapiens

<400> SEQUENCE: 14

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
        115                 120                 125

Pro Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175
```

-continued

```
Tyr Gly Pro Phe Gly Pro Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly Val Ala Ala
305                 310                 315                 320

Gly Ser Ser Ser Ser Val Lys Trp Thr Glu Gly Gln Ser Asn His Ser
                325                 330                 335

Thr Gly Tyr Glu Ser Asp Asn His Thr Thr Pro Ile Leu Cys Gly Ala
            340                 345                 350

Gln Tyr Arg Ile His Thr His Gly Val Phe Arg Gly Ile Gln Asp Val
        355                 360                 365

Arg Arg Val Pro Gly Val Ala Pro Thr Leu Val Arg Ser Ala Ser Glu
    370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
                405                 410                 415

Gly Glu Lys Pro Tyr Gln Cys Asp Phe Lys Asp Cys Glu Arg Arg Phe
            420                 425                 430

Ser Arg Ser Asp Gln Leu Lys Arg His Gln Arg Arg His Thr Gly Val
        435                 440                 445

Lys Pro Phe Gln Cys Lys Thr Cys Gln Arg Lys Phe Ser Arg Ser Asp
    450                 455                 460

His Leu Lys Thr His Thr Arg Thr His Thr Gly Glu Lys Pro Phe Ser
465                 470                 475                 480

Cys Arg Trp Pro Ser Cys Gln Lys Lys Phe Ala Arg Ser Asp Glu Leu
                485                 490                 495

Val Arg His His Asn Met His Gln Arg Asn Met Thr Lys Leu Gln Leu
            500                 505                 510

Ala Leu


<210> SEQ ID NO 15
<211> LENGTH: 3037
<212> TYPE: DNA
<213> ORGANISM: Homo sapiens

<400> SEQUENCE: 15

agctggggta aggagttcaa ggcagcgccc acacccgggg gctctccgca acccgaccgc      60

ctgtccgctc ccccacttcc cgccctccct cccacctact cattcaccca cccacccacc     120

cagagccggg acggcagccc aggcgcccgg gccccgccgt ctcctcgccg cgatcctgga     180
```

-continued

```
cttcctcttg ctgcaggacc cggcttccac gtgtgtcccg gagccggcgt ctcagcacac    240
gctccgctcc gggcctgggt gcctacagca gccagagcag cagggagtcc gggacccggg    300
cggcatctgg gccaagttag gcgccgccga ggccagcgct gaacgtctcc agggccggag    360
gagccgcggg gcgtccgggt ctgagccgca gcaaatgggc tccgacgtgc gggacctgaa    420
cgcgctgctg cccgccgtcc cctccctggg tggcggcggc ggctgtgccc tgcctgtgag    480
cggcgcggcg cagtgggcgc cggtgctgga ctttgcgccc ccgggcgctt cggcttacgg    540
gtcgttgggc ggccccgcgc cgccaccggc tccgccgcca cccccgccgc cgccgcctca    600
ctccttcatc aaacaggagc cgagctgggg cggcgcggag ccgcacgagg agcagtgcct    660
gagcgccttc actgtccact ttccggcca gttcactggc acagccggag cctgtcgcta     720
cgggcccttc ggtcctcctc cgcccagcca ggcgtcatcc ggccaggcca ggatgtttcc    780
taacgcgccc tacctgccca gctgcctcga gagccagccc gctattcgca atcagggtta    840
cagcacggtc accttcgacg ggacgcccag ctacggtcac acgccctcgc accatgcggc    900
gcagttcccc aaccactcat tcaagcatga ggatcccatg ggccagcagg gctcgctggg    960
tgagcagcag tactcggtgc cgcccccggt ctatggctgc cacacccccca ccgacagctg  1020
caccggcagc caggctttgc tgctgaggac gccctacagc agtgacaatt tataccaaat   1080
gacatcccag cttgaatgca tgacctggaa tcagatgaac ttaggagcca ccttaaaggg   1140
agttgctgct gggagctcca gctcagtgaa atggacagaa gggcagagca accacagcac   1200
agggtacgag agcgataacc acacaacgcc catcctctgc ggagcccaat acagaataca   1260
cacgcacggt gtcttcagag gcattcagga tgtgcgacgt gtgcctggag tagccccgac   1320
tcttgtacgg tcggcatctg agaccagtga gaaacgcccc ttcatgtgtg cttacccagg   1380
ctgcaataag agatatttta agctgtccca cttacagatg cacagcagga agcacactgg   1440
tgagaaacca taccagtgtg acttcaagga ctgtgaacga aggttttctc gttcagacca   1500
gctcaaaaga caccaaagga gacatacagg tgtgaaacca ttccagtgta aaacttgtca   1560
gcgaaagttc tcccggtccg accacctgaa gacccacacc aggactcata caggtaaaac   1620
aagtgaaaag cccttcagct gtcggtggcc aagttgtcag aaaaagtttg cccggtcaga   1680
tgaattagtc cgccatcaca acatgcatca gagaaacatg accaaactcc agctggcgct   1740
ttgaggggtc tccctcgggg accgttcagt gtcccaggca gcacagtgtg tgaactgctt   1800
tcaagtctga ctctccactc ctcctcacta aaaaggaaac ttcagttgat cttcttcatc   1860
caacttccaa gacaagatac cggtgcttct ggaaactacc aggtgtgcct ggaagagttg   1920
gtctctgccc tgcctacttt tagttgactc acaggccctg gagaagcagc taacaatgtc   1980
tggttagtta aaagcccatt gccatttggt gtggattttc tactgtaaga agagccatag   2040
ctgatcatgt ccccctgacc cttcccttct ttttttatgc tcgttttcgc tggggatgga   2100
attattgtac cattttctat catggaatat ttataggcca gggcatgtgt atgtgtctgc   2160
taatgtaaac tttgtcatgg tttccattta ctaacagcaa cagcaagaaa taaatcagag   2220
agcaaggcat cgggggtgaa tcttgtctaa cattcccgag gtcagccagg ctgctaacct   2280
ggaaagcagg atgtagttct gccaggcaac ttttaaagct catgcatttc aagcagctga   2340
agaaaaaatc agaactaacc agtacctctg tatagaaatc taaaagaatt ttaccattca   2400
gttaattcaa tgtgaacact ggcacactgc tcttaagaaa ctatgaagat ctgagatttt   2460
tttgtgtatg tttttgactc ttttgagtgg taatcatatg tgtctttata gatgtacata   2520
cctccttgca caaatggagg ggaattcatt ttcatcactg ggagtgtcct tagtgtataa   2580
```

```
aaaccatgct ggtatatggc ttcaagttgt aaaaatgaaa gtgactttaa aagaaaatag   2640

gggatggtcc aggatctcca ctgataagac tgtttttaag taacttaagg acctttgggt   2700

ctacaagtat atgtgaaaaa aatgagactt actgggtgag gaaatccatt gtttaaagat   2760

ggtcgtgtgt gtgtgtgtgt gtgtgtgtgt gtgtgtgttg tgttgtgttt tgttttttaa   2820

gggagggaat ttattattta ccgttgcttg aaattactgt gtaaatatat gtctgataat   2880

gatttgctct ttgacaacta aaattaggac tgtataagta ctagatgcat cactgggtgt   2940

tgatcttaca agatattgat gataacactt aaaattgtaa cctgcatttt tcactttgct   3000

ctcaattaaa gtctattcaa aaggaaaaaa aaaaaaa                            3037


<210> SEQ ID NO 16
<211> LENGTH: 517
<212> TYPE: PRT
<213> ORGANISM: Homo sapiens

<400> SEQUENCE: 16

Met Gln Asp Pro Ala Ser Thr Cys Val Pro Glu Pro Ala Ser Gln His
1               5                   10                  15

Thr Leu Arg Ser Gly Pro Gly Cys Leu Gln Gln Pro Glu Gln Gln Gly
            20                  25                  30

Val Arg Asp Pro Gly Gly Ile Trp Ala Lys Leu Gly Ala Ala Glu Ala
        35                  40                  45

Ser Ala Glu Arg Leu Gln Gly Arg Arg Ser Arg Gly Ala Ser Gly Ser
    50                  55                  60

Glu Pro Gln Gln Met Gly Ser Asp Val Arg Asp Leu Asn Ala Leu Leu
65                  70                  75                  80

Pro Ala Val Pro Ser Leu Gly Gly Gly Gly Gly Cys Ala Leu Pro Val
                85                  90                  95

Ser Gly Ala Ala Gln Trp Ala Pro Val Leu Asp Phe Ala Pro Pro Gly
            100                 105                 110

Ala Ser Ala Tyr Gly Ser Leu Gly Gly Pro Ala Pro Pro Pro Ala Pro
        115                 120                 125

Pro Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Val His Phe Ser Gly Gln Phe Thr Gly Thr Ala Gly Ala Cys Arg
                165                 170                 175

Tyr Gly Pro Phe Gly Pro Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Ala Ile Arg Asn Gln Gly Tyr Ser Thr Val Thr Phe Asp Gly
    210                 215                 220

Thr Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Pro Val Tyr Gly Cys His Thr
            260                 265                 270

Pro Thr Asp Ser Cys Thr Gly Ser Gln Ala Leu Leu Leu Arg Thr Pro
        275                 280                 285
```

```
Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly Val Ala Ala
305                 310                 315                 320

Gly Ser Ser Ser Ser Val Lys Trp Thr Glu Gly Gln Ser Asn His Ser
                325                 330                 335

Thr Gly Tyr Glu Ser Asp Asn His Thr Thr Pro Ile Leu Cys Gly Ala
            340                 345                 350

Gln Tyr Arg Ile His Thr His Gly Val Phe Arg Gly Ile Gln Asp Val
        355                 360                 365

Arg Arg Val Pro Gly Val Ala Pro Thr Leu Val Arg Ser Ala Ser Glu
    370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
                405                 410                 415

Gly Glu Lys Pro Tyr Gln Cys Asp Phe Lys Asp Cys Glu Arg Arg Phe
            420                 425                 430

Ser Arg Ser Asp Gln Leu Lys Arg His Gln Arg Arg His Thr Gly Val
        435                 440                 445

Lys Pro Phe Gln Cys Lys Thr Cys Gln Arg Lys Phe Ser Arg Ser Asp
    450                 455                 460

His Leu Lys Thr His Thr Arg Thr His Thr Gly Lys Thr Ser Glu Lys
465                 470                 475                 480

Pro Phe Ser Cys Arg Trp Pro Ser Cys Gln Lys Lys Phe Ala Arg Ser
                485                 490                 495

Asp Glu Leu Val Arg His His Asn Met His Gln Arg Asn Met Thr Lys
            500                 505                 510

Leu Gln Leu Ala Leu
        515
```

<210> SEQ ID NO 17
<211> LENGTH: 2438
<212> TYPE: DNA
<213> ORGANISM: Homo sapiens

<400> SEQUENCE: 17

```
aggcgctttc accactgccc ctcccggggg gacctgaagg agagggtttg aggccggtct      60

ttgcccgccg aggtctgcgt gtccggtctg ggaggaggcc taggagggct cgcgggccac     120

gggcatcctt gggcccgagt tctggggtgc ggacggacgt ctcgagagtg ggtgccgcga     180

ctcgggaccc acggccctcg ccgggcacgg acagttgcgg agcagggctc tgaggattgt     240

gcagtgccct gggtccctgc ctactcctgg gctcaggaat ggagaagggt tacagcacgg     300

tcaccttcga cgggacgccc agctacggtc acacgccctc gcaccatgcg gcgcagttcc     360

ccaaccactc attcaagcat gaggatccca tgggccagca gggctcgctg ggtgagcagc     420

agtactcggt gccgcccccg gtctatggct gccacacccc caccgacagc tgcaccggca     480

gccaggcttt gctgctgagg acgccctaca gcagtgacaa tttataccaa atgacatccc     540

agcttgaatg catgacctgg aatcagatga acttaggagc caccttaaag ggccacagca     600

cagggtacga gagcgataac cacacaacgc ccatcctctg cggagcccaa tacagaatac     660

acacgcacgg tgtcttcaga ggcattcagg atgtgcgacg tgtgcctgga gtagccccga     720

ctcttgtacg gtcggcatct gagaccagtg agaaacgccc cttcatgtgt gcttacccag     780
```

```
gctgcaataa gagatatttt aagctgtccc acttacagat gcacagcagg aagcacactg     840

gtgagaaacc ataccagtgt gacttcaagg actgtgaacg aaggttttct cgttcagacc     900

agctcaaaag acaccaaagg agacatacag gtgtgaaacc attccagtgt aaaacttgtc     960

agcgaaagtt ctcccggtcc gaccacctga agacccacac caggactcat acaggtaaaa    1020

caagtgaaaa gcccttcagc tgtcggtggc caagttgtca gaaaaagttt gcccggtcag    1080

atgaattagt ccgccatcac aacatgcatc agagaaacat gaccaaactc cagctggcgc    1140

tttgaggggt ctccctcggg gaccgttcag tgtcccaggc agcacagtgt gtgaactgct    1200

ttcaagtctg actctccact cctcctcact aaaaaggaaa cttcagttga tcttcttcat    1260

ccaacttcca agacaagata ccggtgcttc tggaaactac caggtgtgcc tggaagagtt    1320

ggtctctgcc ctgcctactt ttagttgact cacaggccct ggagaagcag ctaacaatgt    1380

ctggttagtt aaaagcccat tgccatttgg tgtggatttt ctactgtaag aagagccata    1440

gctgatcatg tcccctgac ccttcccttc ttttttatg ctcgttttcg ctggggatgg    1500

aattattgta ccattttcta tcatggaata tttataggcc agggcatgtg tatgtgtctg    1560

ctaatgtaaa ctttgtcatg gtttccattt actaacagca acagcaagaa ataaatcaga    1620

gagcaaggca tcgggggtga atcttgtcta acattcccga ggtcagccag gctgctaacc    1680

tggaaagcag gatgtagttc tgccaggcaa cttttaaagc tcatgcattt caagcagctg    1740

aagaaaaaat cagaactaac cagtacctct gtatagaaat ctaaaagaat tttaccattc    1800

agttaattca atgtgaacac tggcacactg ctcttaagaa actatgaaga tctgagattt    1860

ttttgtgtat gtttttgact cttttgagtg gtaatcatat gtgtctttat agatgtacat    1920

acctccttgc acaaatggag gggaattcat tttcatcact gggagtgtcc ttagtgtata    1980

aaaaccatgc tggtatatgg cttcaagttg taaaaatgaa agtgacttta aaagaaaata    2040

ggggatggtc caggatctcc actgataaga ctgtttttaa gtaacttaag gacctttggg    2100

tctacaagta tatgtgaaaa aaatgagact tactgggtga ggaaatccat tgtttaaaga    2160

tggtcgtgtg tgtgtgtgtg tgtgtgtgtg tgtgtgtgtt gtgttgtgtt ttgtttttta    2220

agggagggaa tttattattt accgttgctt gaaattactg tgtaaatata tgtctgataa    2280

tgatttgctc tttgacaact aaaattagga ctgtataagt actagatgca tcactgggtg    2340

ttgatcttac aagatattga tgataacact taaaattgta acctgcattt ttcactttgc    2400

tctcaattaa agtctattca aaaggaaaaa aaaaaaaa                            2438
```

<210> SEQ ID NO 18
<211> LENGTH: 288
<212> TYPE: PRT
<213> ORGANISM: Homo sapiens

<400> SEQUENCE: 18

```
Met Glu Lys Gly Tyr Ser Thr Val Thr Phe Asp Gly Thr Pro Ser Tyr
1               5                   10                  15

Gly His Thr Pro Ser His His Ala Ala Gln Phe Pro Asn His Ser Phe
            20                  25                  30

Lys His Glu Asp Pro Met Gly Gln Gln Gly Ser Leu Gly Glu Gln Gln
        35                  40                  45

Tyr Ser Val Pro Pro Pro Val Tyr Gly Cys His Thr Pro Thr Asp Ser
    50                  55                  60

Cys Thr Gly Ser Gln Ala Leu Leu Leu Arg Thr Pro Tyr Ser Ser Asp
65                  70                  75                  80
```

-continued

```
Asn Leu Tyr Gln Met Thr Ser Gln Leu Glu Cys Met Thr Trp Asn Gln
                85                  90                  95

Met Asn Leu Gly Ala Thr Leu Lys Gly His Ser Thr Gly Tyr Glu Ser
            100                 105                 110

Asp Asn His Thr Thr Pro Ile Leu Cys Gly Ala Gln Tyr Arg Ile His
        115                 120                 125

Thr His Gly Val Phe Arg Gly Ile Gln Asp Val Arg Arg Val Pro Gly
    130                 135                 140

Val Ala Pro Thr Leu Val Arg Ser Ala Ser Glu Thr Ser Glu Lys Arg
145                 150                 155                 160

Pro Phe Met Cys Ala Tyr Pro Gly Cys Asn Lys Arg Tyr Phe Lys Leu
                165                 170                 175

Ser His Leu Gln Met His Ser Arg Lys His Thr Gly Glu Lys Pro Tyr
            180                 185                 190

Gln Cys Asp Phe Lys Asp Cys Glu Arg Arg Phe Ser Arg Ser Asp Gln
        195                 200                 205

Leu Lys Arg His Gln Arg Arg His Thr Gly Val Lys Pro Phe Gln Cys
    210                 215                 220

Lys Thr Cys Gln Arg Lys Phe Ser Arg Ser Asp His Leu Lys Thr His
225                 230                 235                 240

Thr Arg Thr His Thr Gly Lys Thr Ser Glu Lys Pro Phe Ser Cys Arg
                245                 250                 255

Trp Pro Ser Cys Gln Lys Lys Phe Ala Arg Ser Asp Glu Leu Val Arg
            260                 265                 270

His His Asn Met His Gln Arg Asn Met Thr Lys Leu Gln Leu Ala Leu
        275                 280                 285


<210> SEQ ID NO 19
<211> LENGTH: 2480
<212> TYPE: DNA
<213> ORGANISM: Homo sapiens

<400> SEQUENCE: 19

aggcgctttc accactgccc ctcccggggg gacctgaagg agagggtttg aggccggtct      60

ttgcccgccg aggtctgcgt gtccggtctg ggaggaggcc taggagggct cgcgggccac     120

gggcatcctt gggcccgagt tctggggtgc ggacggacgt ctcgagagtg ggtgccgcga     180

ctcgggaccc acggccctcg ccgggcacgg acagttgcgg agcagggctc tgaggattgt     240

gcagtgccct gggtccctgc ctactcctgg gctcaggaat ggagaagggt tacagcacgg     300

tcaccttcga cgggacgccc agctacggtc acacgccctc gcaccatgcg gcgcagttcc     360

ccaaccactc attcaagcat gaggatccca tgggccagca gggctcgctg ggtgagcagc     420

agtactcggt gccgcccccg gtctatggct gccacacccc caccgacagc tgcaccggca     480

gccaggcttt gctgctgagg acgccctaca gcagtgacaa tttataccaa atgacatccc     540

agcttgaatg catgacctgg aatcagatga acttaggagc caccttaaag ggagttgctg     600

ctgggagctc cagctcagtg aaatggacag aagggcagag caaccacagc acagggtacg     660

agagcgataa ccacacaacg cccatcctct gcggagccca atacagaata cacacgcacg     720

gtgtcttcag aggcattcag gatgtgcgac gtgtgcctgg agtagccccg actcttgtac     780

ggtcggcatc tgagaccagt gagaaacgcc ccttcatgtg tgcttaccca ggctgcaata     840

agagatattt taagctgtcc cacttacaga tgcacagcag gaagcacact ggtgagaaac     900

cataccagtg tgacttcaag gactgtgaac gaaggttttc tcgttcagac cagctcaaaa     960
```

```
gacaccaaag gagacataca ggtgtgaaac cattccagtg taaaacttgt cagcgaaagt   1020

tctcccggtc cgaccacctg aagacccaca ccaggactca tacaggtgaa aagcccttca   1080

gctgtcggtg gccaagttgt cagaaaaagt ttgcccggtc agatgaatta gtccgccatc   1140

acaacatgca tcagagaaac atgaccaaac tccagctggc gctttgaggg gtctccctcg   1200

gggaccgttc agtgtcccag gcagcacagt gtgtgaactg ctttcaagtc tgactctcca   1260

ctcctcctca ctaaaaagga aacttcagtt gatcttcttc atccaacttc caagacaaga   1320

taccggtgct tctggaaact accaggtgtg cctggaagag ttggtctctg ccctgcctac   1380

ttttagttga ctcacaggcc ctggagaagc agctaacaat gtctggttag ttaaaagccc   1440

attgccattt ggtgtggatt ttctactgta agaagagcca tagctgatca tgtccccctg   1500

acccttccct tcttttttta tgctcgtttt cgctggggat ggaattattg taccattttc   1560

tatcatggaa tatttatagg ccagggcatg tgtatgtgtc tgctaatgta aactttgtca   1620

tggtttccat ttactaacag caacagcaag aaataaatca gagagcaagg catcgggggt   1680

gaatcttgtc taacattccc gaggtcagcc aggctgctaa cctggaaagc aggatgtagt   1740

tctgccaggc aacttttaaa gctcatgcat ttcaagcagc tgaagaaaaa atcagaacta   1800

accagtacct ctgtatagaa atctaaaaga attttaccat tcagttaatt caatgtgaac   1860

actggcacac tgctcttaag aaactatgaa gatctgagat ttttttgtgt atgtttttga   1920

ctcttttgag tggtaatcat atgtgtcttt atagatgtac atacctcctt gcacaaatgg   1980

aggggaattc attttcatca ctgggagtgt ccttagtgta taaaaaccat gctggtatat   2040

ggcttcaagt tgtaaaaatg aaagtgactt taaaagaaaa taggggatgg tccaggatct   2100

ccactgataa gactgttttt aagtaactta aggacctttg ggtctacaag tatatgtgaa   2160

aaaaatgaga cttactgggt gaggaaatcc attgtttaaa gatggtcgtg tgtgtgtgtg   2220

tgtgtgtgtg tgtgtgtgtg ttgtgttgtg ttttgttttt taagggaggg aatttattat   2280

ttaccgttgc ttgaaattac tgtgtaaata tatgtctgat aatgatttgc tctttgacaa   2340

ctaaaattag gactgtataa gtactagatg catcactggg tgttgatctt acaagatatt   2400

gatgataaca cttaaaattg taacctgcat ttttcacttt gctctcaatt aaagtctatt   2460

caaaaggaaa aaaaaaaaaa                                               2480
```

<210> SEQ ID NO 20
<211> LENGTH: 302
<212> TYPE: PRT
<213> ORGANISM: Homo sapiens

<400> SEQUENCE: 20

```
Met Glu Lys Gly Tyr Ser Thr Val Thr Phe Asp Gly Thr Pro Ser Tyr
1               5                   10                  15

Gly His Thr Pro Ser His His Ala Ala Gln Phe Pro Asn His Ser Phe
            20                  25                  30

Lys His Glu Asp Pro Met Gly Gln Gln Gly Ser Leu Gly Glu Gln Gln
        35                  40                  45

Tyr Ser Val Pro Pro Pro Val Tyr Gly Cys His Thr Pro Thr Asp Ser
    50                  55                  60

Cys Thr Gly Ser Gln Ala Leu Leu Leu Arg Thr Pro Tyr Ser Ser Asp
65                  70                  75                  80

Asn Leu Tyr Gln Met Thr Ser Gln Leu Glu Cys Met Thr Trp Asn Gln
                85                  90                  95

Met Asn Leu Gly Ala Thr Leu Lys Gly Val Ala Ala Gly Ser Ser Ser
```

```
            100                 105                 110

Ser Val Lys Trp Thr Glu Gly Gln Ser Asn His Ser Thr Gly Tyr Glu
        115                 120                 125

Ser Asp Asn His Thr Thr Pro Ile Leu Cys Gly Ala Gln Tyr Arg Ile
    130                 135                 140

His Thr His Gly Val Phe Arg Gly Ile Gln Asp Val Arg Arg Val Pro
145                 150                 155                 160

Gly Val Ala Pro Thr Leu Val Arg Ser Ala Ser Glu Thr Ser Glu Lys
                165                 170                 175

Arg Pro Phe Met Cys Ala Tyr Pro Gly Cys Asn Lys Arg Tyr Phe Lys
            180                 185                 190

Leu Ser His Leu Gln Met His Ser Arg Lys His Thr Gly Glu Lys Pro
        195                 200                 205

Tyr Gln Cys Asp Phe Lys Asp Cys Glu Arg Arg Phe Ser Arg Ser Asp
    210                 215                 220

Gln Leu Lys Arg His Gln Arg Arg His Thr Gly Val Lys Pro Phe Gln
225                 230                 235                 240

Cys Lys Thr Cys Gln Arg Lys Phe Ser Arg Ser Asp His Leu Lys Thr
                245                 250                 255

His Thr Arg Thr His Thr Gly Glu Lys Pro Phe Ser Cys Arg Trp Pro
            260                 265                 270

Ser Cys Gln Lys Lys Phe Ala Arg Ser Asp Glu Leu Val Arg His His
        275                 280                 285

Asn Met His Gln Arg Asn Met Thr Lys Leu Gln Leu Ala Leu
    290                 295                 300


<210> SEQ ID NO 21
<211> LENGTH: 3092
<212> TYPE: DNA
<213> ORGANISM: Mus musculus

<400> SEQUENCE: 21

tgtgtgaatg gagcggccga gcatcctggc tcctcctcct tccctgctgc cggcccctct      60

tatttgagct ttgggaagct gggggcagcc aggcagctgg ggtaaggagt tcaaggcagc     120

gcccacaccc ggggctctcc gcaacccgac cgcctgcctg ctcccccttt ccttttcccg     180

ccctccctcc cacccactca ttcacccacc cacccagaga gaggacggca gcccaggaac     240

ccgggcccgc cgcctcctcg ccgcgatcct ggacttcctc ctgtcgcagg agccggcttc     300

cacgtgtgtc ccggagccgg cgtctcagca cacgctccgc cgggagcccg ggtgcgtcca     360

gcagccggag caacctgggg accgaggccc ccggagcgcc tgggccaagt ccagcgccga     420

gaatccgcag gatcgcagga gcggagaacc gtccgcatcc gagccgcacc tcatgggttc     480

cgacgtgcgg gacctgaacg cgctgctgcc cgctgtgtct tcgctgggcg gcggcggcgg     540

cggctgcggg ctccctgtga gcggcgcagc gcagtgggcg cccgtgttgg acttcgcgcc     600

tccgggcgcc tcggcttacg ggtcgctggg cggtcccgcg cctcctcccg ctccgccgcc     660

gcctccgccg ccacccccact ccttcatcaa acaggagccc agctggggcg gcgccgagcc     720

acacgaggag cagtgcctga gcgccttcac cttgcacttc tcgggccagt tcaccggtac     780

agccggggcc tgtcgctacg gaccccttcgg tcctcccccg cccagccagg cgtcctcggg     840

ccaggccagg atgttcccca atgcgcccta cctgcccagc tgcctggaga gccagcctac     900

catccgcaac caaggataca gcacggtcac tttcgacggg gcgcccagct atggccacac     960

gccctcgcat cacgcggcgc agttccccaa ccattccttc aaacacgagg accccatggg    1020
```

```
ccagcagggc tcgctgggcg agcagcagta ctccgtgcca cctccggtgt atggctgcca   1080

caccccctact gacagttgca caggcagcca ggccctgctc ctgaggacgc cctacagcag   1140

tgacaattta taccaaatga cctcccagct tgaatgcatg acctggaatc agatgaacct   1200

aggagctacc ttaaagggaa tggctgctgg gagctccagc tcagtgaaat ggacagaagg   1260

gcagagcaac cacggcacag ggtatgagag tgagaaccac acggccccca tcctctgtgg   1320

tgcccagtac agaatacaca cccacggggt cttccgaggc attcaggatg tgcggcgtgt   1380

atctggagtg gccccaactc ttgtccggtc agcatctgaa accagtgaga aacgtccttt   1440

catgtgtgca tacccaggct gcaataagag atattttaag ctgtcccact tacagatgca   1500

tagccggaag cacactggtg agaaaccata ccagtgtgac ttcaaggact gcgagagaag   1560

gttttctcgc tcagaccagc tcaaaagaca ccaaaggaga cacacaggtg tgaaaccatt   1620

ccagtgtaaa acttgtcagc gaaagttttc ccggtccgac catctgaaga cccacaccag   1680

gactcataca ggtaaaacaa gtgaaaagcc cttcagctgt cggtggcaca gttgtcagaa   1740

aaagtttgcg cgctcagacg aattggtccg ccatcacaac atgcatcaga gaaacatgac   1800

caaactccag ctggcgcttt gaggggtccg acacggagac agtccagcat cccaggcagg   1860

aaagtgtgca aactgcttcc aaatctgatt ttgaaattcc tcccactcac ctttcaaagg   1920

acacgactgt ggatctacat ccgacttcca agacagcaca cctgattgac tgcatcctat   1980

caggtttgcc ggaaggagtc ggtgctccgc ccacttttga ttaactcaca ggcctgaaaa   2040

aagtggttca cggtgtctag aaagtccatt gctattgtct gaattttcta ctgttagaag   2100

aaccattgtt gataatgccc cccgcccccc cccccgggtt tcctcttctc ctttgtgatc   2160

atttccccag gattagagag actgttacat tttctttcat gggatattta taggccaggg   2220

catgtgtatg tgcctgctaa tgtaaactct gtcatagttc ccatttacta actgccctag   2280

aaagaaataa atcagagagc aaggcaccag gggcaagaat cgtgcagaat ttcagaggtc   2340

tggctgcaaa cctggaaacc tggaaggcca gatgtaattc tacaggcgat tgttaaagct   2400

cataggtttt gagtaactgc atagtaggtt ggtattaact agaactcctg tatagttagg   2460

acagagagga gccttcctgc tcagctattc actctgaaca ctagcactgg gctcttaaga   2520

aatgatgttt taagagcaga gatctttttt taatgtcttt gatttatttt ttagttgtaa   2580

ttaggtacat cctcagagat gtactttcct cctcttgtgc aggatgtgga ggactcagtt   2640

ccatcatctg gggcatcttt agagtgtata gaccacactg gttatgtggc ttcaagttgt   2700

aaaaattaaa atgactttaa aagaaactag gggctggtcc aggatcttca ctggtaagac   2760

tgttcttaag taacttaagt atctttgaat ctgcaagtat gtagggaaaa aaaaaagata   2820

tattattgtg aggaaatcca ttgtttaaag gtgtgcgtgt gttgttgttg tttttaaag   2880

ggagggagtt tattatttac tgtagcttga aatactgtgt aaatatatat gtatatatat   2940

gatgtgctct ttgtcaacta aaattaggag gtgtatggta ttagctgcat cactgtgtgg   3000

atgtcaatct tacagtgtat tgatgataat actaaaaatg taacctgcat ctttttccac   3060

ttggctgtca attaaagtct attcaaaagg aa                                  3092
```

<210> SEQ ID NO 22
<211> LENGTH: 517
<212> TYPE: PRT
<213> ORGANISM: Mus musculus

<400> SEQUENCE: 22

```
Met Asp Phe Leu Leu Ser Gln Glu Pro Ala Ser Thr Cys Val Pro Glu
1               5                   10                  15

Pro Ala Ser Gln His Thr Leu Arg Arg Glu Pro Gly Cys Val Gln Gln
            20                  25                  30

Pro Glu Gln Pro Gly Asp Arg Gly Pro Arg Ser Ala Trp Ala Lys Ser
        35                  40                  45

Ser Ala Glu Asn Pro Gln Asp Arg Arg Ser Gly Glu Pro Ser Ala Ser
    50                  55                  60

Glu Pro His Leu Met Gly Ser Asp Val Arg Asp Leu Asn Ala Leu Leu
65                  70                  75                  80

Pro Ala Val Ser Ser Leu Gly Gly Gly Gly Gly Gly Cys Gly Leu Pro
                85                  90                  95

Val Ser Gly Ala Ala Gln Trp Ala Pro Val Leu Asp Phe Ala Pro Pro
            100                 105                 110

Gly Ala Ser Ala Tyr Gly Ser Leu Gly Gly Pro Ala Pro Pro Pro Ala
        115                 120                 125

Pro Pro Pro Pro Pro Pro Pro Pro His Ser Phe Ile Lys Gln Glu Pro
    130                 135                 140

Ser Trp Gly Gly Ala Glu Pro His Glu Glu Gln Cys Leu Ser Ala Phe
145                 150                 155                 160

Thr Leu His Phe Ser Gly Gln Phe Thr Gly Thr Ala Gly Ala Cys Arg
                165                 170                 175

Tyr Gly Pro Phe Gly Pro Pro Pro Pro Ser Gln Ala Ser Ser Gly Gln
            180                 185                 190

Ala Arg Met Phe Pro Asn Ala Pro Tyr Leu Pro Ser Cys Leu Glu Ser
        195                 200                 205

Gln Pro Thr Ile Arg Asn Gln Gly Tyr Ser Thr Val Thr Phe Asp Gly
    210                 215                 220

Ala Pro Ser Tyr Gly His Thr Pro Ser His His Ala Ala Gln Phe Pro
225                 230                 235                 240

Asn His Ser Phe Lys His Glu Asp Pro Met Gly Gln Gln Gly Ser Leu
                245                 250                 255

Gly Glu Gln Gln Tyr Ser Val Pro Pro Pro Val Tyr Gly Cys His Thr
            260                 265                 270

Pro Thr Asp Ser Cys Thr Gly Ser Gln Ala Leu Leu Leu Arg Thr Pro
        275                 280                 285

Tyr Ser Ser Asp Asn Leu Tyr Gln Met Thr Ser Gln Leu Glu Cys Met
    290                 295                 300

Thr Trp Asn Gln Met Asn Leu Gly Ala Thr Leu Lys Gly Met Ala Ala
305                 310                 315                 320

Gly Ser Ser Ser Ser Val Lys Trp Thr Glu Gly Gln Ser Asn His Gly
                325                 330                 335

Thr Gly Tyr Glu Ser Glu Asn His Thr Ala Pro Ile Leu Cys Gly Ala
            340                 345                 350

Gln Tyr Arg Ile His Thr His Gly Val Phe Arg Gly Ile Gln Asp Val
        355                 360                 365

Arg Arg Val Ser Gly Val Ala Pro Thr Leu Val Arg Ser Ala Ser Glu
    370                 375                 380

Thr Ser Glu Lys Arg Pro Phe Met Cys Ala Tyr Pro Gly Cys Asn Lys
385                 390                 395                 400

Arg Tyr Phe Lys Leu Ser His Leu Gln Met His Ser Arg Lys His Thr
                405                 410                 415

Gly Glu Lys Pro Tyr Gln Cys Asp Phe Lys Asp Cys Glu Arg Arg Phe
```

```
            420                 425                 430

Ser Arg Ser Asp Gln Leu Lys Arg His Gln Arg Arg His Thr Gly Val
        435                 440                 445

Lys Pro Phe Gln Cys Lys Thr Cys Gln Arg Lys Phe Ser Arg Ser Asp
    450                 455                 460

His Leu Lys Thr His Thr Arg Thr His Thr Gly Lys Thr Ser Glu Lys
465                 470                 475                 480

Pro Phe Ser Cys Arg Trp His Ser Cys Gln Lys Lys Phe Ala Arg Ser
                485                 490                 495

Asp Glu Leu Val Arg His His Asn Met His Gln Arg Asn Met Thr Lys
            500                 505                 510

Leu Gln Leu Ala Leu
        515


<210> SEQ ID NO 23
<211> LENGTH: 2126
<212> TYPE: DNA
<213> ORGANISM: Homo sapiens

<400> SEQUENCE: 23

gccaggctct ccaccccac ttcccaattg aggaaaccga ggcagaggag gctcagagag     60

ctaccggtgg acccacggtg cctccctccc tgggatctac acagaccatg gccttgccaa    120

cggctcgacc cctgttgggg tcctgtggga cccccgccct cggcagcctc ctgttcctgc    180

tcttcagcct cggatgggtg cagccctcga ggaccctggc tggagagaca gggcaggagg    240

ctgcgcccct ggacggagtc ctggccaacc cacctaacat ttccagcctc tcccctcgcc    300

aactccttgg cttcccgtgt gcggaggtgt ccggcctgag cacggagcgt gtccgggagc    360

tggctgtggc cttggcacag aagaatgtca agctctcaac agagcagctg cgctgtctgg    420

ctcaccggct ctctgagccc cccgaggacc tggacgccct cccattggac ctgctgctat    480

tcctcaaccc agatgcgttc tcggggcccc aggcctgcac ccgtttcttc tcccgcatca    540

cgaaggccaa tgtggacctg ctcccgaggg gggctcccga gcgacagcgg ctgctgcctg    600

cggctctggc ctgctggggt gtgcgggggt ctctgctgag cgaggctgat gtgcgggctc    660

tgggaggcct ggcttgcgac ctgcctgggc gctttgtggc cgagtcggcc gaagtgctgc    720

taccccggct ggtgagctgc ccgggacccc tggaccagga ccagcaggag gcagccaggg    780

cggctctgca gggcggggga ccccctacg gcccccgtc gacatggtct gtctccacga    840

tggacgctct gcggggcctg ctgcccgtgc tgggccagcc catcatccgc agcatcccgc    900

agggcatcgt ggccgcgtgg cggcaacgct cctctcggga cccatcctgg cggcagcctg    960

aacggaccat cctccggccg cggttccggc gggaagtgga gaagacagcc tgtccttcag   1020

gcaagaaggc ccgcgagata gacgagagcc tcatcttcta caagaagtgg gagctggaag   1080

cctgcgtgga tgcggccctg ctggccaccc agatggaccg cgtgaacgcc atccccttca   1140

cctacgagca gctggacgtc ctaaagcata aactggatga gctctaccca caaggttacc   1200

ccgagtctgt gatccagcac ctgggctacc tcttcctcaa gatgagccct gaggacattc   1260

gcaagtggaa tgtgacgtcc ctggagaccc tgaaggcttt gcttgaagtc aacaaagggc   1320

acgaaatgag tcctcaggtg gccaccctga tcgaccgctt tgtgaaggga aggggccagc   1380

tagacaaaga caccctagac accctgaccg ccttctaccc tgggtacctg tgctccctca   1440

gccccgagga gctgagctcc gtgcccccca gcagcatctg ggcggtcagg ccccaggacc   1500

tggacacgtg tgacccaagg cagctggacg tcctctatcc caaggcccgc cttgctttcc   1560
```

```
agaacatgaa cgggtccgaa tacttcgtga agatccagtc cttcctgggt ggggccccca   1620

cggaggattt gaaggcgctc agtcagcaga atgtgagcat ggacttggcc acgttcatga   1680

agctgcggac ggatgcggtg ctgccgttga ctgtggctga ggtgcagaaa cttctgggac   1740

cccacgtgga gggcctgaag gcggaggagc ggcaccgccc ggtgcgggac tggatcctac   1800

ggcagcggca ggacgacctg gacacgctgg ggctggggct acagggcggc atccccaacg   1860

gctacctggt cctagacctc agcatgcaag aggccctctc ggggacgccc tgcctcctag   1920

gacctggacc tgttctcacc gtcctggcac tgctcctagc ctccaccctg gcctgagggc   1980

cccactccct tgctggcccc agccctgctg gggatccccg cctggccagg agcaggcacg   2040

ggtggtcccc gttccacccc aagagaactc gcgctcagta aacgggaaca tgccccctgc   2100

agacacgtaa aaaaaaaaaa aaaaaa                                        2126


<210> SEQ ID NO 24
<211> LENGTH: 622
<212> TYPE: PRT
<213> ORGANISM: Homo sapiens

<400> SEQUENCE: 24

Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270
```

```
Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430

Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
    610                 615                 620


<210> SEQ ID NO 25
<211> LENGTH: 2187
<212> TYPE: DNA
<213> ORGANISM: Homo sapiens

<400> SEQUENCE: 25

tgccaggctc tccaccccca cttcccaatt gaggaaaccg aggcagagga ggctcagcgc      60

cacgcactcc tctttctgcc tggccggcca ctcccgtctg ctgtgacgcg cggacagaga     120
```

```
gctaccggtg gacccacggt gcctccctcc ctgggatcta cacagaccat ggccttgcca    180

acggctcgac ccctgttggg gtcctgtggg acccccgccc tcggcagcct cctgttcctg    240

ctcttcagcc tcggatgggt gcagccctcg aggaccctgg ctggagagac agggcaggag    300

gctgcgcccc tggacggagt cctggccaac ccacctaaca tttccagcct ctcccctcgc    360

caactccttg gcttcccgtg tgcggaggtg tccggcctga gcacggagcg tgtccgggag    420

ctggctgtgg ccttggcaca gaagaatgtc aagctctcaa cagagcagct gcgctgtctg    480

gctcaccggc tctctgagcc ccccgaggac ctggacgccc tcccattgga cctgctgcta    540

ttcctcaacc cagatgcgtt ctcggggccc caggcctgca cccgtttctt ctcccgcatc    600

acgaaggcca atgtggacct gctcccgagg ggggctcccg agcgacagcg gctgctgcct    660

gcggctctgg cctgctgggg tgtgcggggg tctctgctga gcgaggctga tgtgcgggct    720

ctgggaggcc tggcttgcga cctgcctggg cgctttgtgg ccgagtcggc cgaagtgctg    780

ctaccccggc tggtgagctg cccgggaccc ctggaccagg accagcagga ggcagccagg    840

gcggctctgc agggcggggg acccccctac ggcccccccgt cgacatggtc tgtctccacg    900

atggacgctc tgcggggcct gctgcccgtg ctgggccagc ccatcatccg cagcatcccg    960

cagggcatcg tggccgcgtg gcggcaacgc tcctctcggg acccatcctg gcggcagcct   1020

gaacggacca tcctccggcc gcggttccgg cgggaagtgg agaagacagc ctgtccttca   1080

ggcaagaagg cccgcgagat agacgagagc ctcatcttct acaagaagtg ggagctggaa   1140

gcctgcgtgg atgcggccct gctggccacc cagatggacc gcgtgaacgc catccccttc   1200

acctacgagc agctggacgt cctaaagcat aaactggatg agctctaccc acaaggttac   1260

cccgagtctg tgatccagca cctgggctac ctcttcctca agatgagccc tgaggacatt   1320

cgcaagtgga atgtgacgtc cctggagacc ctgaaggctt tgcttgaagt caacaaaggg   1380

cacgaaatga gtcctcaggt ggccaccctg atcgaccgct ttgtgaaggg aaggggccag   1440

ctagacaaag acaccctaga caccctgacc gccttctacc ctgggtacct gtgctccctc   1500

agccccgagg agctgagctc cgtgcccccc agcagcatct gggcggtcag gccccaggac   1560

ctggacacgt gtgacccaag gcagctggac gtcctctatc ccaaggcccg ccttgctttc   1620

cagaacatga acgggtccga atacttcgtg aagatccagt ccttcctggg tggggccccc   1680

acggaggatt tgaaggcgct cagtcagcag aatgtgagca tggacttggc cacgttcatg   1740

aagctgcgga cggatgcggt gctgccgttg actgtggctg aggtgcagaa acttctggga   1800

ccccacgtgg agggcctgaa ggcggaggag cggcaccgcc cggtgcggga ctggatccta   1860

cggcagcggc aggacgacct ggacacgctg gggctggggc tacagggcgg catccccaac   1920

ggctacctgg tcctagacct cagcatgcaa gaggccctct cggggacgcc ctgcctccta   1980

ggacctggac ctgttctcac cgtcctggca ctgctcctag cctccaccct ggcctgaggg   2040

ccccactccc ttgctggccc cagccctgct ggggatcccc gcctggccag gagcaggcac   2100

gggtggtccc cgttccaccc caagagaact cgcgctcagt aaacgggaac atgccccctg   2160

cagacacgta aaaaaaaaaa aaaaaaa                                       2187
```

```
<210> SEQ ID NO 26
<211> LENGTH: 622
<212> TYPE: PRT
<213> ORGANISM: Homo sapiens

<400> SEQUENCE: 26

Met Ala Leu Pro Thr Ala Arg Pro Leu Leu Gly Ser Cys Gly Thr Pro
```

-continued

```
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
                405                 410                 415

Arg Phe Val Lys Gly Arg Gly Gln Leu Asp Lys Asp Thr Leu Asp Thr
            420                 425                 430
```

```
Leu Thr Ala Phe Tyr Pro Gly Tyr Leu Cys Ser Leu Ser Pro Glu Glu
        435                 440                 445

Leu Ser Ser Val Pro Pro Ser Ser Ile Trp Ala Val Arg Pro Gln Asp
    450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
                485                 490                 495

Gln Ser Phe Leu Gly Gly Ala Pro Thr Glu Asp Leu Lys Ala Leu Ser
            500                 505                 510

Gln Gln Asn Val Ser Met Asp Leu Ala Thr Phe Met Lys Leu Arg Thr
        515                 520                 525

Asp Ala Val Leu Pro Leu Thr Val Ala Glu Val Gln Lys Leu Leu Gly
    530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
                565                 570                 575

Gly Leu Gln Gly Gly Ile Pro Asn Gly Tyr Leu Val Leu Asp Leu Ser
            580                 585                 590

Met Gln Glu Ala Leu Ser Gly Thr Pro Cys Leu Leu Gly Pro Gly Pro
        595                 600                 605

Val Leu Thr Val Leu Ala Leu Leu Leu Ala Ser Thr Leu Ala
    610                 615                 620
```

<210> SEQ ID NO 27
<211> LENGTH: 2154
<212> TYPE: DNA
<213> ORGANISM: Homo sapiens

<400> SEQUENCE: 27

```
cgccacgcac tcctctttct gcctggccgg ccactcccgt ctgctgtgac gcgcggacag     60

agagctaccg gtggacccac ggtgcctccc tccctgggat ctacacagac catggccttg    120

ccaacggctc gacccctgtt ggggtcctgt gggacccccg ccctcggcag cctcctgttc    180

ctgctcttca gcctcggatg ggtgcagccc tcgaggaccc tggctggaga gacagggcag    240

gaggctgcgc ccctggacgg agtcctggcc aacccaccta acatttccag cctctcccct    300

cgccaactcc ttggcttccc gtgtgcggag gtgtccggcc tgagcacgga gcgtgtccgg    360

gagctggctg tggccttggc acagaagaat gtcaagctct caacagagca gctgcgctgt    420

ctggctcacc ggctctctga gccccccgag gacctggacg ccctcccatt ggacctgctg    480

ctattcctca acccagatgc gttctcgggg ccccaggcct gcacccgttt cttctcccgc    540

atcacgaagg ccaatgtgga cctgctcccg agggggggctc ccgagcgaca gcggctgctg    600

cctgcggctc tggcctgctg gggtgtgcgg gggtctctgc tgagcgaggc tgatgtgcgg    660

gctctgggag gcctggcttg cgacctgcct gggcgctttg tggccgagtc ggccgaagtg    720

ctgctacccc ggctggtgag ctgcccggga cccctggacc aggaccagca ggaggcagcc    780

agggcggctc tgcagggcgg gggacccccc tacggccccc cgtcgacatg gtctgtctcc    840

acgatggacg ctctgcgggg cctgctgccc gtgctgggcc agcccatcat ccgcagcatc    900

ccgcagggca tcgtggccgc gtggcggcaa cgctcctctc gggacccatc ctggcggcag    960

cctgaacgga ccatcctccg gccgcggttc cggcgggaag tggagaagac agcctgtcct   1020
```

```
tcaggcaaga aggcccgcga gatagacgag agcctcatct tctacaagaa gtgggagctg   1080

gaagcctgcg tggatgcggc cctgctggcc acccagatgg accgcgtgaa cgccatcccc   1140

ttcacctacg agcagctgga cgtcctaaag cataaactgg atgagctcta cccacaaggt   1200

taccccgagt ctgtgatcca gcacctgggc tacctcttcc tcaagatgag ccctgaggac   1260

attcgcaagt ggaatgtgac gtccctggag accctgaagg ctttgcttga agtcaacaaa   1320

gggcacgaaa tgagtcctca ggctcctcgg cggcccctcc cacaggtggc caccctgatc   1380

gaccgctttg tgaagggaag ggccagcta gacaaagaca ccctagacac cctgaccgcc   1440

ttctaccctg ggtacctgtg ctccctcagc cccgaggagc tgagctccgt gccccccagc   1500

agcatctggg cggtcaggcc ccaggacctg gacacgtgtg acccaaggca gctggacgtc   1560

ctctatccca aggcccgcct tgctttccag aacatgaacg ggtccgaata cttcgtgaag   1620

atccagtcct tcctgggtgg ggcccccacg gaggatttga aggcgctcag tcagcagaat   1680

gtgagcatgg acttggccac gttcatgaag ctgcggacgg atgcggtgct gccgttgact   1740

gtggctgagg tgcagaaact tctgggaccc cacgtggagg gcctgaaggc ggaggagcgg   1800

caccgcccgg tgcgggactg gatcctacgg cagcggcagg acgacctgga cacgctgggg   1860

ctggggctac agggcggcat ccccaacggc tacctggtcc tagacctcag catgcaagag   1920

gccctctcgg ggacgccctg cctcctagga cctggacctg ttctcaccgt cctggcactg   1980

ctcctagcct ccaccctggc ctgagggccc cactcccttg ctggccccag ccctgctggg   2040

gatccccgcc tggccaggag caggcacggg tggtccccgt tccaccccaa gagaactcgc   2100

gctcagtaaa cgggaacatg ccccctgcag acacgtaaaa aaaaaaaaaa aaaa         2154
```

<210> SEQ ID NO 28
<211> LENGTH: 630
<212> TYPE: PRT
<213> ORGANISM: Homo sapiens

<400> SEQUENCE: 28

```
Met Ala Leu Pro Thr Ala Arg Pro Leu Leu Gly Ser Cys Gly Thr Pro
1               5                   10                  15

Ala Leu Gly Ser Leu Leu Phe Leu Leu Phe Ser Leu Gly Trp Val Gln
            20                  25                  30

Pro Ser Arg Thr Leu Ala Gly Glu Thr Gly Gln Glu Ala Ala Pro Leu
        35                  40                  45

Asp Gly Val Leu Ala Asn Pro Pro Asn Ile Ser Ser Leu Ser Pro Arg
    50                  55                  60

Gln Leu Leu Gly Phe Pro Cys Ala Glu Val Ser Gly Leu Ser Thr Glu
65                  70                  75                  80

Arg Val Arg Glu Leu Ala Val Ala Leu Ala Gln Lys Asn Val Lys Leu
                85                  90                  95

Ser Thr Glu Gln Leu Arg Cys Leu Ala His Arg Leu Ser Glu Pro Pro
            100                 105                 110

Glu Asp Leu Asp Ala Leu Pro Leu Asp Leu Leu Leu Phe Leu Asn Pro
        115                 120                 125

Asp Ala Phe Ser Gly Pro Gln Ala Cys Thr Arg Phe Phe Ser Arg Ile
    130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175
```

```
Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
        195                 200                 205

Val Ser Cys Pro Gly Pro Leu Asp Gln Asp Gln Gln Glu Ala Ala Arg
    210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300

Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
                325                 330                 335

Asp Arg Val Asn Ala Ile Pro Phe Thr Tyr Glu Gln Leu Asp Val Leu
            340                 345                 350

Lys His Lys Leu Asp Glu Leu Tyr Pro Gln Gly Tyr Pro Glu Ser Val
        355                 360                 365

Ile Gln His Leu Gly Tyr Leu Phe Leu Lys Met Ser Pro Glu Asp Ile
    370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Ala Pro Arg Arg Pro Leu
                405                 410                 415

Pro Gln Val Ala Thr Leu Ile Asp Arg Phe Val Lys Gly Arg Gly Gln
            420                 425                 430

Leu Asp Lys Asp Thr Leu Asp Thr Leu Thr Ala Phe Tyr Pro Gly Tyr
        435                 440                 445

Leu Cys Ser Leu Ser Pro Glu Glu Leu Ser Ser Val Pro Pro Ser Ser
    450                 455                 460

Ile Trp Ala Val Arg Pro Gln Asp Leu Asp Thr Cys Asp Pro Arg Gln
465                 470                 475                 480

Leu Asp Val Leu Tyr Pro Lys Ala Arg Leu Ala Phe Gln Asn Met Asn
                485                 490                 495

Gly Ser Glu Tyr Phe Val Lys Ile Gln Ser Phe Leu Gly Gly Ala Pro
            500                 505                 510

Thr Glu Asp Leu Lys Ala Leu Ser Gln Gln Asn Val Ser Met Asp Leu
        515                 520                 525

Ala Thr Phe Met Lys Leu Arg Thr Asp Ala Val Leu Pro Leu Thr Val
    530                 535                 540

Ala Glu Val Gln Lys Leu Leu Gly Pro His Val Glu Gly Leu Lys Ala
545                 550                 555                 560

Glu Glu Arg His Arg Pro Val Arg Asp Trp Ile Leu Arg Gln Arg Gln
                565                 570                 575

Asp Asp Leu Asp Thr Leu Gly Leu Gly Leu Gln Gly Gly Ile Pro Asn
            580                 585                 590

Gly Tyr Leu Val Leu Asp Leu Ser Met Gln Glu Ala Leu Ser Gly Thr
```

```
        595                 600                 605

Pro Cys Leu Leu Gly Pro Gly Pro Val Leu Thr Val Leu Ala Leu Leu
    610                 615                 620

Leu Ala Ser Thr Leu Ala
625                 630
```

```
<210> SEQ ID NO 29
<211> LENGTH: 2135
<212> TYPE: DNA
<213> ORGANISM: Mus musculus

<400> SEQUENCE: 29

ggacagctgc tttcccaggc ccaaaagccc cttcgttgtc tccaaacagt ggtgtgggtt      60

gaggggtggg acaagtgggg acctcagagt cattgttatc cacagaccat ggccttgcca     120

acagctcgac ccctgctggg gtcctgtgga agtcccatct gcagccgaag cttcctactg     180

cttctcctta gtcttgggtg gataccacgt ctgcagaccc agactacaaa gacaagccag     240

gaggccacac tcctccatgc tgtgaacggt gccgctgact ttgccagtct ccccacaggc     300

ctctttcttg gcctcacatg tgaggaggta tctgacctga gcatggaaca agccaagggg     360

ctggctatgg ctgtaagaca gaagaacatt acactccggg gacatcagct gcgttgtctg     420

gcacgtcgcc ttcctaggca cctcaccgac gaggaactga atgctcttcc actggacctg     480

ctgctcttcc tcaacccagc catgtttcca gggcaacagg cttgtgccca cttcttctcc     540

ctcatctcta aagccaatgt ggatgtactc ccacggaggt ctctggagcg ccagaggctg     600

ctgatggagg ctctgaagtg ccagggcgtg tatggatttc aagtgagtga ggcagatgtg     660

cgggctctcg gaggcctggc ctgtgacctg cctgggaaat ttgtggccag atcttccgaa     720

gttctcctcc cctggctggc aggatgccaa ggacccctgg accagagcca ggaaaaggca     780

gtcagggagg ttctgaggag tggaagaacc caatatggcc ccccatcgaa gtggtcagtc     840

tccaccctgg atgccctgca gagcttggta gcagtgttgg atgagtccat cgtccagagc     900

atccccaagg atgtcaaagc tgaatggctg caacacatct ccagagaccc ctccaggctg     960

gggtctaagc tgaccgtcat acacccaagg ttccgacggg atgcagaaca gaaagcctgc    1020

cctccaggga aggagcccta caaggtggat gaagacctca tcttctacca gaattgggag    1080

ctggaggctt gtgtagatgg caccatgctg gccagacaaa tggaccttgt gaacgagatt    1140

cccttcacct atgagcagct cagtatcttt aagcacaaac tggacaagac ctacccacaa    1200

ggctatcctg agtccctgat ccagcagctg ggtcacttct tcagatatgt tagccctgaa    1260

gacatccacc agtggaatgt gacctcacca gacacagtga aaactctgct caaagtcagc    1320

aaaggacaaa agatgaatgc tcaggcgatt gccttggtcg cctgctatct tcggggagga    1380

ggccagctgg acgaggatat ggtaaaagcc ctgggcgaca tcccgttaag ctatctatgt    1440

gacttcagcc cccaggatct gcactcggta ccctccagtg tcatgtggct ggttgggccc    1500

caagacctgg acaagtgcag ccagaggcat ctgggtctcc tctaccagaa ggcctgctca    1560

gccttccaga atgtgagcgg cctagaatac tttgagaaaa tcaagacatt cctgggtggg    1620

gcctccgtga aggacctgcg ggccctcagc cagcacaatg tgagcatgga catagccact    1680

ttcaagaggc tgcaggtgga ttccctggtg gggctgagtg tggctgaggt acagaaactt    1740

ctggggccaa acattgtgga cctgaagacc gaggaggata aaagccctgt ccgtgactgg    1800

ctgttccggc agcatcagaa agacctagac aggctgggtt tgggacttca gggtggcatc    1860

cccaatggct acctggtcct ggacttcaat gtccgagagg ccttctccag cagagcctca    1920
```

```
ctccttgggc caggatttgt attaatatgg attccagctc tgctcccagc tttaaggctg   1980

agctgagacc accaccctgc aaggctcctg gtcccagctc tactggggcc ctcttgacca   2040

ggagtgggta ccaggggtca ttgccaaagt ttgaggactc ttgaactcaa taaacagtgg   2100

catatgctcc cttgaaaaaa aaaaaaaaaa aaaaa                              2135


<210> SEQ ID NO 30
<211> LENGTH: 625
<212> TYPE: PRT
<213> ORGANISM: Mus musculus

<400> SEQUENCE: 30

Met Ala Leu Pro Thr Ala Arg Pro Leu Leu Gly Ser Cys Gly Ser Pro
1               5                   10                  15

Ile Cys Ser Arg Ser Phe Leu Leu Leu Leu Leu Ser Leu Gly Trp Ile
            20                  25                  30

Pro Arg Leu Gln Thr Gln Thr Thr Lys Thr Ser Gln Glu Ala Thr Leu
        35                  40                  45

Leu His Ala Val Asn Gly Ala Ala Asp Phe Ala Ser Leu Pro Thr Gly
    50                  55                  60

Leu Phe Leu Gly Leu Thr Cys Glu Glu Val Ser Asp Leu Ser Met Glu
65                  70                  75                  80

Gln Ala Lys Gly Leu Ala Met Ala Val Arg Gln Lys Asn Ile Thr Leu
                85                  90                  95

Arg Gly His Gln Leu Arg Cys Leu Ala Arg Arg Leu Pro Arg His Leu
            100                 105                 110

Thr Asp Glu Glu Leu Asn Ala Leu Pro Leu Asp Leu Leu Leu Phe Leu
        115                 120                 125

Asn Pro Ala Met Phe Pro Gly Gln Gln Ala Cys Ala His Phe Phe Ser
    130                 135                 140

Leu Ile Ser Lys Ala Asn Val Asp Val Leu Pro Arg Arg Ser Leu Glu
145                 150                 155                 160

Arg Gln Arg Leu Leu Met Glu Ala Leu Lys Cys Gln Gly Val Tyr Gly
                165                 170                 175

Phe Gln Val Ser Glu Ala Asp Val Arg Ala Leu Gly Gly Leu Ala Cys
            180                 185                 190

Asp Leu Pro Gly Lys Phe Val Ala Arg Ser Ser Glu Val Leu Leu Pro
        195                 200                 205

Trp Leu Ala Gly Cys Gln Gly Pro Leu Asp Gln Ser Gln Glu Lys Ala
    210                 215                 220

Val Arg Glu Val Leu Arg Ser Gly Arg Thr Gln Tyr Gly Pro Pro Ser
225                 230                 235                 240

Lys Trp Ser Val Ser Thr Leu Asp Ala Leu Gln Ser Leu Val Ala Val
                245                 250                 255

Leu Asp Glu Ser Ile Val Gln Ser Ile Pro Lys Asp Val Lys Ala Glu
            260                 265                 270

Trp Leu Gln His Ile Ser Arg Asp Pro Ser Arg Leu Gly Ser Lys Leu
        275                 280                 285

Thr Val Ile His Pro Arg Phe Arg Arg Asp Ala Glu Gln Lys Ala Cys
    290                 295                 300

Pro Pro Gly Lys Glu Pro Tyr Lys Val Asp Glu Asp Leu Ile Phe Tyr
305                 310                 315                 320

Gln Asn Trp Glu Leu Glu Ala Cys Val Asp Gly Thr Met Leu Ala Arg
                325                 330                 335
```

```
Gln Met Asp Leu Val Asn Glu Ile Pro Phe Thr Tyr Glu Gln Leu Ser
            340                 345                 350

Ile Phe Lys His Lys Leu Asp Lys Thr Tyr Pro Gln Gly Tyr Pro Glu
        355                 360                 365

Ser Leu Ile Gln Gln Leu Gly His Phe Phe Arg Tyr Val Ser Pro Glu
    370                 375                 380

Asp Ile His Gln Trp Asn Val Thr Ser Pro Asp Thr Val Lys Thr Leu
385                 390                 395                 400

Leu Lys Val Ser Lys Gly Gln Lys Met Asn Ala Gln Ala Ile Ala Leu
                405                 410                 415

Val Ala Cys Tyr Leu Arg Gly Gly Gly Gln Leu Asp Glu Asp Met Val
            420                 425                 430

Lys Ala Leu Gly Asp Ile Pro Leu Ser Tyr Leu Cys Asp Phe Ser Pro
        435                 440                 445

Gln Asp Leu His Ser Val Pro Ser Ser Val Met Trp Leu Val Gly Pro
    450                 455                 460

Gln Asp Leu Asp Lys Cys Ser Gln Arg His Leu Gly Leu Leu Tyr Gln
465                 470                 475                 480

Lys Ala Cys Ser Ala Phe Gln Asn Val Ser Gly Leu Glu Tyr Phe Glu
                485                 490                 495

Lys Ile Lys Thr Phe Leu Gly Gly Ala Ser Val Lys Asp Leu Arg Ala
            500                 505                 510

Leu Ser Gln His Asn Val Ser Met Asp Ile Ala Thr Phe Lys Arg Leu
        515                 520                 525

Gln Val Asp Ser Leu Val Gly Leu Ser Val Ala Glu Val Gln Lys Leu
    530                 535                 540

Leu Gly Pro Asn Ile Val Asp Leu Lys Thr Glu Glu Asp Lys Ser Pro
545                 550                 555                 560

Val Arg Asp Trp Leu Phe Arg Gln His Gln Lys Asp Leu Asp Arg Leu
                565                 570                 575

Gly Leu Gly Leu Gln Gly Gly Ile Pro Asn Gly Tyr Leu Val Leu Asp
            580                 585                 590

Phe Asn Val Arg Glu Ala Phe Ser Ser Arg Ala Ser Leu Leu Gly Pro
        595                 600                 605

Gly Phe Val Leu Ile Trp Ile Pro Ala Leu Leu Pro Ala Leu Arg Leu
    610                 615                 620

Ser
625


<210> SEQ ID NO 31
<211> LENGTH: 9
<212> TYPE: PRT
<213> ORGANISM: Artificial Sequence
<220> FEATURE:
<223> OTHER INFORMATION: Synthetic mesothelin peptide

<400> SEQUENCE: 31

Gly Gln Lys Met Asn Ala Gln Ala Ile
1               5


<210> SEQ ID NO 32
<211> LENGTH: 15
<212> TYPE: PRT
<213> ORGANISM: Artificial Sequence
<220> FEATURE:
<223> OTHER INFORMATION: 3D beta peptide clone from Mus musculus
```

<400> SEQUENCE: 32

Cys Ala Ser Ser Pro Gly Leu Gly Gly Ser Tyr Glu Gln Tyr Phe
1 5 10 15

<210> SEQ ID NO 33
<211> LENGTH: 45
<212> TYPE: DNA
<213> ORGANISM: Artificial Sequence
<220> FEATURE:
<223> OTHER INFORMATION: 3D beta nucleotide clone from Mus musculus

<400> SEQUENCE: 33
tgtgccagca gccctggact gggggatcc tatgaacagt acttc 45

<210> SEQ ID NO 34
<211> LENGTH: 15
<212> TYPE: PRT
<213> ORGANISM: Artificial Sequence
<220> FEATURE:
<223> OTHER INFORMATION: V beta 10 clone #1 peptide clone from Mus musculus

<400> SEQUENCE: 34

Cys Ala Ser Ser Gln Gly Leu Gly Ser Ser Tyr Glu Gln Tyr Phe
1 5 10 15

<210> SEQ ID NO 35
<211> LENGTH: 45
<212> TYPE: DNA
<213> ORGANISM: Artificial Sequence
<220> FEATURE:
<223> OTHER INFORMATION: V beta 10 clone #1 nucleotide clone from Mus musculus

<400> SEQUENCE: 35
tgtgccagca gccagggact ggggagctcc tatgaacagt acttc 45

<210> SEQ ID NO 36
<211> LENGTH: 14
<212> TYPE: PRT
<213> ORGANISM: Artificial Sequence
<220> FEATURE:
<223> OTHER INFORMATION: V beta 10 clone #2 peptide from Mus musculus

<400> SEQUENCE: 36

Cys Ala Ser Ser Tyr Ile Leu Gly Ala Tyr Glu Gln Tyr Phe
1 5 10

<210> SEQ ID NO 37
<211> LENGTH: 42
<212> TYPE: DNA
<213> ORGANISM: Artificial Sequence
<220> FEATURE:
<223> OTHER INFORMATION: V beta 10 clone #2 nucleotide from Mus musculus

<400> SEQUENCE: 37
tgtgccagca gctatatact gggggcctat gaacagtact tc 42

<210> SEQ ID NO 38
<211> LENGTH: 13
<212> TYPE: PRT
<213> ORGANISM: Artificial Sequence
<220> FEATURE:
<223> OTHER INFORMATION: V beta 10 clone #3 peptide from Mus musculus

<400> SEQUENCE: 38

```
Cys Ala Ser Ser Ser Trp Thr Val Tyr Glu Gln Tyr Phe
1               5                   10


<210> SEQ ID NO 39
<211> LENGTH: 39
<212> TYPE: DNA
<213> ORGANISM: Artificial Sequence
<220> FEATURE:
<223> OTHER INFORMATION: V beta 10 clone #3 nucleotide from Mus musculus

<400> SEQUENCE: 39

tgtgccagca gctcctggac agtctatgaa cagtacttc                            39


<210> SEQ ID NO 40
<211> LENGTH: 15
<212> TYPE: PRT
<213> ORGANISM: Artificial Sequence
<220> FEATURE:
<223> OTHER INFORMATION: V beta 10 clone #4 peptide from Mus musculus

<400> SEQUENCE: 40

Cys Ala Ser Ser Trp Thr Gly Ala Asn Thr Gly Gln Leu Tyr Phe
1               5                   10                  15


<210> SEQ ID NO 41
<211> LENGTH: 45
<212> TYPE: DNA
<213> ORGANISM: Artificial Sequence
<220> FEATURE:
<223> OTHER INFORMATION: V beta 10 clone #4 nucleotide from Mus musculus

<400> SEQUENCE: 41

tgtgccagca gctggacagg ggcaaacacc gggcagctct acttt                     45


<210> SEQ ID NO 42
<211> LENGTH: 9
<212> TYPE: PRT
<213> ORGANISM: Artificial Sequence
<220> FEATURE:
<223> OTHER INFORMATION: synthetic mesothelin peptide

<400> SEQUENCE: 42

Ile Ser Lys Ala Asn Val Asp Val Leu
1               5


<210> SEQ ID NO 43
<211> LENGTH: 9
<212> TYPE: PRT
<213> ORGANISM: Artificial Sequence
<220> FEATURE:
<223> OTHER INFORMATION: synthetic mesothelin peptide

<400> SEQUENCE: 43

Gly Gln Lys Met Asn Ala Gln Ala Ile
1               5


<210> SEQ ID NO 44
<211> LENGTH: 9
<212> TYPE: PRT
<213> ORGANISM: Artificial Sequence
<220> FEATURE:
<223> OTHER INFORMATION: synthetic mesothelin peptide

<400> SEQUENCE: 44

Ser Ala Phe Gln Asn Val Ser Gly Leu
1               5
```

<210> SEQ ID NO 45
<211> LENGTH: 9
<212> TYPE: PRT
<213> ORGANISM: Artificial Sequence
<220> FEATURE:
<223> OTHER INFORMATION: synthetic mesothelin peptide

<400> SEQUENCE: 45

Leu Leu Gly Pro Asn Ile Val Asp Leu
1               5

<210> SEQ ID NO 46
<211> LENGTH: 9
<212> TYPE: PRT
<213> ORGANISM: Artificial Sequence
<220> FEATURE:
<223> OTHER INFORMATION: synthetic mesothelin peptide

<400> SEQUENCE: 46

Glu Ile Pro Phe Thr Tyr Glu Gln Leu
1               5

<210> SEQ ID NO 47
<211> LENGTH: 9
<212> TYPE: PRT
<213> ORGANISM: Artificial Sequence
<220> FEATURE:
<223> OTHER INFORMATION: synthetic mesothelin peptide

<400> SEQUENCE: 47

Gly Ile Pro Asn Gly Tyr Leu Val Leu
1               5

<210> SEQ ID NO 48
<211> LENGTH: 1595
<212> TYPE: DNA
<213> ORGANISM: Homo sapiens

<400> SEQUENCE: 48
agaatcaaaa gaggaaacca acccctaaga tgagctttcc atgtaaattt gtagccagct 60
tccttctgat tttcaatgtt tcttccaaag gtgcagtctc caaagagatt acgaatgcct 120
tggaaacctg ggtgccttg ggtcaggaca tcaacttgga cattcctagt tttcaaatga 180
gtgatgatat tgacgatata aaatgggaaa aaacttcaga caagaaaaag attgcacaat 240
tcagaaaaga gaaagagact ttcaaggaaa aagatacata taagctattt aaaaatggaa 300
ctctgaaaat taagcatctg aagaccgatg atcaggatat ctacaaggta tcaatatatg 360
atacaaaagg aaaaaatgtg ttggaaaaaa tatttgattt gaagattcaa gagagggtct 420
caaaaccaaa gatctcctgg acttgtatca acacaaccct gacctgtgag gtaatgaatg 480
gaactgaccc cgaattaaac ctgtatcaag atgggaaaca tctaaaactt tctcagaggg 540
tcatcacaca caagtggacc accagcctga gtgcaaaatt caagtgcaca gcagggaaca 600
aagtcagcaa ggaatccagt gtcgagcctg tcagctgtcc agagaaaggt ctggacatct 660
atctcatcat tggcatatgt ggaggaggca gcctcttgat ggtctttgtg gcactgctcg 720
ttttctatat caccaaaagg aaaaaacaga ggagtcggag aaatgatgag gagctggaga 780
caagagccca cagagtagct actgaagaaa ggggccggaa gccccaccaa attccagctt 840
caacccctca gaatccagca acttcccaac atcctcctcc accacctggt catcgttccc 900
aggcacctag tcatcgtccc ccgcctcctg gacaccgtgt tcagcaccag cctcagaaga 960

```
ggcctcctgc tccgtcgggc acacaagttc accagcagaa aggcccgccc ctccccagac   1020

ctcgagttca gccaaaacct ccccatgggg cagcagaaaa ctcattgtcc ccttcctcta   1080

attaaaaaag atagaaactg tctttttcaa taaaaagcac tgtggatttc tgccctcctg   1140

atgtgcatat ccgtacttcc atgaggtgtt ttctgtgtgc agaacattgt cacctcctga   1200

ggctgtgggc cacagccacc tctgcatctt cgaactcagc catgtggtca acatctggag   1260

tttttggtct cctcagagag ctccatcaca ccagtaagga gaagcaatat aagtgtgatt   1320

gcaagaatgg tagaggaccg agcacagaaa tcttagagat ttcttgtccc ctctcaggtc   1380

atgtgtagat gcgataaatc aagtgattgg tgtgcctggg tctcactaca agcagcctat   1440

ctgcttaaga gactctggag tttcttatgt gccctggtgg acacttgccc accatcctgt   1500

gagtaaaagt gaaataaaag ctttgactag aaaaaaaaaa aaaaaaaaaa aaaaaaaaaa   1560

aaaaaaaaaa aaaaaaaaaa aaaaaaaaaa aaaaa                              1595
```

```
<210> SEQ ID NO 49
<211> LENGTH: 351
<212> TYPE: PRT
<213> ORGANISM: Homo sapiens

<400> SEQUENCE: 49

Met Ser Phe Pro Cys Lys Phe Val Ala Ser Phe Leu Leu Ile Phe Asn
1               5                   10                  15

Val Ser Ser Lys Gly Ala Val Ser Lys Glu Ile Thr Asn Ala Leu Glu
            20                  25                  30

Thr Trp Gly Ala Leu Gly Gln Asp Ile Asn Leu Asp Ile Pro Ser Phe
        35                  40                  45

Gln Met Ser Asp Asp Ile Asp Asp Ile Lys Trp Glu Lys Thr Ser Asp
    50                  55                  60

Lys Lys Lys Ile Ala Gln Phe Arg Lys Glu Lys Glu Thr Phe Lys Glu
65                  70                  75                  80

Lys Asp Thr Tyr Lys Leu Phe Lys Asn Gly Thr Leu Lys Ile Lys His
                85                  90                  95

Leu Lys Thr Asp Asp Gln Asp Ile Tyr Lys Val Ser Ile Tyr Asp Thr
            100                 105                 110

Lys Gly Lys Asn Val Leu Glu Lys Ile Phe Asp Leu Lys Ile Gln Glu
        115                 120                 125

Arg Val Ser Lys Pro Lys Ile Ser Trp Thr Cys Ile Asn Thr Thr Leu
    130                 135                 140

Thr Cys Glu Val Met Asn Gly Thr Asp Pro Glu Leu Asn Leu Tyr Gln
145                 150                 155                 160

Asp Gly Lys His Leu Lys Leu Ser Gln Arg Val Ile Thr His Lys Trp
                165                 170                 175

Thr Thr Ser Leu Ser Ala Lys Phe Lys Cys Thr Ala Gly Asn Lys Val
            180                 185                 190

Ser Lys Glu Ser Ser Val Glu Pro Val Ser Cys Pro Glu Lys Gly Leu
        195                 200                 205

Asp Ile Tyr Leu Ile Ile Gly Ile Cys Gly Gly Gly Ser Leu Leu Met
    210                 215                 220

Val Phe Val Ala Leu Leu Val Phe Tyr Ile Thr Lys Arg Lys Lys Gln
225                 230                 235                 240

Arg Ser Arg Arg Asn Asp Glu Glu Leu Glu Thr Arg Ala His Arg Val
                245                 250                 255

Ala Thr Glu Glu Arg Gly Arg Lys Pro His Gln Ile Pro Ala Ser Thr
```

```
            260                 265                 270

Pro Gln Asn Pro Ala Thr Ser Gln His Pro Pro Pro Pro Pro Gly His
        275                 280                 285

Arg Ser Gln Ala Pro Ser His Arg Pro Pro Pro Pro Gly His Arg Val
    290                 295                 300

Gln His Gln Pro Gln Lys Arg Pro Pro Ala Pro Ser Gly Thr Gln Val
305                 310                 315                 320

His Gln Gln Lys Gly Pro Pro Leu Pro Arg Pro Arg Val Gln Pro Lys
                325                 330                 335

Pro Pro His Gly Ala Ala Glu Asn Ser Leu Ser Pro Ser Ser Asn
            340                 345                 350


<210> SEQ ID NO 50
<211> LENGTH: 1098
<212> TYPE: DNA
<213> ORGANISM: Homo sapiens

<400> SEQUENCE: 50

atggccgtca tggctccccg aaccctcgtc ctgctactct cgggggctct ggccctgacc      60

cagacctggg cgggctctca ctccatgagg tatttcttca catccgtgtc ccggcccggc     120

cgcggggagc cccgcttcat cgcagtgggc tacgtggacg acacgcagtt cgtgcggttc     180

gacagcgacg ccgcgagcca gaggatggag ccgcgggcgc cgtggataga gcaggagggt     240

ccggagtatt gggacgggga gacacggaaa gtgaaggccc actcacagac tcaccgagtg     300

gacctgggga ccctgcgcgg ctactacaac cagagcgagg ccggttctca caccctccag     360

atgatgtttg gctgcgacgt ggggtcggac tggcgcttcc tccgcgggta ccaccagtac     420

gcctacgacg gcaaggatta catcgccctg aaagaggacc tgcgctcttg gaccgcggcg     480

gacatggcag ctcagaccac caagcacaag tgggaggcgg cccatgtggc ggagcagttg     540

agagcctacc tggagggcac gtgcgtggag tggctccgca gatacctgga gaacgggaag     600

gagacgctgc agcgcacgga cgcccccaaa acgcatatga ctcaccacgc tgtctctgac     660

catgaagcca ccctgaggtg ctgggccctg agcttctacc ctgcggagat cacactgacc     720

tggcagcggg atggggagga ccagacccag gacacggagc tcgtggagac caggcctgca     780

ggggatggaa ccttccagaa gtgggcggct gtggtggtgc cttctggaca ggagcagaga     840

tacacctgcc atgtgcagca tgagggtttg cccaagcccc tcaccctgag atgggagccg     900

tcttcccagc ccaccatccc catcgtgggc atcattgctg gcctggttct ctttggagct     960

gtgatcactg gagctgtggt cgctgctgtg atgtggagga ggaagagctc agatagaaaa    1020

ggagggagct actctcaggc tgcaagcagt gacagtgccc agggctctga tgtgtctctc    1080

acagcttgta aagtgtga                                                  1098


<210> SEQ ID NO 51
<211> LENGTH: 365
<212> TYPE: PRT
<213> ORGANISM: Homo sapiens

<400> SEQUENCE: 51

Met Ala Val Met Ala Pro Arg Thr Leu Val Leu Leu Leu Ser Gly Ala
1               5                   10                  15

Leu Ala Leu Thr Gln Thr Trp Ala Gly Ser His Ser Met Arg Tyr Phe
            20                  25                  30

Phe Thr Ser Val Ser Arg Pro Gly Arg Gly Glu Pro Arg Phe Ile Ala
        35                  40                  45
```

```
Val Gly Tyr Val Asp Asp Thr Gln Phe Val Arg Phe Asp Ser Asp Ala
    50                  55                  60

Ala Ser Gln Arg Met Glu Pro Arg Ala Pro Trp Ile Glu Gln Glu Gly
65                  70                  75                  80

Pro Glu Tyr Trp Asp Gly Glu Thr Arg Lys Val Lys Ala His Ser Gln
                85                  90                  95

Thr His Arg Val Asp Leu Gly Thr Leu Arg Gly Tyr Tyr Asn Gln Ser
            100                 105                 110

Glu Ala Gly Ser His Thr Leu Gln Met Met Phe Gly Cys Asp Val Gly
        115                 120                 125

Ser Asp Trp Arg Phe Leu Arg Gly Tyr His Gln Tyr Ala Tyr Asp Gly
    130                 135                 140

Lys Asp Tyr Ile Ala Leu Lys Glu Asp Leu Arg Ser Trp Thr Ala Ala
145                 150                 155                 160

Asp Met Ala Ala Gln Thr Thr Lys His Lys Trp Glu Ala Ala His Val
                165                 170                 175

Ala Glu Gln Leu Arg Ala Tyr Leu Glu Gly Thr Cys Val Glu Trp Leu
            180                 185                 190

Arg Arg Tyr Leu Glu Asn Gly Lys Glu Thr Leu Gln Arg Thr Asp Ala
        195                 200                 205

Pro Lys Thr His Met Thr His His Ala Val Ser Asp His Glu Ala Thr
    210                 215                 220

Leu Arg Cys Trp Ala Leu Ser Phe Tyr Pro Ala Glu Ile Thr Leu Thr
225                 230                 235                 240

Trp Gln Arg Asp Gly Glu Asp Gln Thr Gln Asp Thr Glu Leu Val Glu
                245                 250                 255

Thr Arg Pro Ala Gly Asp Gly Thr Phe Gln Lys Trp Ala Ala Val Val
            260                 265                 270

Val Pro Ser Gly Gln Glu Gln Arg Tyr Thr Cys His Val Gln His Glu
        275                 280                 285

Gly Leu Pro Lys Pro Leu Thr Leu Arg Trp Glu Pro Ser Ser Gln Pro
    290                 295                 300

Thr Ile Pro Ile Val Gly Ile Ile Ala Gly Leu Val Leu Phe Gly Ala
305                 310                 315                 320

Val Ile Thr Gly Ala Val Val Ala Ala Val Met Trp Arg Arg Lys Ser
                325                 330                 335

Ser Asp Arg Lys Gly Gly Ser Tyr Ser Gln Ala Ala Ser Ser Asp Ser
            340                 345                 350

Ala Gln Gly Ser Asp Val Ser Leu Thr Ala Cys Lys Val
        355                 360                 365
```

<210> SEQ ID NO 52
<211> LENGTH: 987
<212> TYPE: DNA
<213> ORGANISM: Homo sapiens

<400> SEQUENCE: 52

```
aatataagtg gaggcgtcgc gctggcgggc attcctgaag ctgacagcat tcgggccgag     60

atgtctcgct ccgtggcctt agctgtgctc gcgctactct ctctttctgg cctggaggct    120

atccagcgta ctccaaagat tcaggtttac tcacgtcatc cagcagagaa tggaaagtca    180

aatttcctga attgctatgt gtctgggttt catccatccg acattgaagt tgacttactg    240

aagaatggag agagaattga aaaagtggag cattcagact tgtctttcag caaggactgg    300
```

-continued

```
tctttctatc tcttgtacta cactgaattc acccccactg aaaaagatga gtatgcctgc    360

cgtgtgaacc atgtgacttt gtcacagccc aagatagtta agtgggatcg agacatgtaa    420

gcagcatcat ggaggtttga agatgccgca tttggattgg atgaattcca aattctgctt    480

gcttgctttt taatattgat atgcttatac acttacactt tatgcacaaa atgtagggtt    540

ataataatgt taacatggac atgatcttct ttataattct actttgagtg ctgtctccat    600

gtttgatgta tctgagcagg ttgctccaca ggtagctcta ggagggctgg caacttagag    660

gtggggagca gagaattctc ttatccaaca tcaacatctt ggtcagattt gaactcttca    720

atctcttgca ctcaaagctt gttaagatag ttaagcgtgc ataagttaac ttccaattta    780

catactctgc ttagaatttg ggggaaaatt tagaaatata attgacagga ttattggaaa    840

tttgttataa tgaatgaaac attttgtcat ataagattca tatttacttc ttatacattt    900

gataaagtaa ggcatggttg tggttaatct ggtttatttt tgttccacaa gttaaataaa    960

tcataaaact tgatgtgtta tctctta                                         987

<210> SEQ ID NO 53
<211> LENGTH: 119
<212> TYPE: PRT
<213> ORGANISM: Homo sapiens

<400> SEQUENCE: 53

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115
```

ENHANCED AFFINITY T CELL RECEPTORS AND METHODS FOR MAKING THE SAME

RELATED APPLICATION

This application is a divisional application of U.S. application Ser. No. 14/398,206, filed Oct. 31, 2014, which issued as U.S. Pat. No. 9,751,928, which is a 371 National Stage Application of International Application No. PCT/US2013/039316, filed May 2, 2013, which claims the benefit of U.S. Provisional Application No. 61/642,358, filed May 3, 2012. All of the above-identified applications are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360056_412D1_SEQUENCE_LISTING.txt. The text file is 125 KB, was created on Jul. 19, 2019, and is being submitted electronically via EFS-Web.

STATEMENT OF GOVERNMENT INTEREST

This invention was made with government support under CA018029 awarded by the National Institutes of Health. The government has certain rights in the invention.

BACKGROUND

Technical Field

The present disclosure relates to enhanced affinity T cell receptors (TCRs) and, more particularly, to using agonist selection of hematopoietic progenitor cells expressing an antigen specific TCRα to generate enhanced affinity TCRs, and to uses thereof.

Description of the Related Art

TCR gene therapy is an emerging treatment approach that can overcome many of the obstacles associated with conventional T cell adoptive immunotherapy, such as the extensive time and labor required to isolate, characterize, and expand tumor antigen-specific T cell clones (Schmitt, Ragnarsson, and Greenberg, *Hum. Gene Ther.* 20:1240-1248, 2009). Further benefits of gene therapy include the ability to utilize defined populations of T cells capable of long-term persistence in vivo (Berger et al., *J. Clin. Invest.* 118:294-305, 2008; Hinrichs et al., *Proc. Nat'l. Acad. Sci. USA* 106:17469-17474, 2009). Such T cells can be transduced with genes encoding well-characterized TCRs that have a high affinity for tumor antigens, thereby increasing the likelihood of mediating an antitumor effect. Indeed, a recent report of therapy targeting advanced B cell leukemia with genetically modified T cells expressing a high affinity chimeric receptor targeting a self/tumor-antigen has highlighted the potential of using engineered high avidity T cells for the treatment of leukemia (Kalos et al., *Sci. Transl. Med.* 3:95ra73, 2011). However, since most tumor antigens targeted by T cell immunotherapy are over-expressed self-proteins, high affinity T cells specific for these antigens are generally subject to negative selection in the thymus. Therefore, one significant limitation of T cell based immunotherapies in general is the limited availability of T cells expressing an endogenous TCR with sufficiently high affinity for non-mutated tumor antigens.

Several strategies have been developed to enhance the affinity of TCRs intended for use in TCR gene therapy (Richman and Kranz, *Biomol. Eng.* 24:361-373, 2007; Udyavar et al., *J. Immunol.* 182:4439-4447, 2009; Zhao et al., *J. Immunol.* 179:5845-5854, 2007). These approaches generally entail the generation of libraries of TCR mutants that have undergone rounds of mutagenesis and subsequent screening for mutations that confer higher affinity for the target peptide/MHC ligand. Mutations are generally made in the CDR regions that are known to interact with peptide/MHC. CDR1 and CDR2 regions predominantly make contact with the MHC molecule, while the hypervariable CDR3 region primarily contacts the peptide (Wucherpfennig et al., *Cold Spring Harbor Perspectives in Biology* 2:a005140-a005140, 2010). Site-directed mutagenesis strategies generally target selected portions of all three of these regions, but still are not always successful in generating a higher affinity variant, and the improvements are limited to changes only in the specifically targeted regions. Moreover, mutations introduced into the MHC contact residues have the risk of potentially increasing the affinity of the TCR for MHC while decreasing the overall specificity of the receptor for its cognate peptide. Ideally, most mutations introduced to enhance the affinity of a TCR would be restricted to the CDR3 region for this reason. However, current methodologies are limited in the capacity to generate CDR3 diversity, because site-directed mutagenesis is constrained by the original length of the CDR3 region.

Given the difficulty of isolating high affinity T cells that recognize relevant tumor associated antigens, there is a continuing need for alternative methods for generating enhanced affinity TCRs.

BRIEF SUMMARY

In one aspect, the present disclosure provides a method for generating enhanced affinity TCRs comprising: a) contacting hematopoietic progenitor cells with stromal cells and a peptide antigen, under conditions and for a time sufficient to induce differentiation of hematopoietic progenitor cells into DN TCRαβ$^+$ thymocytes, wherein the hematopoietic progenitor cells comprise a non-endogenous nucleic acid sequence encoding a TCRα chain from a parent TCR specific for the peptide antigen, and wherein the stromal cells comprise a non-endogenous nucleic acid sequence encoding Delta-like-1 or Delta-like-4 and a nucleic acid sequence encoding an MHC molecule; b) isolating nucleic acid sequences encoding the various TCRβ chains from the DN TCRαβ$^+$ thymocytes and introducing the nucleic acid sequences encoding the TCRβ chains into cells that are capable of expressing a TCR on the cell surface and comprising the nucleic acid sequence encoding the TCRα chain from step a); and identifying enhanced affinity TCRs (e.g., by detecting or selecting high affinity TCRαβ candidates by an MHC tetramer assay, and then measuring binding affinity as compared to a parent TCRαβ.

In further aspects, enhanced affinity TCRs generated by methods disclosed herein are provided, which may be cell-bound or in soluble form, and may further be codon optimized to enhance expression in T cells.

In still further aspects, enhanced affinity TCRs of the present disclosure may be used to treat a disease (such as cancer, infectious disease, or autoimmune disease) in a subject by administering a composition comprising the enhanced affinity TCRs. In further embodiments, enhanced affinity TCRs of the instant disclosure may be used in diagnostic methods or imaging methods, including these methods used in relation to the indications or conditions identified herein.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 3A-3C show B6 thymocytes that were sorted for CD4$^-$CD8$^-$ CD117$^+$CD44$^+$ DN1 and DN2 progenitor cells and transduced with the TCR+ chain of the affinity enhanced WT1 specific TCR 3D clone, and cultured on OP9-DL1 cells expressing MHC Class I H-2Db molecule in the presence or absence of 1 μM of WT1 peptide RMFPNAPYL (SEQ ID NO:2). (a) On day 16 of culture, transduced (hCD2$^+$) and untransduced (hCD2$^-$) cells were analyzed by flow cytometry. (b) On day 21 of OP9-DL1 culture in the presence of 1 μM WT1 peptide RMFPNAPYL (SEQ ID NO:2), DN TCRαβ$^+$ cells were sorted according to the scheme indicated. (c) Sorted cells were lysed, DNA was isolated, and PCR was performed using a Vb10-specific forward primer and a Cb2-specific reverse primer. The Vb10 PCR product was then directionally TOPO-cloned into vector pENTR/D-TOPO, transferred to the retroviral vector MigR1-attR using Gateway® technology, and retroviral supernatant was generated and used to transduce murine 58$^{-/-}$ cells for library screening as described.

FIGS. 4A-4C show the results of a retroviral TCRβ library used to transduce CD8$^+$3Dα$^+$58$^{-/-}$ cells. (a) Transduced cells were initially sorted on GFP expression only (data not shown), followed by two additional sorts on GFP and high MHC-WT1 peptide tetramer expression as indicated. Sorted 58$^{-/-}$ cells were also analyzed for staining with the non-specific, but MHC H-2Db-peptide tetramer specific for GP33 as a control for non-specific tetramer binding. (b) Sequence analysis of isolated TCRβ chains. (c) Four candidate TCRβ chains were identified by sequence analysis, and were transferred back into MigR1-attR retroviral vector. Retroviral supernatant was generated, and used to transduce CD8$^+$3Dα$^+$ 58$^{-/-}$ cells.

DETAILED DESCRIPTION

Figure 1A:
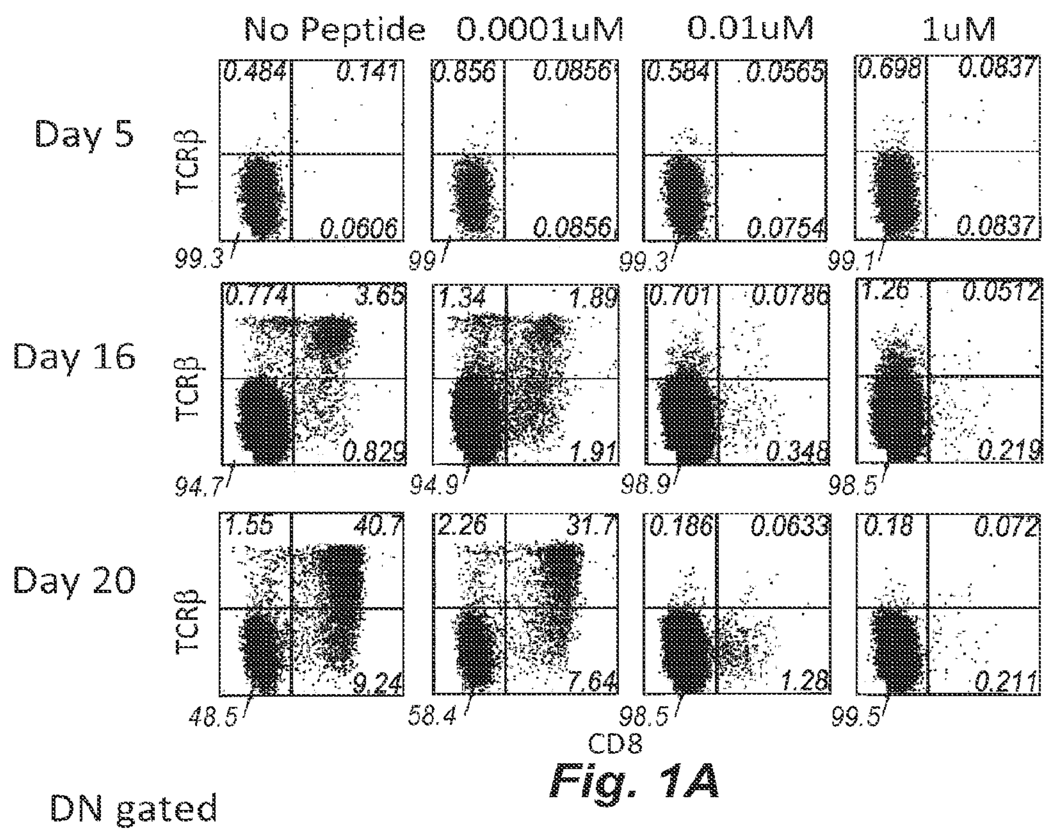
FIGS. 1A-1D shows the results of thymocytes from OT-1 transgenic mice sorted for TCRβTCRγδ$^-$CD4$^-$CD8$^-$ CD117$^+$CD44$^+$ DN1 and DN2 progenitor cells and cultured on OP9-DL1 cells expressing MHC Class I H-2Kb molecule for 20 days in the presence of various concentrations of ovalbumin peptide SIINFEKL (SEQ ID NO:1), as indicated. (a, b, c) Cultures were analyzed by flow cytometry at the time points indicated. (d) Total cellularity of each culture was determined on day 20 of culture.

The instant disclosure provides methods and compositions for generating enhanced or high affinity TCRs, in which the TCRα chain from an antigen-specific TCR is used to select de novo generated TCRβ chains that pair with an antigen-specific TCRα chain during T cell development in vitro, to form new, enhanced affinity receptors that can advantageously drive T cell maturation independent of negative selection through a novel selection process in order to target an antigen of interest.

In one aspect, the present disclosure provides a method for generating enhanced affinity T cell receptors (TCRs) by culturing hematopoietic progenitor cells (containing a non-endogenous nucleic acid sequence encoding an antigen specific TCRα chain) with stromal cells (containing a non-endogenous nucleic acid sequence encoding Delta-like-1 or Delta-like-4 and a nucleic acid sequence encoding an MHC molecule) in the presence of a peptide antigen, which will induce differentiation of the hematopoietic progenitor cells into DN TCRαβ$^+$ thymocytes. Then nucleic acid sequences encoding various TCRβ chains from the DN TCRαβ$^+$ thymocytes are isolated and introduced into cells that are capable of expressing a TCR on the cell surface and also express the TCRα chain noted above. Finally, enhanced affinity TCRs are identified by comparing the binding affinity of candidate TCRαβ with the parent TCRαβ.

Additionally, this disclosure provides enhanced affinity TCRs generated using such methods, as well as compositions and methods for using the enhanced affinity TCRs of this disclosure in various therapeutic applications, including the treatment of a disease in subject (e.g., cancer, infectious disease, autoimmune disease).

Prior to setting forth this disclosure in more detail, it may be helpful to an understanding thereof to provide definitions of certain terms to be used herein. Additional definitions are set forth throughout this disclosure.

In the present description, the terms "about" and "consisting essentially of" mean±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have" and "comprise" are used synonymously, which terms and variants thereof are intended to be construed as non-limiting.

"T cell receptor" (TCR) refers to a molecule found on the surface of T cells (or T lymphocytes) that, in association with CD3, is generally responsible for recognizing antigens bound to major histocompatibility complex (MHC) molecules. The TCR has a disulfide-linked heterodimer of the highly variable α and β chains (also known as TCRα and TCRβ, respectively) in most T cells. In a small subset of T cells, the TCR is made up of a heterodimer of variable γ and δ chains (also known as TCRγ and TCRδ, respectively). Each chain of the TCR is a member of the immunoglobulin superfamily and possesses one N-terminal immunoglobulin variable domain, one immunoglobulin constant domain, a transmembrane region, and a short cytoplasmic tail at the C-terminal end (see Janeway et al., *Immunobiology: The Immune System in Health and Disease,* 3rd Ed., Current Biology Publications, p. 4:33, 1997). TCR as used in the present disclosure may be from various animal species, including human, mouse, rat, or other mammals. TCRs may be cell-bound or in soluble form.

TCRs and binding domains thereof of this disclosure can be "immunospecific" or capable of binding to a desired degree, including "specifically or selectively binding" a target while not significantly binding other components present in a test sample, if they bind a target molecule with an affinity or $K_a$ (i.e., an equilibrium association constant of a particular binding interaction with units of 1/M) of, for example, greater than or equal to about $10^5$ $M^{-1}$, $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, $10^{12}$ $M^{-1}$, or $10^{13}M^{-1}$. "High affinity" binding domains refers to those binding domains with a $K_a$ of at least $10^7$ $M^{-1}$, at least $10^8$ $M^{-1}$, at least $10^9$ $M^{-1}$ at least $10^{10}$ $M^{-1}$, at least $10^{11}$ $M^{-1}$, at least $10^{12}$ $M^{-1}$, at least $10^{11}$ $M^{-1}$, at least $10^{13}$ $M^{-1}$, or greater. Alternatively, affinity may be defined as an equilibrium dissociation constant ($K_d$) of a particular binding interaction with units of M (e.g., $10^{-5}$ M to $10^{-13}$ M). Affinities of TCRs and binding domain polypeptides according to the present disclosure can be readily determined using conventional techniques (see, e.g., Scatchard et al., *Ann. N.Y. Acad. Sci.* 51:660, 1949; and U.S. Pat. Nos. 5,283,173 and 5,468,614; Biacore® analysis, or the equivalent). Therefore, "enhanced affinity T cell receptor" (enhanced affinity TCR) refers to a selected or engineered TCR with stronger binding to a target antigen than the wild type (or parent) TCR. Enhanced affinity may be indicated by a TCR with a Ka (equilibrium association constant) for the target antigen higher than that of the wild type (also called parent or original) TCR, a TCR with a $K_d$ (dissociation constant) for the target antigen less than that of the wild type (also called parent or original) TCR, or with an off-rate ($K_{off}$) for the target antigen less than that of the wild type (or parent) TCR.

"Major histocompatibility complex molecules" (MHC molecules) refer to glycoproteins that deliver peptide antigens to a cell surface. MHC class I molecules are heterodimers consisting of a membrane spanning a chain (with three a domains) and a non-covalently associated β2 microglobulin. MHC class II molecules are composed of two transmembrane glycoproteins, α and β both of which span the membrane. Each chain has two domains. MHC class I molecules deliver peptides originating in the cytosol to the cell surface, where peptide:MHC complex is recognized by $CD8^+$ T cells. MHC class II molecules deliver peptides originating in the vesicular system to the cell surface, where they are recognized by $CD4^+$ T cells. An MHC molecule may be from various animal species, including human, mouse, rat, or other mammals.

A "hematopoietic progenitor cell" is a cell derived from hematopoietic stem cells or fetal tissue that is capable of further differentiation into mature cells types (e.g., cells of the T cell lineage). In a particular embodiment, $CD24^{lo}$ $Lin^-CD117^+$ hematopoietic progenitor cells are used. As defined herein, hematopoietic progenitor cells may include embryonic stem cells, which are capable of further differentiation to cells of the T cell lineage. Hematopoietic progenitor cells may be from various animal species, including human, mouse, rat, or other mammals.

A "thymocyte progenitor cell" or "thymocyte" is a hematopoietic progenitor cell present in the thymus.

"Hematopoietic stem cells" refer to undifferentiated hematopoietic cells that are capable of essentially unlimited propagation either in vivo or ex vivo and capable of differentiation to other cell types including cells of the T cell lineage. Hematopoietic stem cells may be isolated, for example, but not limited to, from fetal liver, bone marrow, cord blood.

"Cells of T cell lineage" refer to cells that show at least one phenotypic characteristic of a T cell or a precursor or progenitor thereof that distinguishes the cells from other lymphoid cells, and cells of the erythroid or myeloid lineages. Such phenotypic characteristics can include expression of one or more proteins specific for T cells (e.g., $CD8^+$), or a physiological, morphological, functional, or immunological feature specific for a T cell. For example, cells of the T cell lineage may be progenitor or precursor cells committed to the T cell lineage; $CD25^+$ immature and inactivated T cells; cells that have undergone CD4 or CD8 linage commitment; thymocyte progenitor cells that are $CD4^+CD8^+$ double positive; single positive $CD4^+$ or $CD8^+$; TCRαβ or TCR γδ; or mature and functional or activated T cells.

"Stromal cells" are connective tissue cells of any organ. In a particular embodiment, the stromal cells are bone marrow stromal cells. Examples of stromal cell lines that can be engineered to express DLL1 or DLL4 include the mouse stromal cell line MS5 (Itoh et al., *Exp. Hematol.* 17:145-153, 1989) and S17, and the human stromal cell lines HGS2.11, HGS2.52, HGS.18, HGS3.30, HGS3.65, HGS.3.66, HGS3.103, and HGS3.114 (available from Human Genome Sciences Inc., MD, see U.S. Published Pat. Appl. No. 2002/0001826). In a particular embodiment, OP9 cells (Kodama et al., *Exp. Hematol.* 22:979-984, 1994; available from RIKEN cell depository) are used. OP9 cells expressing DLL1 and DLL4 have been previously described (see, e.g., Schmitt et al., *Immunity* 17:749-756, 2002; U.S. Pat. No. 7,575,925)

"Double negative TCRαβ thymocytes" (DN TCRαβ thymocytes) refer to a population of thymocytes that do not express the CD4 and CD8 co-receptors, but do express TCRα and β chains.

"Peptide antigen" refers to an amino acid sequence, ranging from about 7 amino acids to about 25 amino acids in length, that is specifically recognized by a TCR, or binding domains thereof, as an antigen, and which may be derived from or based on a fragment of a longer target biological molecule (e.g., polypeptide, protein) or derivative thereof. An antigen may be expressed on a cell surface, within a cell, or as an integral membrane protein. An antigen may be a host-derived (e.g., tumor antigen, autoimmune antigen) or have an exogenous origin (e.g., bacterial, viral).

"Nucleic acid sequence", or polynucleotides, may be in the form of RNA or DNA, which includes cDNA, genomic DNA, and synthetic DNA. The nucleic acid sequence may be double stranded or single stranded, and if single stranded, may be the coding strand or non-coding (anti-sense strand). A coding sequence may be identical to the coding sequence known in the art or may be a different coding sequence, which, as the result of the redundancy or degeneracy of the genetic code, or by splicing, encodes the same polypeptide.

"Non-endogenous" refers to a molecule (e.g., nucleic acid sequence) that is not present in the host cell(s)/sample into which a molecule is introduced, for example, recombinantly introduced. A non-endogenous molecule may be from the same species or a different species.

Notch ligands "Delta-like-1" (DL1 or DLL1) and "Delta-like-4" (DL4 or DLL4) are homologs of the Notch Delta ligand and are members of the delta/serrate/jagged protein family. They play a role in mediating cell fate decisions during hematopoiesis and may play a role in cell-to-cell communication. Exemplary Delta-like-1 sequences include Genbank Accession No. NM_005618.3 (SEQ ID NO:3) and NP_005609.3 (SEQ ID NO:4) (*Homo sapiens* transcript and protein sequences, respectively) and Genbank Accession No. NM_007865.3 (SEQ ID NO:5) and NP_031891.2 (SEQ ID NO:6) (*Mus musculus* transcript and protein sequences, respectively). Exemplary Delta-like-4 sequences include Genbank Accession No. NM_019074.3 (SEQ ID NO:7) and NP_061947.1 (SEQ ID NO:8) (*Homo sapiens* transcript and protein sequences, respectively) and Genbank Accession No. NM_019454.3 (SEQ ID NO:9) and NP_062327.2 (SEQ ID NO:10) (*Mus musculus* transcript and protein sequences, respectively). Notch ligands are commercially available or can be produced by standard recombinant DNA techniques and purified to various degrees.

"Embryonic stem cells" or "ES cells" or "ESCs" refer to undifferentiated embryonic stem cells that have the ability to integrate into and become part of the germ line of a developing embryo. Embryonic stem cells are capable of differentiating into hematopoietic progenitor cells. Embryonic stem cells that are suitable for use herein include cells from the J1 ES cell line, 129J ES cell line, murine stem cell line D3 (American Type Culture Collection catalog #CRL 1934), the R1 or E14K cell lines derived from 129/Sv mice, cell lines derived from Balb/c and C57B1/6 mice, and human embryonic stem cells (e.g. from WiCell Research Institute, WI; or ES cell International, Melbourne, Australia).

"WT1" refers to Wilm's tumor 1, a transcription factor that contains four zinc-finger motifs at the C-terminus and a proline/glutamine-rich DNA binding domain at the N-terminus. WT1 has an essential role in the normal development of the urogential system and is mutated in a small subset of patients with Wilm's tumors. High expression of WT1 has been observed in various cancers, including, breast cancer, ovarian cancer, acute leukemias, vascular neoplasms, melanomas, colon cancer, lung cancer, thyroid cancer, bone and soft tissue sarcoma, and esophageal cancer. Alternative splicing has been noted for WT1. Exemplary WT1 sequences include Genbank Accession Nos: NM_000378.4 (SEQ ID NO:11) (human transcript), NP_000369.3 (SEQ ID NO:12) (human protein); NM_024424.3 (SEQ ID NO:13) (human transcript), NP_077742.2 (SEQ ID NO:14) (human protein); NM_024426.4 (SEQ ID NO:15) (human transcript), NP_077744.3 (SEQ ID NO:16); NM_001198552.1 (SEQ ID NO:17), NP_001185481.1 (SEQ ID NO:18) (human protein); NM_001198551.1 (SEQ ID NO:19) (human transcript), NP_001185480.1 (SEQ ID NO:20) (human protein); NM_144783.2 (SEQ ID NO:21) (mouse transcript), and NP_0659032.3 (SEQ ID NO:22) (mouse protein).

"Mesothelin" (MSLN) refers to a gene that encodes a precursor protein that is cleaved into two products, megakaryocyte potentiating factor and mesothelin. Megakaryocyte potentiation factor functions as a cytokine that can stimulate colony formation in bone marrow megakaryocytes. Mesothelian is a glycosylphosphatidylinositol-anchored cell-surface protein that may function as a cell adhesion protein. This protein is overexpressed in epithelial mesotheliomas, ovarian cancers and in specific squamous cell carcinomas. Alternative splicing results in multiple transcript variants. Exemplary mesothelin sequences include Genbank Accession Nos: NM_001177355.1 (SEQ ID NO:23), NP_001170826.1 (SEQ ID NO:24) (human transcript and pre-protein sequences, respectively); NM_005823.5 (SEQ ID NO:25), NP_005814.2 (SEQ ID NO:26) (human transcript and pre-protein sequences, respectively); NM_013404.4 (SEQ ID NO:27), NP_037536.2 (SEQ ID NO:28) (human transcript and pre-protein sequences, respectively); NM_018857.1 (SEQ ID NO:29), NP_061345.1 (SEQ ID NO:30) (mouse transcript and precursor protein sequences, respectively).

"MHC-peptide tetramer staining" refers to an assay used to detect antigen-specific T cells, which features a tetramer of MHC molecules, each comprising an identical peptide having an amino acid sequence that is cognate (e.g., identical or related to) at least one antigen, wherein the complex is capable of binding T cells specific for the cognate antigen. Each of the MHC molecules may be tagged with a biotin molecule. Biotinylated MHC/peptides are tetramerized by the addition of streptavidin, which is typically fluorescently labeled. The tetramer may be detected by flow cytometry via the fluorescent label. In certain embodiments, an MHC-peptide tetramer assay is used to detect or select high affinity TCRs of the instant disclosure.

Methods for Generating Enhanced Affinity TCRs

By way of background, during T cell development in the thymus, progenitor thymocytes are subjected to a number of TCR-mediated checkpoints. The first of these is termed β-selection, and occurs at double negative 3 (DN3) stage of murine T cell development. DN3 cells that produce a successful rearrangement at the Tcrb gene locus can express TCRβ protein at the cell surface paired with the invariant pre-Tα protein. This receptor is called the Pre-TCR, and it signals in a ligand-independent fashion to promote proliferation, differentiation of αβ lineage cells to the CD4/CD8 double positive (DP) stage, and rearrangement at the Tcra gene locus (Boehmer et al., *Curr. Opin. Immunol.* 11:135-142, 1999). While the TCRα locus is inactive and closed to TCR gene rearrangements prior to β-selection, both the TCRγ and δ loci also undergo rearrangements at the DN3 stage of development, and successful rearrangements at both these loci results in the expression of a mature γδ-TCR that can provide signals that drive differentiation towards the γδ T cell lineage—γδ T cells do not differentiate through a DP stage during development, and generally remain DN or CD8αα+. The αβ/γδ cell fate decision is determined by the strength of the TCR signal at this stage of development, as the developing T cell distinguishes between a pre-TCR signal and a γδ TCR signal by the stronger signal associated with the mature γδ TCR (Pennington, Silva-Santos, and Hayday, *Curr. Opin. Immunol.* 17:108-115, 2005). Interestingly, many αβ TCR transgenic mice have a large population of mature $CD24^-$ TCRαγ positive CD4/CD8 double negative (DN) cells in the thymus, which have been shown to represent "γδ wanna-be" cells that develop as a result of the stronger signal from the mature αγ transgenic TCR at the β-selection checkpoint (Egawa et al., *PLOS ONE* 3:1512, 2000).

Disclosed herein is a method for generating enhanced affinity TCRs, wherein ectopic expression of an antigen-specific TCRα chain prior to β-selection allows the development of T cells expressing a high affinity TCR for the same antigen when differentiated in the presence of the cognate antigen during in vitro T cell differentiation. Using this method, T cells expressing high affinity receptors bypass negative selection by adopting a DN TCRαβ$^+$ lineage fate in response to agonist signals at the DN3 stage of T cell development.

In certain embodiments, the present disclosure provides a method for generating enhanced affinity TCRs comprising: a) contacting hematopoietic progenitor cells with stromal cells and a peptide antigen, under conditions and for a time sufficient to induce differentiation of hematopoietic progenitor cells into DN TCRαγ$^+$ thymocytes, wherein the hematopoietic progenitor cells comprise a non-endogenous nucleic acid sequence encoding a TCRα chain from a parent TCR specific for the peptide antigen, and wherein the stromal cells comprise a non-endogenous nucleic acid sequence encoding Delta-like-1 or Delta-like-4 and a nucleic acid sequence encoding an WIC molecule; b) isolating nucleic acid sequences encoding the various TCRβ chains from the DN TCRαβ$^+$ thymocytes and introducing the nucleic acid sequences encoding the TCRβ chains into cells that are capable of expressing a TCR on the cell surface and comprise the nucleic acid sequence encoding the TCRα chain from step a); and identifying enhanced affinity TCR (e.g., by detecting or selecting high affinity TCRαβ candidates by an WIC tetramer assay, and then measuring binding affinity as compared to a parent TCRαβ.

In certain embodiments, hematopoietic progenitor cells comprise thymocyte progenitor cells or embryonic stem cells. In other embodiments, hematopoietic progenitor cells are derived from fetal liver tissue. In further embodiments, hematopoietic progenitor cells comprise hematopoietic stem cells that are derived or originate from bone marrow, cord blood, or peripheral blood. In yet other embodiments, hematopoietic progenitor cells are derived from human, mouse, rat, or other mammals. In particular embodiments, CD24$^{lo}$ Lin$^-$ CD117$^+$ thymocyte progenitor cells are used.

The hematopoietic progenitor cells have been modified to comprise a non-endogenous nucleic acid sequence encoding a TCRα chain from a parent TCR specific for the peptide antigen. In a specific embodiment, the TCRβ chain is also isolated from the parent TCR. Cloning of TCRα and β chains may be performed using standard molecular biology techniques that are known in the art. Methods for cloning TCR chains are known in the art (see, e.g., Walchli et al., *PLoS ONE* 6:e27930, 2011; Birkholz et al., *J. Immunol. Methods* 346:45-54, 2009; Kurokawa et al., *Clin. Exp. Immunol.* 123:340-345, 2001).

A "stromal cell" is a connective tissue cell of any organ. Stromal cells that may be used according to the invention include human and mouse stromal cells. Examples of stromal cell lines that can be engineered to express DL1 or DL4 include the mouse stromal cell line MS5 (Itoh et al., *Exp. Hematol.* 17:145-153, 1989) and S17, and the human stromal cell lines HGS2.11, HGS2.52, HGS.18, HGS3.30, HGS3.65, HGS.3.66, HGS3.103, and HGS3.114 (available from Human Genome Sciences Inc., MD; see U.S. Published Pat. Appl. No. 2002/0001826). In certain embodiments, stromal cells are bone marrow stromal cells. In further embodiments, OP9 cells are used.

In certain embodiments, stromal cells comprise non-endogenous nucleic acid sequences encoding DL1, such as human DL1. Exemplary Delta-like-1 sequences include Genbank Accession No. NM_005618.3 (SEQ ID NO:3) and NP_005609.3 (SEQ ID NO:4) (*Homo sapiens* transcript and protein sequences, respectively) and Genbank Accession No. NM_007865.3 (SEQ ID NO:5) and NP_031891.2 (SEQ ID NO:6) (*Mus musculus* transcript and protein sequences, respectively). In certain embodiments, stromal cells comprise non-endogenous nucleic acid sequences encoding DL4, such as human DL4. Exemplary Delta-like-4 sequences include Genbank Accession No. NM_019074.3 (SEQ ID NO:7) and NP_061947.1 (SEQ ID NO:8) (*Homo sapiens* transcript and protein sequences, respectively) and Genbank Accession No. NM_019454.3 (SEQ ID NO:9) and NP_062327.2 (SEQ ID NO:10) (*Mus musculus* transcript and protein sequences, respectively). Notch ligands are commercially available or can be produced by standard recombinant DNA techniques and purified to various degrees.

In still further embodiments, stromal cells are OP9 cells expressing DL1, such as human DL1. OP9 cells expressing DL1 and DL4 have been previously described (Schmitt et al., *Immunity:* 17:749-756, 2002; U.S. Pat. No. 7,575,925).

In certain embodiments, stromal cells also comprise a nucleic acid sequence encoding an MHC molecule. In particular embodiments, stromal cells comprise a nucleic acid sequence encoding an MHC Class I molecule, and may optionally also comprise a nucleic acid sequence encoding a β2 microglobulin. The MHC Class I and β2 microglobulin molecules may be derived from human, mouse, rat, or other mammalian MHC Class I molecules, whose genes and protein sequences are known in the art. In other embodiments, the stromal cells comprise a nucleic acid sequence encoding an MHC Class II molecule. The MHC Class II molecule may be derived from human, mouse, rat, or other mammalian MHC molecules, whose genes and protein sequences are known in the art.

A given T cell will recognize a peptide antigen only when it is bound to a host cell's MEW molecule (MHC-restricted antigen recognition). A parent TCR with specificity for a known peptide antigen is selected for enhancement of the TCR affinity using the disclosed methods. Therefore, an MHC molecule that binds the particular peptide antigen is also selected and expressed in the stromal cells to allow MHC-restricted antigen recognition in the disclosed in vitro system. Methods for identifying an MHC molecule that binds a peptide antigen are known in the art (see, e.g., Akatsuka et al., *Tissue Antigens* 59:502-511, 2002). In certain embodiments, an MHC molecule comprises HLA-A2 and beta-2 microglobulin, preferably of human origin, which can bind to, for example, the WT1 peptide RMFPNAPYL (SEQ ID NO:2). In other embodiments, an MHC molecule comprises mouse H-2D$^b$, which can bind to, for example, the WT1 peptide RMFPNAPYL or various mesothelin peptides as disclosed in FIG. 3A of Hung et al., *Gene Therapy* 14:921-929, 2007, or H-2K$^b$ (in particular, the peptides of Hung et al. are incorporated herein by reference) which can bind to, for example, various mesothelin peptides as disclosed in FIG. 3A of Hung et al.

A peptide antigen used in the disclosed methods refers to a peptide sequence of an antigen, or target biological molecule (e.g., a polypeptide, protein), to which the parent TCR specifically binds. A peptide sequence may be derived from an antigen that is expressed on the cell surface, within a cell, or that is an integral membrane protein. The antigen may be a host-derived antigen (e.g., a tumor/cancer antigen, and autoimmune antigen), or an exogenous antigen (e.g., viral, bacterial, protozoan antigen). A tumor or cancer antigen may be derived from various cancers, such as those noted herein. In some embodiments, a cancer antigen comprises a leukemia antigen. In certain embodiments, a peptide antigen is derived from Wilm's tumor 1 (WT1), such as a WT1 peptide comprising the amino acid sequence RMFPNAPYL (SEQ ID NO:2). In other embodiments, a peptide antigen is derived from mesothelin, such as mesothelin peptides disclosed in FIG. 3A of Hung et al., *Gene Therapy* 14:921-929, 2007. In some embodiments, the mesothelin peptide comprises the amino acid sequence GQKMNAQAI (SEQ ID NO:31). Autoimmune antigens are antigens that are recognized by autoreactive TCRs specific for self-antigens, with the ensuing immune effector functions causing autoimmune disease, exacerbating autoimmune disease, contributing to progression of autoimmune disease, causing or worsing symptoms associated with autoimmune disease. For example, autoreactive TCRs specific for a collagen peptide may be useful for suppressive gene therapy of Tregs in rheumatoid arthritis. Autoimmune antigens may also be antigens located on other immune cells that cause autoimmune disease or mediate symptoms of autoimmune disease (e.g., B cells that produce autoantibodies). For example, CD20 peptide antigens may be useful for generating enhanced affinity TCRs that target B cells involved in or associated with rheumatoid arthritis. A peptide antigen may be added to a culture system to hematopoietic progenitor cells and stromal cells as described herein. Alternatively, stromal cells comprising a nucleic acid sequence encoding a peptide antigen of interest may be used to express such antigen in the cell culture. Without wishing to be bound by theory, a peptide antigen, whether added as an exogenous peptide antigen to the culture system or expressed by stromal cells, complexes with a MHC molecule expressed by the stromal cells to form an MHC-peptide antigen complex. MHC-peptide antigen complex allows for MHC-restricted peptide antigen recognition by TCRs in the culture system. In certain embodiments, OP9 cells are transduced with a nucleic acid sequence to express the WT1 antigen peptide RMFPNAPYL (SEQ ID NO:2). In other embodiments, OP9 cells are transduced with a nucleic acid sequence to express the mesothelin antigen peptide GQKMNAQAI (SEQ ID NO:31).

Peptides that bind to MHC class I molecules are generally from about 7 to about 10 amino acids in length. Peptides that bind to MHC class II molecules are variable in length, usually about 10-25 amino acids long. In certain embodiments, parent TCR's peptide antigen specificity is known. In other embodiments, the parent TCR's peptide antigen specificity needs to be determined using methods known in the art (Borras et al., *J. Immunol. Methods* 267:79-97, 2002; Hiemstra et al., *Cur. Opin. Immunol.* 12:80-4, 2000). For example, if a target antigen of a parent TCR is known, though not a specific peptide sequence, peptide libraries derived from the target antigen polypeptide sequence may be used for screening and identifying the specific peptide antigen for the parent TCR.

A "vector" is a nucleic acid molecule that is capable of transporting another nucleic acid. Vectors may be, for example, plasmids, cosmids, viruses, or phage. An "expression vector" is a vector that is capable of directing the expression of a protein encoded by one or more genes carried by the vector when it is present in the appropriate environment.

"Retroviruses" are viruses having an RNA genome. "Gammaretrovirus" refers to a genus of the retroviridae family. Exemplary gammaretroviruses include, but are not limited to, mouse stem cell virus, murine leukemia virus, feline leukemia virus, feline sarcoma virus, and avian reticuloendotheliosis viruses.

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

A vector that encodes a core virus is also known as a "viral vector." There are a large number of available viral vectors that are suitable for use with the invention, including those identified for human gene therapy applications, such as those described by Pfeifer and Verma (*Ann. Rev. Genomics Hum. Genet.* 2:177-211, 2001). Suitable viral vectors include vectors based on RNA viruses, such as retrovirus-derived vectors, e.g., Moloney murine leukemia virus (MLV)-derived vectors, and include more complex retrovirus-derived vectors, e.g., lentivirus-derived vectors. HIV-1-derived vectors belong to this category. Other examples include lentivirus vectors derived from HIV-2, FIV, equine infectious anemia virus, SIV, and maedi/visna virus. Methods of using retroviral and lentiviral viral vectors and packaging cells for transducing mammalian target cells with viral particles containing TCRs transgenes are well known in the art and have been previous described, for example, in U.S. Pat. No. 8,119,772; Walchli et al., *PLoS One* 6:327930, 2011; Zhao et al., *J. Immunol.* 174:4415-4423, 2005; Engels et al., *Hum. Gene Ther.* 14:1155-68, 2003; Frecha et al., *Mol. Ther.* 18:1748-57, 2010; Verhoeyen et al., *Methods Mol. Biol.* 506:97-114, 2009. Retroviral and lentiviral vector constructs and expression systems are also commercially available.

In a specific embodiment, a viral vector is used to introduce the non-endogenous nucleic acid sequence encoding TCRα chain specific for the peptide antigen into the hematopoietic progenitor cells. In another embodiment a viral vector is used to introduce non-endogenous nucleic acid sequence encoding DL1 or DL4 and a nucleic acid sequence encoding an MHC molecule into stromal cells. The viral vector may be a retroviral vector or a lentiviral vector. The viral vector may also include nucleic acid sequences encoding a marker for transduction. Transduction markers for viral vectors are known in the art and include selection markers, which may confer drug resistance, or detectable markers, such as fluorescent markers or cell surface proteins that can be detected by methods such as flow cytometry. In a particular embodiment, the viral vector further comprises a gene marker for transduction comprising green fluorescent protein or the extracellular domain of human CD2. Where the viral vector genome comprises more than one nucleic acid sequence to be expressed in the host cell as separate transcripts, the viral vector may also comprise additional sequence between the two (or more) transcripts allowing bicistronic or multicistronic expression. Examples of such sequences used in viral vectors include internal ribosome entry sites (IRES), furin cleavage sites, viral 2A peptide.

Other vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5: 1517-30, 1998).

Other vectors that have recently been developed for gene therapy uses can also be used with the methods of this disclosure. Such vectors include those derived from baculoviruses and alpha-viruses. (Jolly D J. 1999. Emerging viral vectors. pp 209-40 in Friedmann T. ed. 1999. The development of human gene therapy. New York: Cold Spring Harbor Lab).

The hematopoietic progenitor cells are cultured with stromal cells comprising a nucleic acid sequence encoding a non-endogenous DL1 or DL4 and a nucleic acid sequence encoding a MHC molecule under conditions and for a time sufficient to induce differentiation of hematopoietic progenitor cells into DN TCR$\alpha\beta^+$ thymocytes. In certain embodiments, the hematopoietic progenitor cells are cultured in a 6 cm or 10 cm tissue culture-treated dish. The concentration of hematopoietic progenitor cells in the culture can be between 1-$10^9$, preferably $1\times10^2$ to $1\times10^6$, more preferably $1\times10^3$ to $1\times10^4$. In some embodiments, hematopoietic progenitor cells (about 1-$5\times10^4$ cells) are cultured on a monolayer of OP9 cells expressing DL1.

One or more cytokines that promote commitment and differentiation of hematopoietic progenitor cells may also be added to the culture. The cytokines may be derived from human or other species. The concentration of a cytokine in culture can range from about 1 ng/ml to about 50 ng/ml. Representative examples of cytokines that may be used include: all members of the FGF family, including FGF-4 and FGF-2; Flt-3-ligand, stem cell factor (SCF), thrombopoietin (TPO), and IL-7. Cytokines may be used in combination with a glycosaminoglycan, such as heparin sulfate. Cytokines are commercially available or can be produced by recombinant DNA techniques and purified to various degrees. Some cytokines may be purified from culture media of cell lines by standard biochemical techniques.

The hematopoietic progenitor cells may be cultured in culture medium comprising conditioned medium, non-conditioned medium, or embryonic stem cell medium. Examples of suitable conditioned medium include IMDM, DMEM, or αMEM, conditioned with embryonic fibroblast cells (e.g., human embryonic fibroblast cells), or equivalent medium. Examples of suitable non-conditioned medium include Iscove's Modified Delbucco's Medium (IDMD), DMEM, or αMEM, or equivalent medium. The culture medium may comprise serum (e.g., bovine serum, fetal bovine serum, calf bovine serum, horse serum, human serum, or an artificial serum substitute) or it may be serum free.

Culture conditions entail culturing the hematopoietic progenitor cells for a sufficient time to induce differentiation of hematopoietic progenitor cells into DN TCR$\alpha\beta^+$ thymocytes. The cells are maintained in culture generally for about 4-5 days, preferably about 5 to 20 days. It will be appreciate that the cells may be maintained for the appropriate amount of time required to achieve a desired result, i.e., desired cellular composition. For example, to generate a cellular composition comprising primarily immature and inactivated T cells, the cells may be maintained in culture for about 5 to 20 days. Cells may be maintained in culture for 20 to 30 days to generate a cellular composition comprising primarily mature T cells. Non-adherent cells may also be collected from culture at various time points, such as from about several days to about 25 days. Culture methods for hematopoietic stem cells on stromal cells lines have been previously described (U.S. Pat. No. 7,575,925; Schmitt et al., *Nat. Immunol.* 5:410-417, 2004; Schmitt et al., *Immunity* 17:749-756, 2002).

Differentiation of hematopoietic progenitor cells into DN TCRαβ+ thymocytes may be detected and these cells isolated using standard flow cytometry methods. One or more cell sorts may be employed to isolate the DN TCRαβ+ thymocytes. For example, a first cell sort may identify hematopoietic progenitor cells expressing the transduction marker (i.e., marker for TCRα expression). In certain embodiments, a transduction marker is the extracellular domain of human CD2. In further embodiments, transduction marker positive cells may be subjected to a second cell sort to screen for cells that are $CD4^-$ and $CD8^-$. A third cell sort on the DN cells may screen for cells expressing TCRβ. It will be apparent to one skilled in the art that a subset of these sorts, or single or multiple cell sorts can be designed using different combinations of cell surface or transduction markers, in order to identify the desired subpopulation of DN TCRαβ+ thymocytes. Methods for sorting DN TCRαβ+ cells are known in the art (U.S. Pat. No. 7,575,925 and Schmitt et al., *Immunity* 17:749-756, 2002).

The nucleic acid sequences encoding the various TCRβ chains from the DN TCR$\alpha\beta^+$ thymocytes are isolated and introduced into T cells comprising the nucleic acid sequence encoding the TCRα chain from the parent TCR. As discussed herein, methods of cloning TCRβ chains from cells are well known in the art and have been previously described. In certain embodiments, once the nucleic acid sequences encoding the candidate TCRβ chains have been isolated from the DN TCR$\alpha\beta^+$ thymocytes, the nucleic acid sequences may be subjected to a further selection process whereby the TCRβ chains with the same $V_\beta$ gene used by the parent TCRβ chain are selected for introduction into T cells. Parent $V_\beta$ gene containing TCRβ chain may be identified within the sorted cell population using $V_\beta$ gene specific primers for PCR. One concern associated with enhancing the affinity of antigen-specific TCRs in vitro is that some modifications might increase the affinity of the receptor for MHC only, rather than peptide/MHC, thereby increasing the likelihood that the TCR will be autoreactive. Restricting the candidate TCRβ chains to those containing the parent $V_\beta$ gene increases the likelihood of retaining the TCR CDR1 and CDR2 domains that contact the MHC, and limiting variability to CDR3. As previously discussed, viral vectors, such as retroviral vectors and lentiviral vectors, are suitable for introducing the nucleic acid sequences encoding the various TCRβ chains and/or the parent TCRα into T cells. In some embodiments, the viral vector further comprises a gene marker for transduction (e.g. green fluorescent protein).

Cells that are capable of expressing a TCR on the cell surface are used for transformation or transduction with the nucleic acid sequences encoding the various TCRβ chains from the DN TCR$\alpha\beta^+$ thymocytes. Cells that are capable of expressing a TCR on the cell surface express a CD3 molecule. "CD3" is a multi-protein complex of six chains that are stably associated with a TCR on the cell surface. In mammals, the complex comprises a CD3γ chain, a CDδ chain, two CD3ε, and a homodimer of CD3ξ chains. The CD3γ, CD3δ, and CD3ε are highly related cell surface proteins of the immunoglobulin superfamily containing a single immunoglobulin domain. The transmembrane regions of CD3γ, CD3δ, and CD3ε are negatively charged, which is a characteristic that allows these chains to associate with the positively charged TCR chains. The cytoplasmic domains of the CD3γ, CD3δ, and CD3ε chains contain immunoreceptor tyrosine-based activation motifs (ITAMs) that allow them to associate with cytosolic protein tyrosine kinases following receptor stimulation and thereby signal to the cell interior. CD3 proteins are required for cell-surface expression of the TCR (see Janeway et al., *Immunobiology: The Immune System in Health and Disease,* 3rd Ed., Current Biology Publications, p. 4:39, 1997).

In some embodiments, cells that are capable of expressing a TCR on the cell surface are T cells, including primary cells or cell lines derived from human, mouse, rat, or other mammals. If obtained from a mammal, a T cell can be obtained from numerous sources, including blood, bone marrow, lymph node, thymus, or other tissues or fluids. A T cell may be enriched or purified. T cell lines are well known in the art, some of which are described in Sandberg et al., *Leukemia* 21:230-237, 2000. In certain embodiments, T cells which lack endogenous expression of TCRα and β chains are used. Such T cells may naturally lack endogenous expression of TCRα and β chains or may have been modified to block expression (e.g., T cells from a transgenic mouse that does not express TCR α and β chains or a cell line that has been manipulated to inhibit expression of TCR α and β chains). In certain embodiments, 58 $\alpha^-\beta^-$ cells, a murine T cell line that lacks endogenous TCRα and TCRβ chains, is used (Letourneur and Malissen, *Eur. J. Immunol.* 19:2269-74, 1989). In other embodiments, H9 T cell line is used (Catalog #HTB-176, ATCC, Manassas, Va.). In certain embodiments, cells that capable of expressing a TCR on the cell surface are not T cells or cells of a T cell lineage, but cells that have been modified to express CD3, enabling cell surface expression of a TCR (e.g., 293 cells or 3T3 cells). Cell surface expression of TCRs on cells that are not of a T cell lineage has been previously described (Szymczak et al., *Nat. Biotechnol.* 22:589-594, 2004).

To identify a potential enhanced affinity TCR, once cells that capable of expressing a TCR on the cell surface that also express the parent TCRα chain have been transformed or transduced with a library of candidate TCRβ chains, antigen-specific cells are sorted or identified using MHC-peptide tetramer staining. MHC-peptide tetramer staining features a tetramer of MHC molecules, each comprising an identical peptide having an amino acid sequence that is cognate (e.g., identical or related to) at least one antigen, wherein the complex is capable of binding T cells specific for the cognate antigen. Each of the MHC molecules may be tagged with a biotin molecule. Biotinylated MHC/peptides are tetramerized by the addition of streptavidin, which is typically fluorescently labeled. The tetramer may be detected by flow cytometry via the fluorescent label. MHC-peptide tetramer staining methods for detecting antigen specific T cells are well known in the art (e.g., Altman et al., *Science* 274:94-96, 1996; Kalergis et al., *J. Immunol. Methods* 234:61-70, 2000; Xu and Screaton, *J. Immunol. Methods* 268:21-8, 2002; James et al., *J. Vis. Exp.*25:1167, 2009). In certain embodiments, the MHC-peptide tetramer comprises MHC Class I molecules. In other embodiments, the MHC-peptide tetramer comprises MHC Class II molecules. In further embodiments, the same peptide antigen used the culture step of the disclosed method is the same as the peptide incorporated into the MHC-peptide tetramer. In other embodiments, the MHC molecule expressed by the stromal cells in the culture step of the disclosed method is the same as an MHC molecule in the MHC-peptide tetramer. MHC-peptide tetramer stained cells may be sorted by flow cytometry one or more times. A first sort may select for transduced cells expressing a detectable transduction marker (e.g., green fluorescent protein). The transduction positive cells may also be sorted one or more times for cells that express the same Vβ chain as the parent TCR. It will be apparent to one skilled in the art that a subset of these sorts, or single or multiple cell sorts can be designed using different combinations of cell surface or transduction markers, in order to identify the desired subpopulation of cells.

An enhanced affinity TCR is identified by comparing the binding affinity of a candidate TCRαβ. Antigen-specific T cells may then be cloned and sequenced using standard molecular biology techniques. Candidate TCRβ clones may then be used to transduce T cells comprising the parent TCRα chain and MHC-peptide tetramer staining may be used to compare staining levels with the parent TCRαβ, as previously described. Increased staining observed with a candidate TCRβ may be indicative of enhanced affinity as compared with the parent TCRαβ. However, if the parent TCRαβ was codon-optimized for increased expression in the T cell, direct comparison of tetramer staining levels with the candidate TCRβ may not be possible. Candidate TCRβ chains may also be codon optimized for direct comparison with the parent TCRβ

A candidate TCRαβ has enhanced affinity compared to a parent TCRαβ if it has stronger binding to the peptide antigen than the parent TCRαβ. Enhanced affinity may be indicated by a TCR with a $K_a$ (equilibrium association constant) for the target antigen higher than that of the parent TCR, a TCR with a $K_D$ (dissociation constant) for the target antigen less than that of the parent TCR, or with an off-rate ($K_{off}$) for the target antigen less than that of the wild type (or parent) TCR. Methods of measuring TCR binding affinity have been previously described (e.g., Laugel et al., *J. Biol. Chem.* 282:23799-23810, 2007; Garcia et al., *Proc. Nat'l. Acad. Sci. USA* 98:6818-6823, 2001).

Enhanced Affinity TCRs and Compositions

In further embodiments, enhanced affinity TCRs generated by methods disclosed herein are provided. An enhanced affinity TCR may be cell-bound (e.g., expressed on the surface of a mature T cell) or in soluble form. In certain embodiments, enhanced affinity TCRs may be codon optimized to enhance expression in T cells (Scholten et al., *Clin. Immunol.* 119:135-145, 2006).

In other embodiments, enhanced affinity TCRs may also be a component of a fusion protein, which may further comprise a cytotoxic component (e.g., chemotherapeutic drugs such as vindesine, antifolates; bacterial toxins, ricin, anti-virals), which is useful for specific killing or disabling of a cancer cell or infected cell or a detectable component (e.g., biotin, fluorescent moiety, radionuclide), which is useful for imaging cancer cells, infected cells, or tissues under autoimmune attack.

The present disclosure also provides pharmaceutical compositions comprising an enhanced affinity TCR generated by the methods disclosed herein and a pharmaceutically acceptable carrier, diluents, or excipient. Suitable excipients include water, saline, dextrose, glycerol, ethanol, or the like and combinations thereof.

Applications

Enhanced affinity TCRs generated by the methods of the present disclosure may be used to treat a disease (such as cancer, infectious disease, or autoimmune disease) in a subject by administering a composition comprising the enhanced affinity TCRs.

Diseases that may be treated with enhance affinity TCR therapy include cancer, infectious diseases (viral, bacterial, protozoan infections), and autoimmune diseases. TCR gene therapy is a promising treatment for various types of cancer (Morgan et al., *Science* 314:126-129, 2006; reviewed in Schmitt et al., *Hum. Gene Ther.* 20:1240-8, 2009; reviewed in June, *J. Clin. Invest.* 117:1466-1476, 2007) and infectious disease (Kitchen et al., *PLoS One* 4:38208, 2009; Rossi et al., *Nat. Biotechnol.* 25:1444-54, 2007; Zhang et al., *PLoS Pathog.* 6:e1001018, 2010; Luo et al., *J. Mol. Med.* 89:903-913, 2011). Immunosuppressive gene therapy for autoimmune diseases using regulatory T cells comprising autoreactive TCRs is also an emerging treatment (Fujio et al., *J. Immunol.* 177:8140-8147, 2006; Brusko et al., *Immunol. Rev.* 223:371-390, 2008).

A wide variety of cancers, including solid tumors and leukemias are amenable to the compositions and methods disclosed herein. Types of cancer that may be treated include: adenocarcinoma of the breast, prostate, and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; leukemia; histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor. Further, the following types of cancers are also contemplated as amenable to treatment: adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin. The types of cancers that may be treated also include: angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

Exemplifying the variety of hyperproliferative disorders amenable to enhanced TCR therapy are B-cell cancers, including B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), Hairy cell leukemia and chronic myoblastic leukemia) and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt's lymphoma/leukemia, B-cell proliferations of uncertain malignant potential, lymphomatoid granulomatosis, and post-transplant lymphoproliferative disorder.

Autoimmune diseases include: arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), bullous pemphigoid, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant) vs NSIP, Guillain-Barré Syndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans.

In a particular embodiment, the method of treating a subject with the enhanced affinity TCRs generated by the methods disclosed herein include acute myelocytic leukemia, acute lymphocytic leukemia, and chronic myelocytic leukemia.

Infectious diseases include those associated with infectious agents and include any of a variety of bacteria (e.g., pathogenic *E. coli, S. typhimurium, P. aeruginosa, B. anthracis, C. botulinum, C. difficile, C. perfringens, H. pylori, V. cholerae, Listeria* spp., *Rickettsia* spp., *Chlamydia* spp., and the like), mycobacteria, and parasites (including any known parasitic member of the Protozoa). Infectious viruses include eukaryotic viruses (e.g., adenovirus, bunyavirus, herpesvirus, papovavirus, paramyxovirus, picornavirus, rhabdovirus (e.g., Rabies), orthomyxovirus (e.g., influenza), poxvirus (e.g., Vaccinia), reovirus, retroviruses, lentiviruses (e.g., HIV), flaviviruses (e.g., HCV) and the like). In certain embodiments, infection with cytosolic pathogens whose antigens are processed and displayed with MHC Class I molecules, are treated with the enhanced affinity TCRs of the invention.

The enhanced affinity TCRs may be administered to a subject in cell-bound form (i.e., gene therapy of target cell population (mature T cells (e.g., $CD8^+$ T cells) or other cells of T cell lineage)). In a particular embodiment, the cells of T cell lineage comprising enhanced affinity TCRs administered to the subject are autologous cells. In another embodiment, the enhanced affinity TCRs may be administered to a subject in soluble form. Soluble TCRs are known in the art (see, e.g., Molloy et al., 2005, *Curr. Opin. Pharmacol.* 5:438-443; U.S. Pat. No. 6,759,243). "Treat" and "treatment" refer to medical management of a disease, disorder, or condition of a subject (i.e., individual who may be a human or non-human mammal (e.g., primate, mouse, rat)). In general, an appropriate dose and treatment regimen provide the herein described enhanced affinity TCRs, and optionally, an adjuvant, in an amount sufficient to provide therapeutic or prophylactic benefit. Therapeutic and prophylactic benefits include improved clinical outcome; lessening or alleviation of symptoms associated with the disease; decreased occurrence of symptoms; improved quality of life; longer disease-free status; diminishment of extent of disease, stabilization of disease state; delay of disease progression; remission; survival; or prolonging survival.

Pharmaceutical compositions including the enhanced affinity receptors may be administered in a manner appropriate to the disease or condition to be treated (or prevented) as determined by persons skilled in the medical art. An appropriate dose, suitable duration, and frequency of administration of the compositions will be determined by such factors as the condition of the patient, size, type and severity of the disease, particular form of the active ingredient, and the method of administration.

In further embodiments, enhanced affinity TCRs of the instant disclosure may be used in diagnostic methods or imaging methods, including these methods used in relation to the indications or conditions identified herein.

EXAMPLES

The following examples demonstrate that, as provided by the instant disclosure, for example, TCR transgenic thymocytes efficiently differentiate into a "γδ like" $CD4^-CD8^-CD24^-TCR\beta^+$ lineage when exposed to their cognate antigen in OP9-DL1 cultures. Furthermore, progenitor thymocytes expressing only the TCRα chain from a T cell clone specific for the tumor antigen WT1 can also differentiate into this mature TCRαβ+ lineage in OP9-DL1 culture. A library of TCRβ chains was generated from a population of DN TCRαβ+ cells sorted from these cultures, and screened for WT1 MHC tetramer reactivity when paired with the antigen-specific TCRα chain. Using this approach, several TCRβ chains were identified that can pair with an antigen-specific TCRα chain to generate TCRs with up to 10-fold higher affinity for WT1 peptide as compared to the original TCR.

Example 1: Engagement of Peptide Agonist During Differentiation on OP9-DL1 Cells can Drive Differentiation of Mature TCRαβ+ DN Cells from T Cell Progenitors Purified from TCR Transgenic Mice Agonist signals through an αβ TCR prior to β-selection results in the differentiation of "γδ like" double negative (DN) $TCR\alpha\beta^+$ cells during T cell development in vivo, and TCR cross-linking at the DN3 stage leads to the differentiation of a similar lineage during in vitro T cell differentiation on OP9-DL1 cells. In order to determine whether progenitor T cells from TCR transgenic mice could also differentiate into a DN $TCR\alpha\beta^+$ lineage in response to cognate peptide antigen at the DN3 stage, $TCR\alpha\beta^-CD4^-CD8^-CD117^+CD44^+$ DN1 and DN2 progenitor thymocytes were sorted from transgenic OT-1 mice (express TCR specific for ovalbumin peptide sequence SIINFEKL (SEQ ID NO:1) presented on MHC Class I H-$2K^b$; Stock #003831, Jackson Laboratory, ME; see also Hogquist et al., *Cell* 76:17-27, 1994) and cultured with OP9-DL1 cells (Schmitt et al., *Immunity* 17:749-756, 2002; U.S. Pat. No. 7,575,925) transduced to express the mouse MHC Class I molecule H-$2K^b$, either in the absence of peptide, or with increasing concentrations of ovalbumin-specific peptide (SEQ ID NO:1) for 20 days and analyzed at various time points by flow cytometry. In the absence of peptide, double positive (DP) T cells could be detected by day 16, and constituted a major fraction of the culture by day 20 (FIG. 1A). However, the development or survival of DP T cells was diminished by even very low concentrations of peptide (0.0001 μM), and DP were completely absent from cultures containing 0.01 μM or more of peptide (FIG. 1A), demonstrating that DP cells are negatively selected by strong agonist signaling in OP9-DL1 cultures.

Figure 1B:
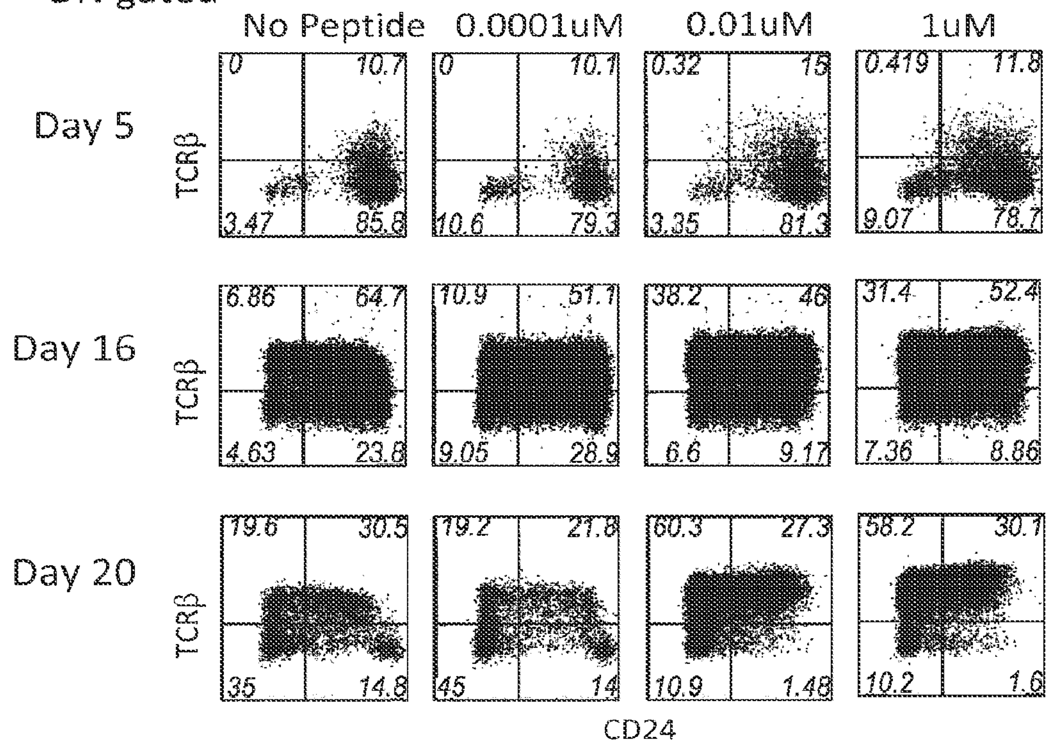
Figure 1C:
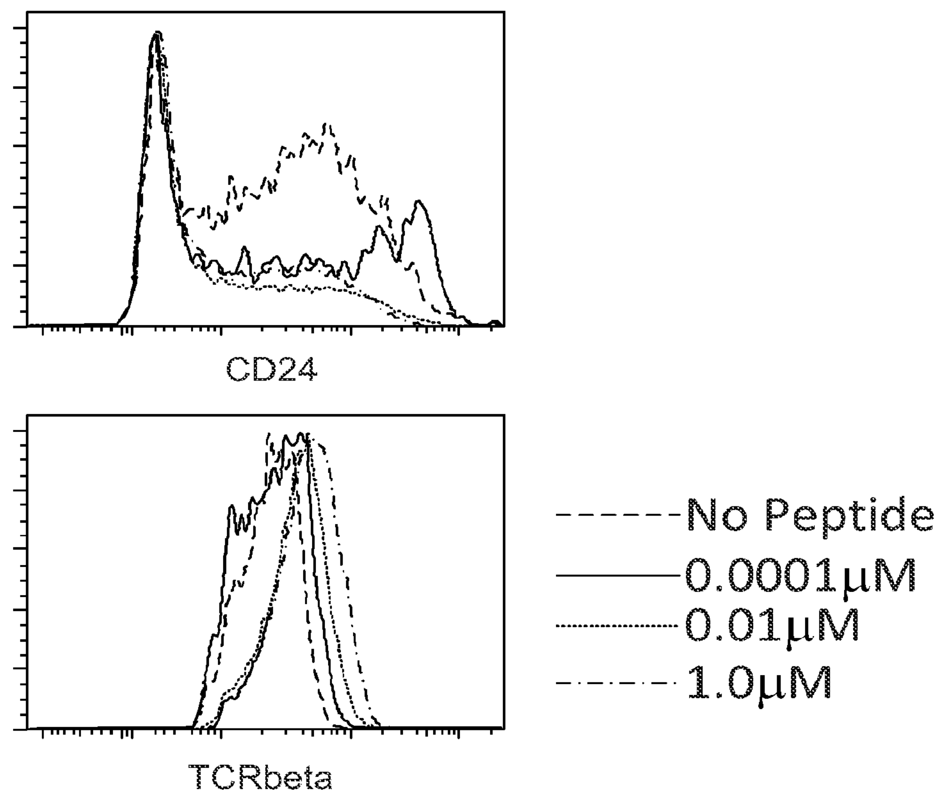
Figure 1D:
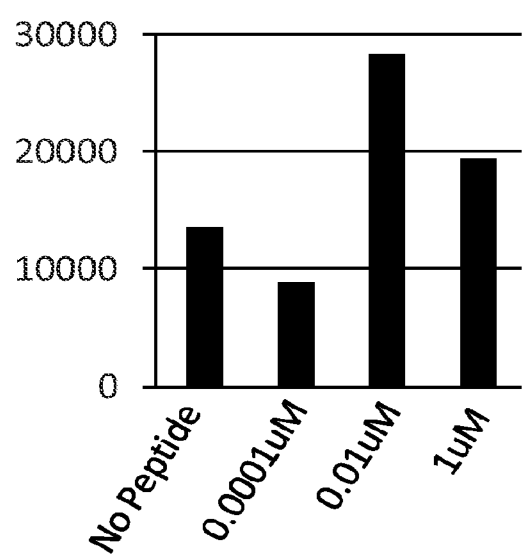
Figure 2:
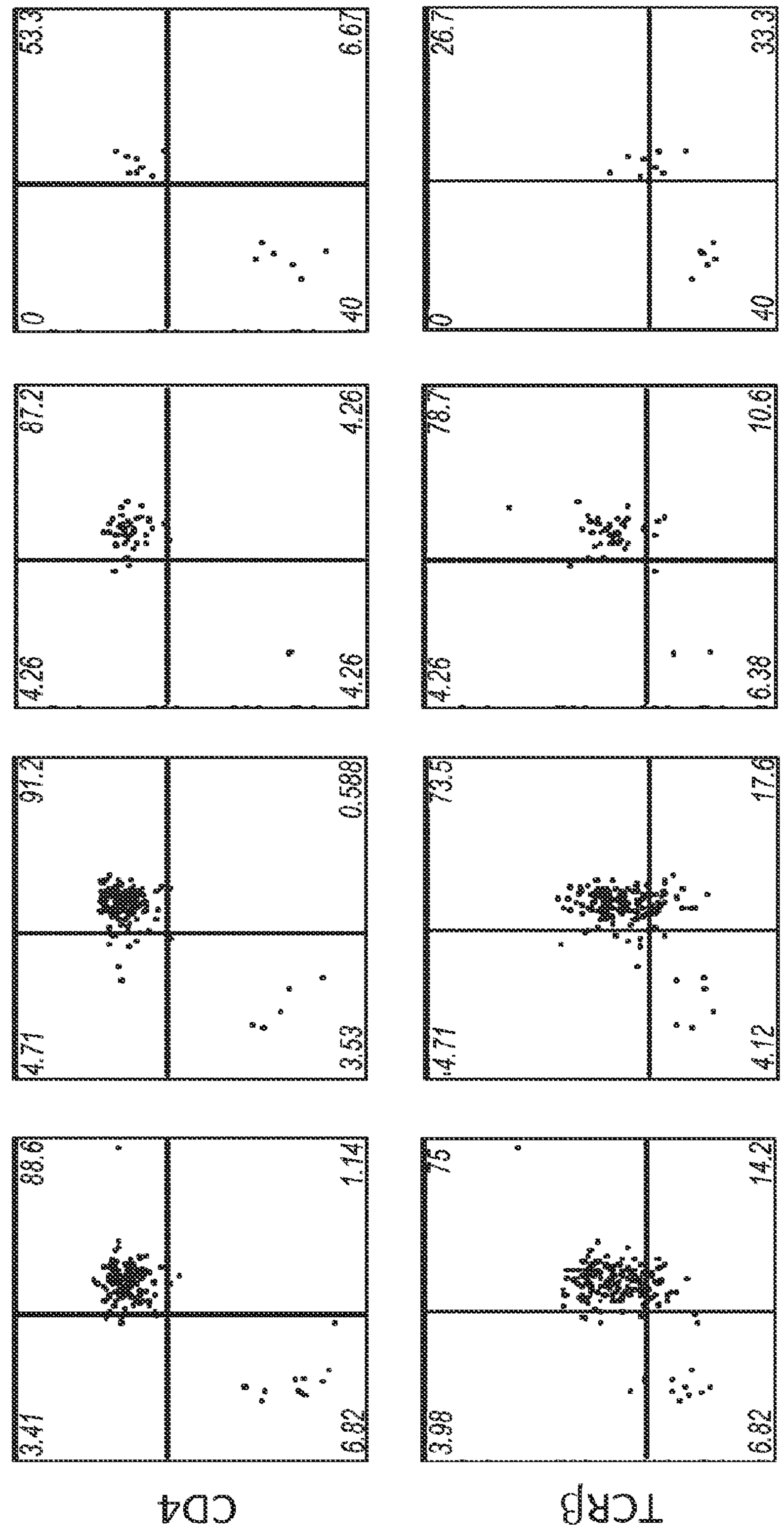
FIG. 2 shows CD69$^-$ DP thymocytes that have not yet gone through positive selection sorted from B6 or OT-1 transgenic mice were cultured on OP9-DL1 cells expressing MHC Class I H-2 Kb molecule in the presence of ovalbumin peptide SIINFEKL (SEQ ID NO:1).

In order to determine whether increasingly strong agonist signals drive the development of $TCR\alpha\beta^+$ DN cells, the DN population was analyzed for expression of CD24, a maturation marker that is expressed at high levels on all immature progenitor T cell populations, and TCRβ. The majority of cells were found to express high levels of CD24 and to lack TCRβ expression at day 5 (FIG. 1B), but by day 16, a majority of DN cells from all culture conditions expressed TCRβ, although a substantially greater number of $CD24^-$ cells were observed from cultures that contained 0.01 μM or more of peptide (38.2% and 31.4% $TCR^+CD24^-$ cells in cultures containing 0.01 and 1.0 μM of peptide, respectively, compared to 6.9% $TCR^+CD24^-$ in the no peptide culture) (FIG. 1B). By day 20, ~60% of all DN cells were $TCR\beta^+CD24^-$ from cultures containing 0.01 μM or 1.0 μM peptide, while in cultures that received no peptide or a low concentration (0.0001 μM) of peptide, only ~20% of DNs were $TCR\beta^+CD24^-$, and close to 50% were $TCR\beta^-$ (FIG. 1B, 1C). Furthermore, when the level of TCR surface expression is compared between the different culture conditions, the $TCR\beta^+$ cells that developed in response to high levels of peptide expressed higher levels of TCRβ on the cell surface (FIG. 1C). Without wishing to be bound by theory, it is possible that the development of some $TCR\alpha\beta^+$ DN cells in cultures without added peptide is due to cross-reactivity with other peptide-MHC ligands in the OP9-DL1 culture system. To confirm that the $TCR\alpha\beta^+$ DN cells observed in these cultures did not develop through a DP stage, $CD69^-$ DP cells that have not yet been positively selected were sorted from B6 or OT-1 thymus and cultured in the presence or absence of ovalbumin SIINFEKL peptide (SEQ ID NO:1). B6 DP cells were unaffected by the presence of SIINFEKL peptide (SEQ ID NO:1), but when OT-1 DP thymocytes were cultured on OP9-DL1 cells in the presence SIINFEKL (SEQ ID NO:1), all the hallmarks of negative selection were observed, including a massive loss of cellularity and co-receptor down-modulation (FIG. 2). Importantly, the DN cells observed in these cultures were uniformly TCR negative (FIG. 2).

These data indicate that engagement of a peptide agonist during differentiation on OP9-DL1 cells can drive the differentiation of mature TCRαβ$^+$ DN cells from T cell progenitors purified from TCR transgenic mice.

Example 2: Transgenic TCRα Chain Pairs with Endogenous TCRβ Chains to Drive the Development of DN CD24$^-$ TCRαβ$^+$ "γδ Wanna-be" Cells in the OP9-DL1 Culture System To determine whether the expression of only a TCRα chain prior to β-selection should also result in the lineage diversion of DN3 T cell progenitors that express an endogenous TCRβ chain that pairs with the introduced TCRα chain capable of engaging a peptide-MHC ligand in the OP9-DL1 culture system above a certain affinity threshold, CD4$^-$CD8$^-$CD117$^+$CD44$^+$ DN1 and DN2 progenitor thymocytes were sorted from B6 mice and transduced with a TCRα chain from the Wilm's tumor antigen (WT1) specific T cell clone 3D that had previously been identified as an affinity enhanced variant isolated from a saturation mutagenesis library of the CDR3 region of the 3Dα. The 3Dα expression construct contains an intra-ribosomal entry sequence motif, followed by the extracellular domain of human CD2 (Genbank Accession Nos. NM_001767.3 and NP_001758.2 (transcript and protein sequences for full length CD2, respectively)) (IRES-hCD2) as a marker transduction. Transduced progenitor thymocytes were cultured in the presence or absence of 1.0 μM of the MEW Class I H-2D$^b$ restricted WT1 peptide RMFPNAPYL (SEQ ID NO:2) for 14 days, and then analyzed by flow cytometry. DN cells within the hCD2 negative fraction contained few TCRαβ$^+$ cells, regardless of the presence of peptide in the culture conditions. In contrast, the hCD2 positive fraction (which expressed the 3Dα gene) from cultures that did not receive peptide contained 6.8% TCRβ$^+$ cells, and the number of TCRαβ$^+$ cells increased to 16.6% when 1.0 μM WT1 peptide was added (FIG. 3A). These data indicate that a significant population of TCRαβ$^+$ DN cells can develop from early progenitor thymocytes that ectopically express a TCRα chain prior to β-selection. Furthermore, the fact that this population of TCRαβ$^+$ DN cells increases when cognate peptide (for the introduced TCRα chain) is present suggests that a substantial fraction of these cells developed in response to WT1 antigen-specific signals.

Taken together, these data indicate that the TCRαβ$^+$ DN population could potentially contain cells that express a TCRβ chain that can pair with the introduced 3Dα to form a TCR with a higher affinity for the MHC-WT1 peptide tetramer than the original enhanced affinity receptor, and significantly higher than could be isolated from the normal T cell repertoire.

Therefore, 3Dα-transduced CD4$^-$CD8$^-$CD117$^+$CD44$^+$ DN1 and DN2 progenitor thymocytes were differentiated on OP9-DL1 cells expressing mouse MEW Class 1 H-2D$^b$ and also transduced to express WT1. Non-adherent cells were collected at for several days up to day 21 and sorted for hCD2$^+$CD4$^{-1}$CD8$^-$TCRβ$^+$ cells into TRIzol reagent (Invitrogen) (FIG. 3B). Cell sorts from individual days were pooled; RNA was purified, and cDNA was generated. The parent 3D TCR uses the Vb10 variable region. In order to retain the TCR CDR1 and CDR2 domains that contact MHC, we restricted the candidate TCRβ chains to those containing this variable region. Therefore, Vβ10-containing TCRβ chains within the sorted cell population were isolated by PCR using a Vβ10 specific forward primer, and a Cβ2 specific reverse primer (FIG. 3C). The Vb10-specific forward primer was designed to contain a CACC sequence allowing for directional TOPO-cloning into the pENTR™/D-TOPO® vector (Invitrogen), followed by transfer using Gateway® technology for recombination (Invitrogen) into the retroviral vector MigR1-attR (a version of the MigR1 vector (Pear et al., *Blood* 92:3780-3792, 1998) that has been modified to contain attR sites and the ccdB gene for Gateway® cloning). The MigR1-TCRβ library was used to transduce PlatE retroviral packaging cells (Morita et al., *Gene Therapy* 7:1063-1066, 2000; Cell Biolabs, Inc.) to generate retroviral supernatant, which was then used to retrovirally transduce 58 α$^-$β$^-$ cells, a murine T cell line that lacks endogenous TCRα and TCRβ chains, (58$^{-/-}$) (Letourneur and Malissen, *Eur. J. Immunol.* 19:2269-74, 1989).

Figure 4A:
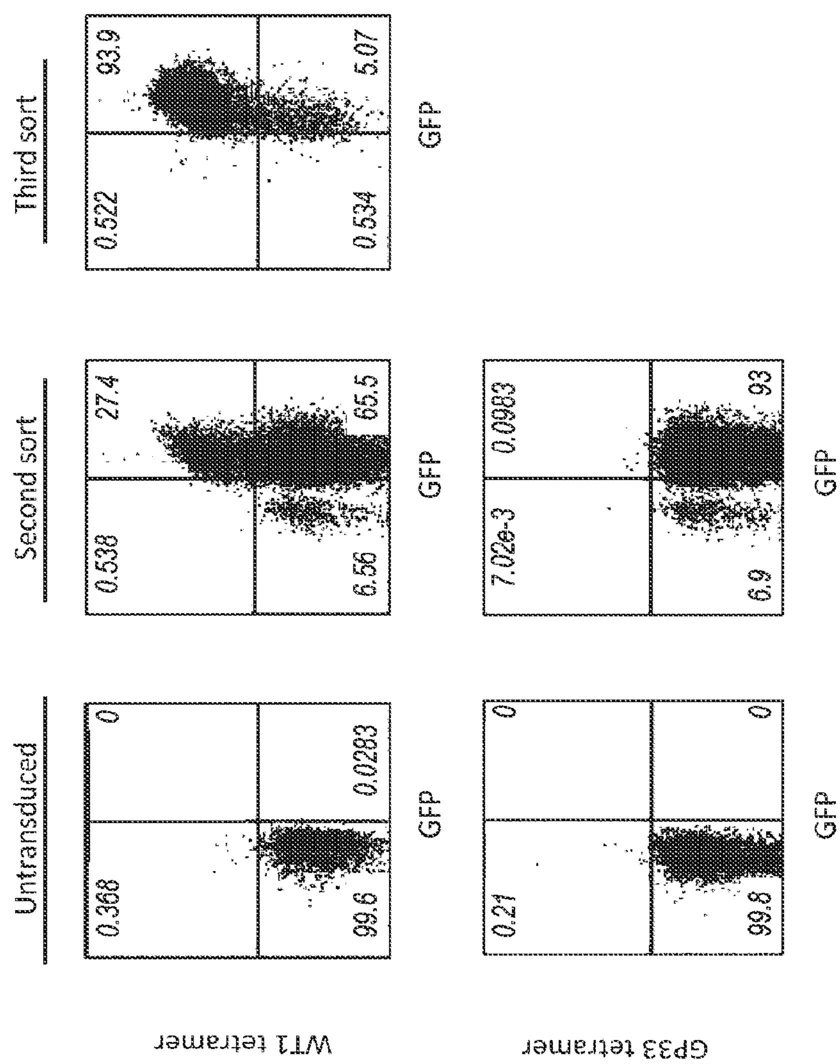

Retroviral TCRβ library supernatant was titrated, and a dilution that resulted in less than 20% transduced cells following transduction was used in order to ensure that most cells contained only one retroviral integration. Transduced cells were sorted first for GFP positive cells, and then resorted two more times on Vβ10$^+$ cells that also had high levels of MHC-WT1 peptide tetramer staining (FIG. 4A). Following the second sort, cells were analyzed for staining with an unrelated, but MHC H-2D$^b$-peptide tetramer specific for GP33, in order to assess whether MHC-WT1 peptide tetramer positive cells were binding in a peptide-independent manner to MHC residues (FIG. 4A).

Figure 4C:
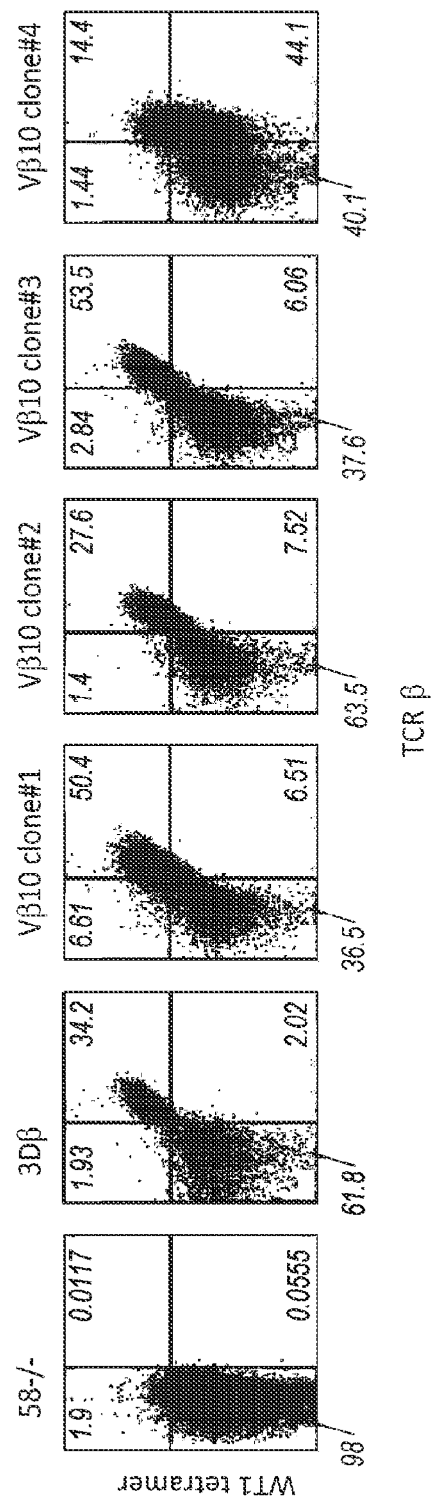

Following the third sort for MHC-WT1 peptide tetramer high, library-transduced 58$^{-/-}$ cells, the sorted cells were expanded, lysed, and the DNA was isolated. Retroviral inserts were recovered by PCR using MigR1-attR vector specific primers, designed to include AttB Gateway® cloning sites from the vector. Using a two-step approach, inserts were cloned first into the pDONR™ vector (Invitrogen) using Gateway® recombination cloning technology, and then back into MigR1-attR. Individual bacterial colonies were picked from the recombinational cloning reaction and sequenced. Following sequence analysis of >30 clones, the four most prevalent TCRβ chains were identified for further analysis. Interestingly, several of the clones had CDR3β sequences that shared multiple conserved residues with the original 3Dβ, chain (FIG. 4B). One of the clones (Clone #1) was found to be almost identical to the original 3Dβ, except for a P108Q substitution and a G112S substitution (FIG. 4B). The four candidate TCRβ chains were retrovirally transduced into 3Dα$^+$58$^{-/-}$ cells and analyzed by flow cytometry (FIG. 4*c*). All four candidate clones bound MHC-WT1 peptide tetramer when transduced into 3Da$^+$ 58$^{-/-}$ cells, although clone #4 bound MHC-WT1 peptide tetramer at significantly lower levels than the others and was not analyzed further. The parent 3Dβ chain had previously been codon-optimized, and therefore expressed higher levels of TCR at the cell surface, precluding direct comparison of tetramer staining levels between 3Dβ and the isolated clones.

Figure 5A:
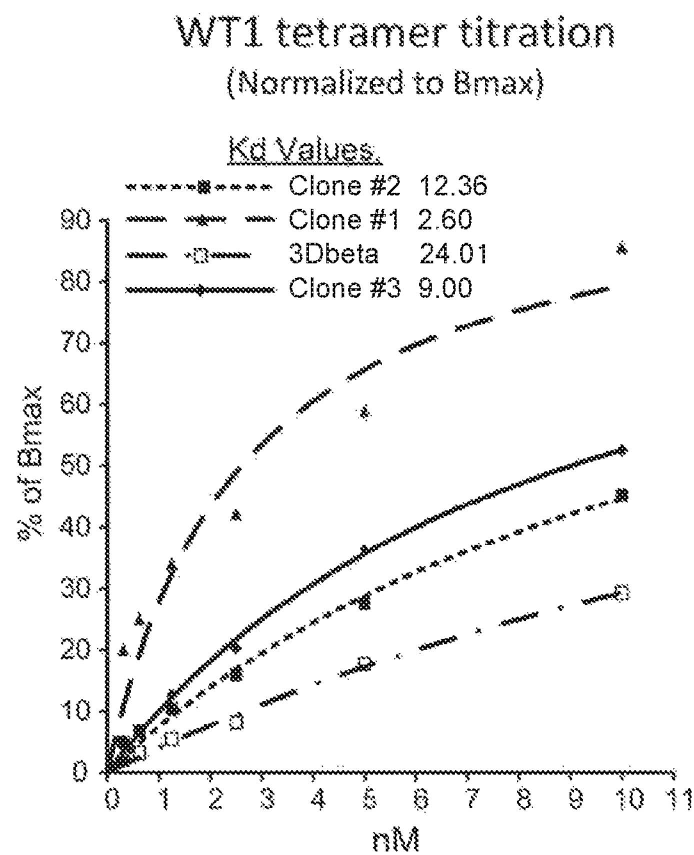
FIGS. 5A-C: (A) The relative affinity of the three highest affinity TCRs was determined by staining each transduced cell line with MHC-peptide tetramer followed by flow cytometry. $K_D$ measurements were performed using six 2-fold dilutions of PE-conjugated tetramers, and apparent $K_D$ values were determined from binding curves by non-linear regression, as the concentration of ligand that yielded half-maximal binding. (B) The highest affinity TCRβ chain (clone #1) was codon-optimized, and tetramer binding was compared to the original enhanced affinity 3Dαβ construct (C) 58$^{-/-}$ cells transduced with each of the candidate TCRβ chains paired with 3Dα were stained with MHC-WT1 peptide specific tetramer, as well as several non-specific MHC H-2Db-peptide tetramers in order to assess potential peptide-independent reactivity towards MHC.
Figure 5B:
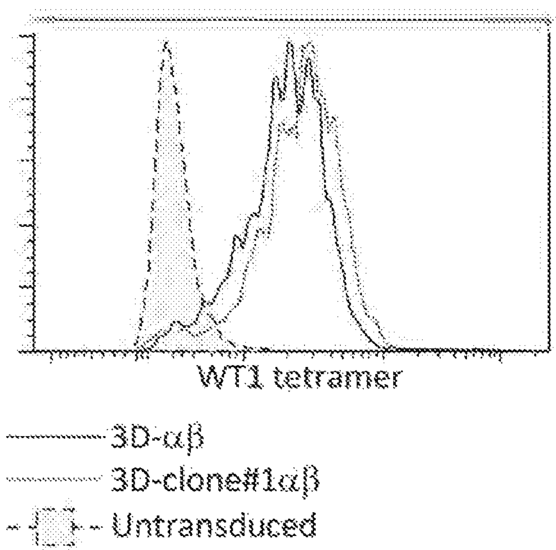

In order to more directly assess the relative affinity of each of the TCRβ chains for MHC-WT1 peptide tetramer, 3Dα$^+$ $58^{-/-}$ cells transduced with 3Dα, and each of the candidate TCRβ chains were stained with six 2-fold serial dilutions of MHC-WT1 peptide tetramer and MFI values were fit to a saturation binding curve by non-linear regression, as the concentration of ligand that yielded half-maximal binding (FIG. 5A). The apparent affinities of all three candidate TCRβ chains, when paired with 3Dα, were found to be higher than the parent 3Dβ, and Clone #1 had ~10 fold higher affinity (FIG. 5A). Therefore, in order directly compare tetramer staining of 3Dα paired with Clone #1 versus the parent 3Dβ Clone #1 was codon-optimized such that the only sequence differences between the original 3Dβ and Clone #1 were in the CDR3 region. Both constructs were transduced into $58^{-/-}$ cells and assessed by flow cytometry for MHC-WT1 peptide tetramer staining. When Clone #1 was codon-optimized, it was found to bind tetramer at a higher level than the original 3Dβ as expected (FIG. 5B).

Figure 5C:
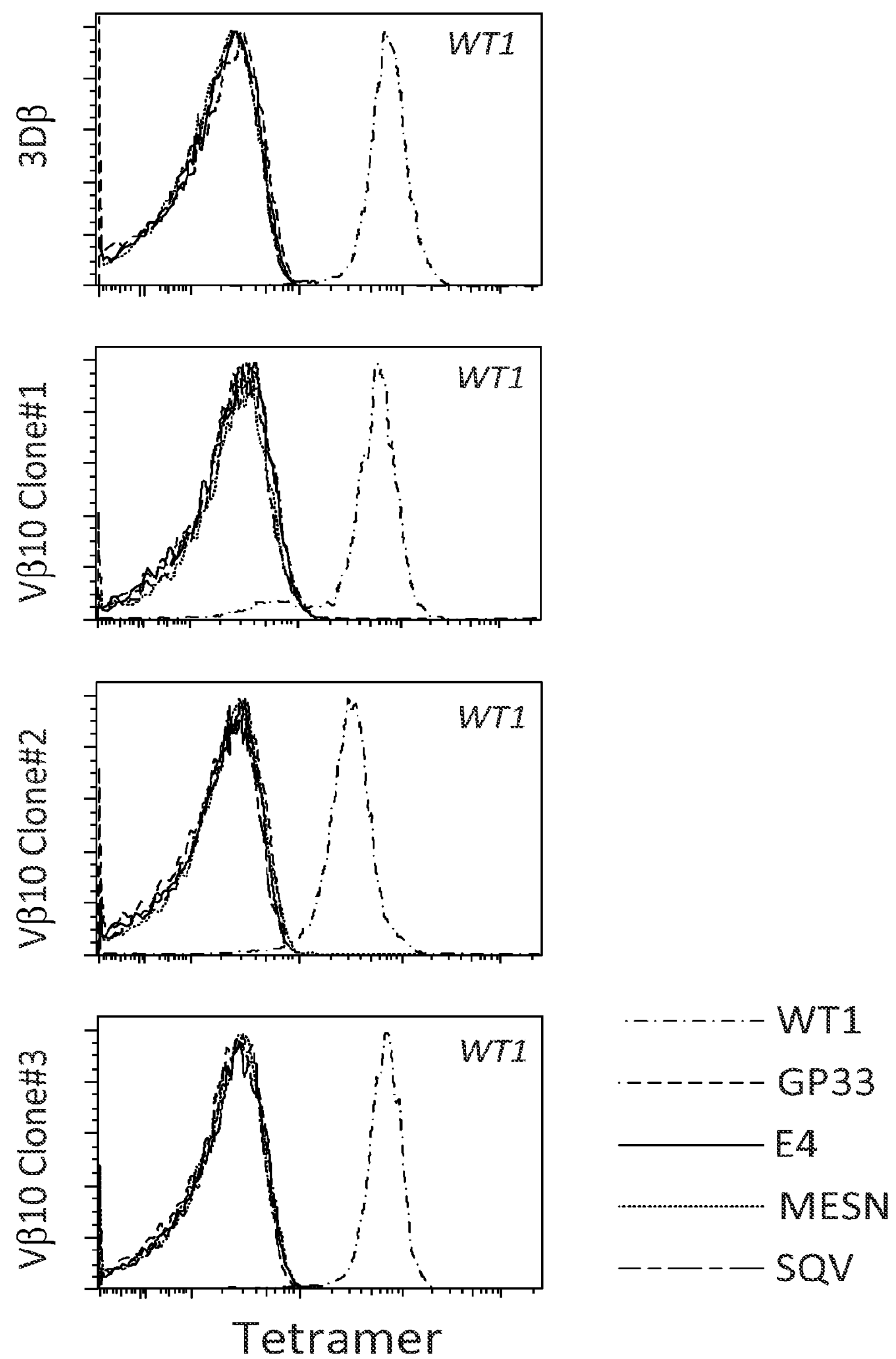
Figure 6:
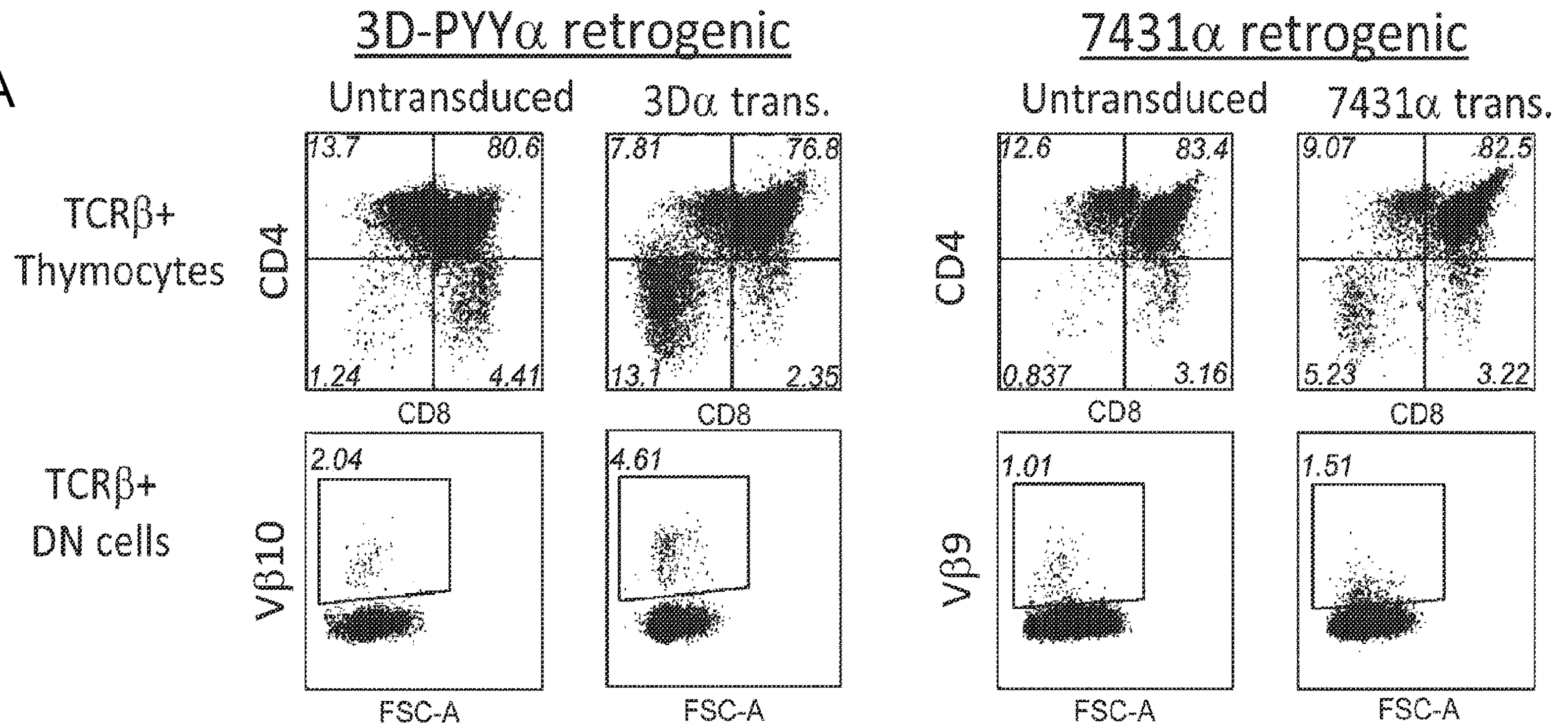
FIGS. 6A-B: Analysis of CD4 and CD8 expression of TCRβ$^+$ thymocytes (A) and splenocytes (B) from 3D-PYYα-IRES-hCD2 and 7431α-IRES-hCD2 retrogenic mice. Vβ10 and Vβ9 expression of TCRβ$^+$ thymocytes (A) from 3D-PYYα-IRES-hCD2 and 7431α-IRES-hCD2 retrogenic mice.
Figure 6:
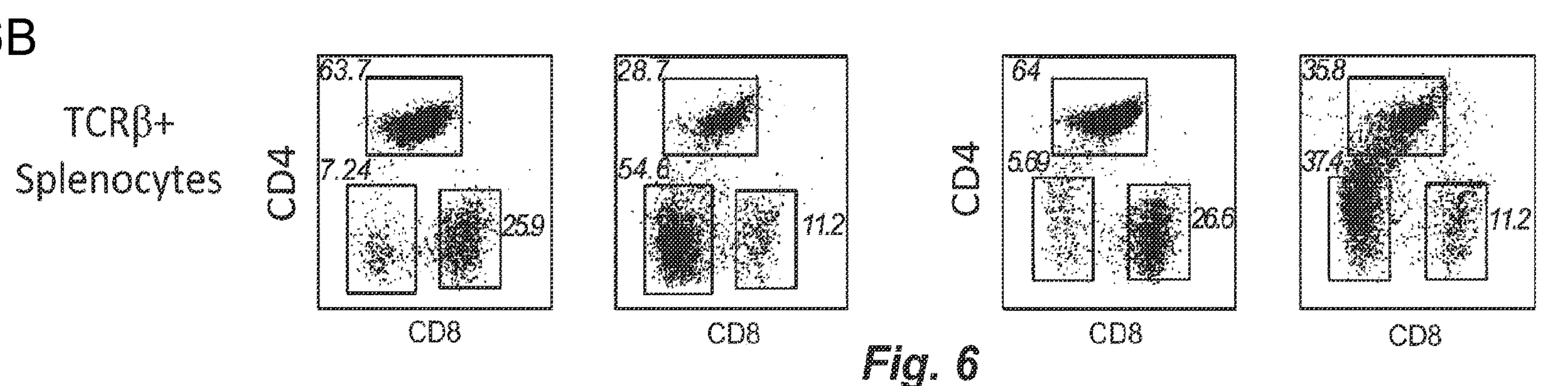
Figure 7:
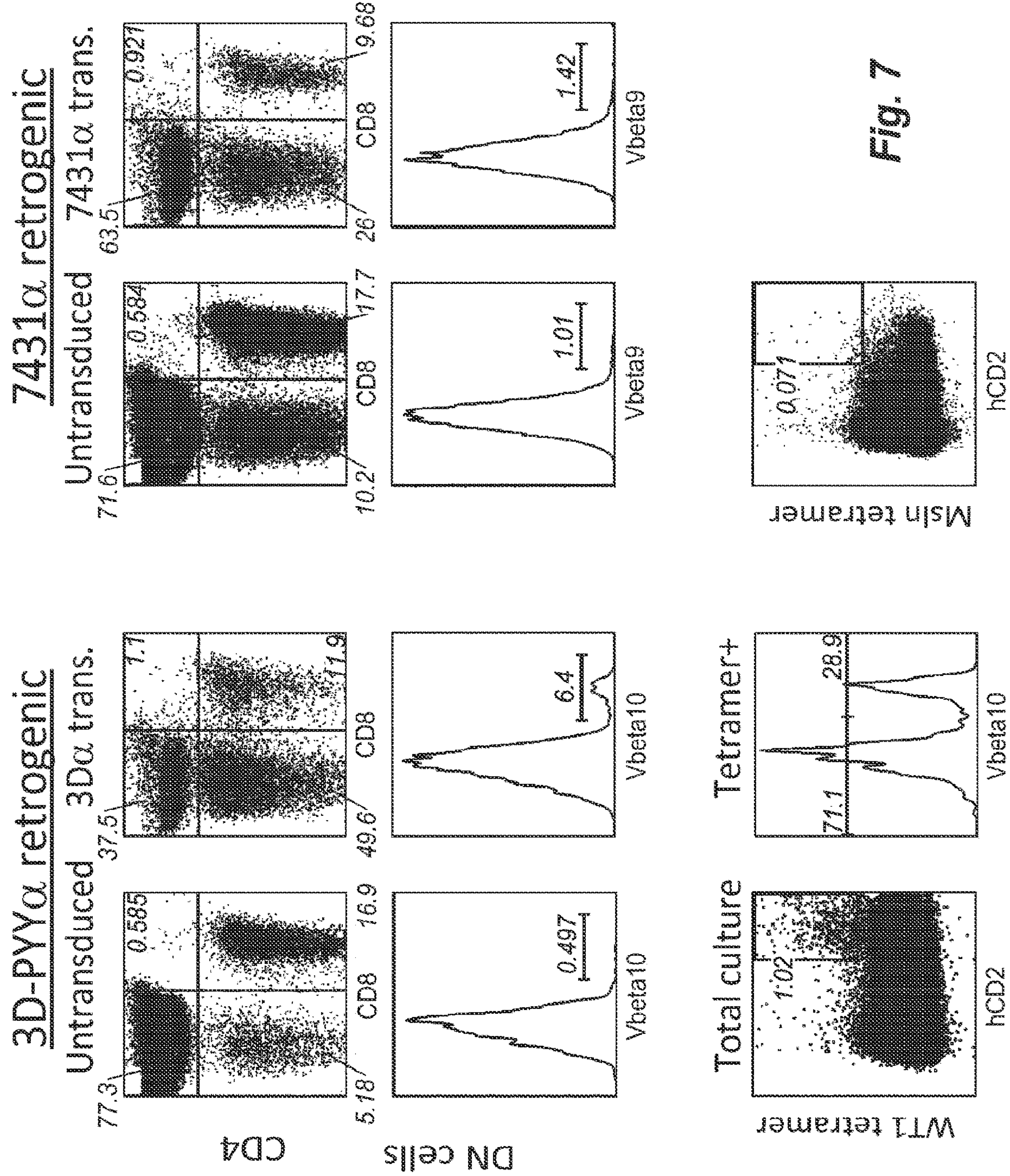
FIG. 7: Analysis of splenocytes from retrogenic mice after 6 days of WTI of mesothelin peptide stimulation +IL2 in vitro.

One concern associated with enhancing the affinity of antigen-specific TCRs in vitro is that some modifications might increase the affinity of the receptor for MHC only, rather than peptide/MHC, thereby increasing the likelihood that the TCR will be autoreactive. This risk was minimized by restricting the TCRβ library to TCRβ chains that share the same variable domain (Vb10) in order to restrict variability to CDR3. In order to determine whether any of the candidate TCRβ chains conferred an increased propensity to bind MHC H-$2D^b$ molecule in a peptide-independent manner, transduced $58^{-/-}$ cells were stained with a panel of MHC H-$2D^b$ tetramers (peptides: WT1, GP33, E4, MESN, SQV). All three candidate TCRβ chains were stained by the MHC-WT1 peptide tetramer at high levels when paired with 3Dα, similar to the original 3Dβ (FIG. 5C). When stained with four other MHC H-$2D^b$-peptide tetramers, all three TCRβ chains were uniformly negative for tetramer staining, suggesting that the increase in affinity observed for these receptors is not the result of an increased affinity for MHC alone (FIG. 5C).

Example 3: Generation of High Affinity WT1-specific T Cells by Ectopic Expression of an Antigen-specific TCRα Chain During Early Human T Cell Development In Vitro The Wilm's tumor (WT1) antigen is expressed at abnormally high levels on the surface of leukemia cells. HLA A2/WT1-specific T cell clones have been screened for clones with high specific activity. The TCRα and TCRβ chains from the C4 clone, which was determined to have the highest affinity for WT1, were isolated. A lentiviral vector comprising the C4 TCR and that confers high-level expression is subject of a TCR gene therapy clinical trial scheduled for 2012. In order to further enhance the affinity of the C4 TCR for the WT1 antigen, the in vitro differentiation system described in the previous examples was used with human cord blood progenitor cells expressing the C4 TCRα chain.

Generation of WT1-specific T Cells:

A variant of the OP9-DL1 cell line described in Example 1, which expressed the human Class I MHC molecule HLA-A2 (Genbank Accession Nos. U18930.1 and AAA87076.1, transcript and protein sequences, respectively) and human Class I MHC β2 microglobulin (β2M) molecule (Genbank Accession Nos. NM_004048.2 and NP_004039.1, transcript and protein sequences, respectively) was generated. The TCRα chain of the C4 TCR clone is stably transduced into cord blood-derived hematopoietic progenitor cells by retroviral transduction, using a retroviral vector that also encodes green fluorescent protein (GFP) as a transduction marker. Progenitor cells expressing GFP are sorted by flow cytometry and cultured on OP9-DL1-A2/β2M stroma cells in the presence or absence of WT1 peptide RMFPNAPYL (SEQ ID NO:2). Human hematopoietic progenitor cells readily proliferate and differentiate in OP9-DL1 culture to a stage of human T cell development characterized by the phenotype $CD34^{+}CD1a^{+}CD4^{+}$ (La Motte-Mohs et al., *Blood* 105:1431-1439, 2005), at which point they were undergoing TCR gene rearrangements at the β, γ, and δ loci (Spits, *Nat. Rev. Immunol.* 2:760-772, 2002). It is hypothesized that, like their murine counterparts, TCRα-expressing human T cell progenitors that produce an in-frame rearrangement at the TCRβ locus will adapt one of two cell fates: those expressing a TCRβ chain that does not pair well with the transgenic TCRα, or that pairs with the transgenic TCRα but does not receive a strong signal through this αβTCR, will differentiate to the DP stage in response to signaling though the pre-TCR; on the other hand, those that generate a TCRβ chain that can pair with the transgenic TCRα and receive a sufficiently strong signal through this mature αβTCR will be signaled to differentiate towards a DN TCRαβ+γδ-like lineage. Since DP cells only survive for ~3-4 days without a positive selection signal, and since efficient positive selection does not occur in OP9-DL1 cultures, the vast majority of cells that do not receive an agonist signal through the αβ TCR will be eliminated from the culture, allowing γδ-like cells that develop due to early αβ TCR signaling to accumulate.

Isolation of Candidate TCRβ Chains

At various points of the culture, non-adherent cells that have a DN TCRαβ+γδ-like phenotype and are WT1 peptide/A2 MHC-tetramer positive are collected by cell sorting. It may not be possible to detect WT1 tetramer positive cells, as the continued presence of antigen in the cultures may result in TCR down-modulation that could decrease tetramer staining below detection. Furthermore, since these cells are likely not to express CD8αβ, high affinity receptors that are not CD8-independent are undetectable by tetramer staining. Therefore, it may be necessary to screen the TCRβ chains from all DN TCRαβ+ cells that emerge in the culture (see below). It may also be desirable to restrict candidate T cells to those that use the same Vβ segment utilized by the original C4 TCRβ chain (Vβ17), in order to retain the CDR1 and CDR2 MHC contacts of the parent C4 TCR.

Following cell sorting, the endogenous TCRβ chains are cloned by purifying total RNA, performing full-length RACE RT-PCR with C-β1 or C-β2 primers, and cloning the PCR products into the pENTR™/D-TOPO® vector (Invitrogen), which allows directional TOPO-cloning and incorporates attL sites that allow rapid and efficient transfer to the retroviral vector Mig-attR (a variant of MigR1 (Pear et al., *Blood* 92:3780-3792, 1998) that contains attR sites for insertion of gene of interest) using Invitrogen's Gateway® technology recombination system. The products of the recombination reaction are electroporated into high efficiency bacteria, and colonies are scraped together and maxiprepped to generate a retroviral library of potentially WT1-reactive TCRβ chains.

Screening of High Affinity WT1-specific TCRs

TCRβ chains that can pair with the C4 TCRα chain to form a high affinity WT1-specific TCR are identified by transducing the TCRβ library into the human T cell line H9 (Catalog #HTB-176, ATCC, Manassas, Va.) that has been transduced to express the C4 TCRα chain (H9-C4α). Transduced cells are sorted by flow cytometry for high levels of MHC-WT1 peptide tetramer staining and retroviral inserts will be amplified by PCR from the sorted population.

Candidate TCRβ chains are identified by TOPO-cloning of the PCR product followed by sequence analysis. The selected TCRβ chains and the parental C4α are transduced into H9-C4α cells and the relative affinities for the MHC-WT1 peptide tetramer will be calculated by staining transduced cells with serial 2-fold dilutions of PE-conjugated tetramers (as described in Example 2). Affinity values are determined by fitting the MFI for each dilution to a binding curve by non-linear regression and KD defined as tetramer concentration yielding half-maximal binding. TCRβ chains that can pair with C4 TCRα to generate a TCR with higher affinity by MHC-peptide tetramer staining than the wildtype C4 receptor are further characterized for safety and efficacy.

Example 4: Characterization of the Efficacy and Safety of Candidate High Affinity TCRs Using an In Vivo Mouse Model of WT1-targeted TCR Gene Therapy Enhanced affinity human WT1-specific TCRs that were identified as in Example 3 were tested for safety and efficacy in an HLA-A2 transgenic mouse model of WT1 targeted gene therapy.

Assessing Enhanced TCRs for Off-target Activity:

Promiscuous activation of high affinity TCRs are assessed by measuring cytokine production by TCR-transduced T cells in response to a panel of A2 expressing target cells in the presence or absence of WT1 peptide. TCRs that exhibit off-target recognition of WT1 negative target cells compared to the parent C4 TCR are not advanced for further study.

Enhanced Affinity TCRs Activity on Normal Tissue In Vivo:

WT1 expression in normal tissue is similar in both mouse and man, and the WT1 peptide recognized by the C4 TCR is identical in mice and known to be processed and presented by mouse cells (Gaiger et al., *Blood* 96:1480-9, 2000). HLA-A2 transgenic mice have been used to test for recognition of normal tissues by T cells expressing human high affinity WT1-specific TCRs (Kuball et al., *J. Exp. Med.* 206:463-475, 2009).

In order to evaluate the safety of enhanced affinity TCRs generated in vitro as disclosed in the previous example, $CD8^+$ T cells from B6.A2/$D^b$ mice, which express a transgene encoding α1 and α2 domains of A2 fused to α3 of $D^b$ (for binding mouse CD8) (Newberg et al., *J. Immunol.* 156:2473-2480, 1996), were transduced to expressed candidate enhanced affinity TCRs. The TCRs were modified prior to transduction to contain mouse rather than human Cα and Cβ domains, which increases expression in mouse T cells (Pouw et al., *J. Gene Med.* 9:561-570, 2007). About 4-6 weeks following transfer of TCR-transduced T cells into mice, tissues known to naturally express WT1 (e.g., lungs and kidney) were analyzed by histology for evidence of T cell infiltration and tissue damage, and bone marrow was assessed by flow cytometry for depletion of WT1-expression hematopoietic progenitor cells.

Correlation of Enhanced Affinity with Improved Target Recognition and Function

There is evidence that an affinity threshold may exist for TCRs, above which further enhancements will not increase T cell function and may actually decrease antigen sensitivity (Schmid et al., *J. Immunol.* 184:4936-46, 2010). Therefore, the response of high affinity TCR-transduced $CD8^+$ T cells to target cells pulsed with limiting peptide concentrations were compared with T cells expressing the parent C4 TCR. Cytokine production (IFNγ/IL-2) and proliferation, as well as lytic activity, were analyzed. TCRs exhibiting increased affinity and enhanced function are advanced for further study and for potential use in TCR gene therapy trials.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A T cell receptor (TCR)-expressing cell, comprising a host cell modified to express on its cell surface a TCR specific for a peptide antigen, wherein the TCR-expressing cell is made by a method comprising:

(a) contacting a cell capable of differentiating into a cell of the T cell lineage with stromal cells and the peptide antigen, under conditions and for a time sufficient to induce differentiation, of the cell capable of differentiating into a cell of the T cell lineage, into a double negative (DN) TCRαβ+ thymocyte, wherein the cell capable of differentiating into a cell of the T cell lineage comprises a non-endogenous polynucleotide encoding a TCRα chain from a parent αβ TCR that is specific for the peptide antigen, wherein the parent TCR is a wild-type TCR, a human TCR, a mouse TCR, or a rat TCR, and wherein the stromal cells comprise a non-endogenous polynucleotide encoding Delta-like-1 or Delta-like-4 and a polynucleotide encoding an MHC molecule; and (b) introducing a polynucleotide encoding a TCRβ chain from the DN TCRαβ+ thymocyte generated in (a) into a cell capable of expressing a TCR on the cell surface and containing the non-endogenous polynucleotide encoding the TCRα chain from step (a), wherein the polynucleotide encoding a TCRβ chain from the DN TCRαβ+ thymocyte comprises the same Vβ gene as the β chain of the parent TCRβ, wherein the expressed TCRβ chain comprises a variation in a CDR3 as compared to the parent TCRβ chain;

wherein the expressed TCRβ chain and the expressed TCRα chain form a TCR, and wherein the cell capable of expressing a TCR on the cell surface is derived from $TCR\alpha^{-}/\beta^{-}$ 58 T cell hybridoma, thereby generating the TCR-expressing cell.

2. The TCR-expressing cell of claim 1, wherein the expressed TCR has enhanced affinity to the peptide antigen as compared to the parent TCR.

3. The TCR-expressing cell of claim 1, wherein the expressed TCRβ chain comprises the same CDR1 and CDR2 domains as the parent TCRβ chain.

4. The TCR-expressing cell of claim 1, wherein the cell capable of expressing a TCR on the cell surface comprises a CD4+ T cell.

5. The TCR-expressing cell of claim 1, wherein the cell capable of expressing a TCR on the cell surface comprises a CD8+ T cell.

6. The TCR-expressing cell of claim 1, wherein the peptide antigen is a viral antigen, a bacterial antigen, a cancer antigen, or an autoimmune antigen.

7. The TCR-expressing cell of claim 6, wherein the peptide antigen is a WT-1 antigen.

8. The TCR-expressing cell of claim 7, wherein the peptide antigen is a WT-1 antigen comprising the amino acid sequence of RMFPNAPYL (SEQ ID NO:2).

9. The TCR-expressing cell of claim 6, peptide antigen is a mesothelin antigen.

10. The TCR-expressing cell of claim 9, wherein the peptide antigen is a mesothelin antigen comprising the amino acid sequence of GQKMNAQAI (SEQ ID NO:31).

11. The TCR-expressing cell of claim 1, wherein the polynucleotide encoding the TCRα chain from a parent TCR and the polynucleotide encoding a TCRβ chain from the DN TCRαβ+ thymocyte are each codon optimized.

12. A composition, comprising the TCR-expressing cell of claim 1 and a pharmaceutically acceptable carrier, excipient, or diluent.

13. A method of treating a disease in a subject, comprising administering to the subject the TCR-expressing cell of claim 1, wherein the disease is associated with the peptide antigen, thereby treating the disease.

14. The method of claim 13, wherein the TCR-expressing cell comprises a CD4+ T cell.

15. The method of claim 13, wherein the TCR-expressing cell comprises a CD8+ T cell.

16. The method of claim 13, wherein the disease is a cancer, an infectious disease, or an autoimmune disease.

17. The method of claim 16, wherein the cancer is a solid tumor.

18. The method of claim 16, wherein the cancer is a leukemia.

19. The method of claim 16, wherein the cancer is selected from breast cancer, ovarian cancer, acute leukemia, vascular neoplasm, melanoma, colon cancer, lung cancer, thyroid cancer, bone and soft tissue sarcoma, or esophageal cancer.

20. The method of claim 18, wherein the cancer is acute myeloid leukemia, acute lymphocytic leukemia, or chronic myeloid leukemia.

21. The method of claim 16, wherein the disease is an autoimmune disease.

22. The method of claim 21, wherein the autoimmune disease is arthritis, inflammatory bowel disease, atherosclerosis, psoriasis, systemic lupus erythematosus, or diabetes.

23. The method of claim 16, wherein the disease is an infectious disease.

24. The method of claim 23, wherein the infectious disease is a bacterial infection.

25. The method of claim 23, wherein the infectious disease is a viral infection.

26. The method of claim 25, wherein the viral infection is an adenovirus, bunyavirus, herpesvirus, papovavirus, paramyxovirus, picornavirus, rhabdovirus, orthomyxovirus, poxvirus, reovirus, retrovirus, lentivirus, or flavivirus infection.

27. A method of treating a bacterial infection in a subject, comprising administering to the subject a T cell receptor (TCR)-expressing cell, comprising a host cell modified to express on its cell surface a TCR specific for a bacterial peptide antigen, wherein the TCR-expressing cell is made by a method comprising:

(a) contacting a cell capable of differentiating into a cell of the T cell lineage with stromal cells and the bacterial peptide antigen, under conditions and for a time sufficient to induce differentiation, of the cell capable of differentiating into a cell of the T cell lineage, into a double negative (DN) TCRαβ+ thymocyte, wherein the cell capable of differentiating into a cell of the T cell lineage comprises a non-endogenous polynucleotide encoding a TCRα chain from a parent αβ TCR that is specific for the bacterial peptide antigen, wherein the parent TCR is a wild-type TCR, a human TCR, a mouse TCR, or a rat TCR, and wherein the stromal cells comprise a non-endogenous polynucleotide encoding Delta-like-1 or Delta-like-4 and a polynucleotide encoding an MHC molecule; and (b) introducing a polynucleotide encoding a TCRβ chain from the DN TCRαβ+ thymocyte generated in (a) into a cell capable of expressing a TCR on the cell surface and containing the non-endogenous polynucleotide encoding the TCRα chain from step (a), wherein the polynucleotide encoding a TCRβ chain from the DN TCRαβ+ thymocyte comprises the same Vβ gene as the β chain of the parent TCRβ, wherein the expressed TCRβ chain comprises a variation in a CDR3 as compared to the parent TCRβ chain;

and wherein the expressed TCRβ chain and the expressed TCRα chain form a TCR.

28. The method of claim 27, wherein the expressed TCR has enhanced affinity to the bacterial peptide antigen as compared to the parent TCR.

29. The method of claim 27, wherein the expressed TCRβ chain comprises the same CDR1 and CDR2 domains as the parent TCRβ chain.

30. The method of claim 27, wherein the cell capable of expressing a TCR on the cell surface comprises a T cell.

31. The method of claim 30, wherein the cell capable of expressing a TCR on the cell surface comprises a CD4+ T cell.

32. The method of claim 30, wherein the cell capable of expressing a TCR on the cell surface comprises a CD8+ T cell.

33. The method of claim 30, wherein the T cell comprises a human T cell.

* * * * *